US006399371B1

(12) United States Patent
Falduto et al.

(10) Patent No.: US 6,399,371 B1
(45) Date of Patent: *Jun. 4, 2002

(54) HUMAN MATRIX METALLOPROTEASE GENE, PROTEINS ENCODED THEREFROM AND METHODS OF USING SAME

(75) Inventors: Michael T. Falduto, Glencoe; Scott R. Magnuson, Park Ridge; Douglas W. Morgan, Libertyville, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/391,104

(22) Filed: Sep. 7, 1999

Related U.S. Application Data

(63) Continuation of application No. 08/814,394, filed on Mar. 11, 1997, now abandoned.

(51) Int. Cl.$^7$ .......................... C07H 21/04; C12N 5/06
(52) U.S. Cl. ............ 435/325; 435/320.1; 435/252.33; 435/219; 435/226; 536/23.1; 536/23.2; 536/23.5
(58) Field of Search .................. 435/219, 226, 435/252.3, 252.33, 325, 320.1; 536/23.2, 23.5, 23.1

(56) References Cited

U.S. PATENT DOCUMENTS 5,236,844 A * 8/1993 Basset et al. ............ 435/320.1

FOREIGN PATENT DOCUMENTS

| EP | 0 522 169 | | 1/1993 |
|---|---|---|---|
| WO | WO 92/09701 | | 6/1992 |
| WO | WO 9514772 | * | 6/1995 |
| WO | WO 95/25171 | | 9/1995 |
| WO | WO 97/19178 | | 5/1997 |
| WO | WO 97/40157 | | 10/1997 |

OTHER PUBLICATIONS

Basset, et al., "Matrix Metalloproteinases as Stormal Effectors of Human Carcinoma Progression: Therapeutic Implications", Matrix Biology, vol. 15 (1997), pp. 535–541.
Basset, et al., "A novel mealloproteinase gene specifically expressed in stromal cells of breast carcinomas", Nature, vol. 348 (1990), pp. 699–704.
Bode, et al., "The metzincins: A superfamily of structurally related metalloproteinases", Zoology, vol. 99, (1995/96), pp. 237–246.
Cossins, et al.; "Identification of MMP–18, a Putative Novel Human Matrix Metalloproteinase"; *Biochemical and Biophysical Research Communications*, vol. 228, 1996, pp. 494–498.
Davidson, et al., "The inhibition of matrix metalloproteinase enzymes", Chemistry and Industry, (1997), pp 258–262.
B. Davies, et al., "A Synthetic Matrix Metalloproteinase Inhibitor Decreases Tumor Burden and Prolongs Survival of Mice Bearing Human Ovarian Carcinoma Xenografts", Cancer Research, vol. 53, pp 2087–2091 (1993).
A.J. P. Docherty and G. Murphy, "The tissue metalloproteinase family and the inhibitor TIMP: a study using cDNAs and recombinant proteins", Annals Rheumatic Diseases, vol. 49, pp 469–479 (1990).
W. B. Ennis and L.M. Matrisian, "Matrix degrading metalloproteinases", Journal of Neuro–Oncology, vol. 18, pp 105–109 (1994.
S.M. Frisch & H.E. Ruley, "Transcription from the Stromelysin Promoter is Induced by Interleukin–1 and Repressed by Dexamethasone*", Journal of Biological Chem., vol. 262, No. 34, pp 16300–16304 (1987).
Hasty, et al., "Human Neutrophil Collagenase", The Journal of Biological Chemistry, vol. 265 (1990), pp. 11421–11424.
Hooper, "Families of zinc metalloproteases", FEBS Letters, vol. 354 (1994), pp. 1–6.
Kolb, et al.; "The matrix metalloproteinase RASI–1 is expressed in synovial blood vessels of a rheumatoid arthritis patient"; *Immunology Letters*, vol. 57, 1997, Amersterdam, pp. 83–88.
L. M. Matrisian, "The Matrix–Degrading Metalloproteinases", Bio. Essays, vol. 14, No. 7, pp 455–463 (1992).
S. S. McCachren, "Expression of Metalloproteinases and Metalloproteinase Inhibitor in Human Arthritic Synovium", Arthritis and Rheumatism, vol. 34, No. 9, pp. 1085–1093 (1991).
M. K. Margulies, et al., "Urinary Type IV Collagenase: Elevated Levels are Associated with Bladder Transitional Cell Carcinoma", Cancer Epidemiology, Biomarkers & Prevention, vol. 1, Sep/Oct. 1992, pp 467–474.
D. Moscatelli and D.B. Rifkin, "Membrane and matrix localization of proteinases: a common theme in tumor cell invasion and angiogenesis", Biochim Biophysica Acta., vol. 948, pp 67–85 (1988).
Mueller, et al., "Stromelysin–3 expression in early (pT1) carcinomas and pseudoinvasive lesions of the colorectum", Virchows Arch, vol. 430 (1997), pp 213–219.

(List continued on next page.)

*Primary Examiner*—Nashaat T. Nashed
(74) *Attorney, Agent, or Firm*—Dianne Casuto

(57) ABSTRACT

The present invention provides novel complementary DNA (cDNA) sequences encoding human matrix metalloprotease proteins (MMP-ABT). The present invention also provides recombinant DNA molecules encoding human matrix metalloprotease polypeptides and processes for producing the novel proteins. The cDNA is cloned into expression vectors for expression in recombinant hosts. The cDNA is useful to produce recombinant full length MMP-ABTs or fragments thereof. The cDNA and the recombinant proteins derived therefrom and/or antibodies to the proteins are useful in diagnostic assays and for the development of therapeutic agents that affect MMP function.

7 Claims, 18 Drawing Sheets

OTHER PUBLICATIONS

Murphy, et al., Relating Matrix Metalloproteinase Structure to Function: Why the "Hemopexin Domain?", Matrix Biology, vol. 15 (1997), pp 511–518.

A.M. Pendas, et al., "Identification and Characterization of a Novel Human Matrix Metalloproteinase with Unique Structural Characteristics, Chromosomal Location, and Tissue Distribution", Journal of Biological Chemistry, vol. 272, No. 7, Feb. 14, 1997, pp 4281–4286.

Peng, et al., "A Gene Delivery System Activatable by Disease–Associated Matrix Metalloproteinases", Human Gene Therapy, vol. 8 (1997), pp 729–738.

Puente, et al., "Molecular Cloning of a Novel Membrane–type Matrix Metalloproteinase from a Human Breast Carcinoma", Cancer Research, vol. 56 (1996), pp. 944–949.

Sang, et al.; "Computational Sequence Analysis of Matrix Metalloproteinases", Journal of Protein Chemistry, vol. 15, No. 2, 1996, pp. 137–160.

Santavicca, et al., "Characterization of structural determinants and molecular mechanisms involved in pro–stromelysin–3 activation by 4 aminophenylmercuric acetate and furin–type convertases", Biochem Journal, vol. 315 (1996), pp. 953–958.

Sato, et al., Activation of a recombinant membrane type 1–matrix metalloproteinase (MT1–MMP) by furin and its interaction with tissue inhibitor of metalloproteinases (TIMP)–2 FEBS Letters, vol. 393 (1996), pp. 101–104.

Sedlacek, et al.; "Matrix Metalloproteinase MMP–19 (RASI–1) is Expressed on the Surface of Activated Peripheral Blood Mononuclear Cells and is Detected as an Autoantigen in Rheumatoid Arthritis"; Immunobiology, vol. 198, No. 4, 1998, Stuttgart, DE, pp. 408–423.

M.E. Stearns & M. Wang, "Immunoassays of the Metalloproteinase (MMP–2) and Tissue Inhibitor of Metalloproteinase (TIMP 1 and 2) Levels in Noninvasive and Metastatic PC–3 Clones: Effects of Taxol", Oncology Research, vol. 6, pp. 195–201 (1994).

W. G. Stetler–Stevenson, et al., "Extracellular matrix 6; Role of matrix metalloproteinases in tumor invasion and metastasis", FASEB Journal, vol. 7, pp 1434–1441 (1993).

* cited by examiner

Xaa Xaa Xaa Xaa Xaa Xaa Xaa Xaa Xaa Xaa Xaa Xaa Xaa Xaa Xaa Xaa
Xaa Leu Xaa Xaa Leu Leu Leu Leu Xaa Xaa Xaa Xaa Xaa Xaa Leu Xaa Xaa
Xaa Xaa Xaa Xaa Xaa Xaa Xaa Xaa Xaa Xaa Xaa Xaa Xaa Xaa Xaa Xaa Xaa
Xaa Tyr Leu Xaa Xaa Tyr Tyr Xaa Leu Xaa Xaa Xaa Xaa Xaa Xaa Xaa Xaa
Xaa Xaa Xaa Xaa Xaa Xaa Xaa Xaa Xaa Xaa Leu Xaa Xaa Met Gln Xaa Phe
Phe Gly Leu Xaa Val Thr Gly Lys Leu Asp Xaa Xaa Thr Leu Glu Xaa Met Xaa
Lys Pro Arg Cys Gly Val Pro Asp Xaa Xaa Xaa Xaa Xaa Xaa Xaa Xaa Val
Xaa Xaa Ph

```
1                                                             50
         *         *         *         *         *
CCTNCACTNGATTNAGCGATGCCATNAGAGCGTTTNAGTGGGTGTNCCAG
   X  T  X  X  S  D  A  X  R  A  F  X  W  V  X  Q 51                                                            100
         *         *         *         *         *
CTACCTGTNAGCGGCGTGTTGGACCGCGCCACCCTGCGCCAGATGANTNG
   L  P  V  S  G  V  L  D  R  A  T  L  R  Q  M  X  X 101                                                           150
         *         *         *         *         *
TCCCCGGTGCGGGGTTACAGATACCAACAGTTATGNGGCCTGGGNTGAGA
   P  R  C  G  V  T  D  T  N  S  Y  X  A  W  X  E 151                                                           200
         *         *         *         *         *
GGATCAGTGANTTGTTTGCTAGACAACGGACCAAAATGAGGCGTAAGAAA
   R  I  S  X  L  F  A  R  Q  R  T  K  M  R  R  K  K 201                                                           250
         *         *         *         *         *
CGNTTTGCAAAGCAAGGTAACAAATGGTANAAGCAGCACCTNTTCTACCG
   R  F  A  K  Q  G  N  K  W  X  K  Q  H  L  F  Y  R 251                                                           300
         *         *         *         *         *
NNTGGTGAACTGGGCTGAGNNTGTGCCGGAGCCGGCAGTTGGGGGCGCG
   X  V  N  W  A  E  X  V  P  E  P  A  V  G  G  A
```

FIG.2

```
CCACGCGTCCGGCTGCCCGAGCCGGGCTGCACCGGAGGCGGCGAGATGGT        50
GGTGCGCAGGCCGACGGGCTCGGCCCGACGTGGCCTCCGCCGCTCTACCA
                                              M  V

CGCGCGCGTCGGCCTTCTGCTGCGCGCCCTGCAGCTGCTACTGTGGGGCC       100
GCGCGCGCAGCCGGAAGACGACGCGCGGGACGTCGACGATGACACCCCGG
 A  R  V  G  L  L  R  A  L  Q  L  L  L  W  G

ACCTGGACGCCCAGCCCGCGGAGCGCGAAGGCCAGGAGCTGCGCAAGGAG       150
TGGACCTGCGGGTCGGGCGCCTCGCGCTTCCGGTCCTCGACGCGTTCCTC
 H  L  D  A  Q  P  A  E  R  E  G  Q  E  L  R  K  E pro-peptide
GCGGAGGCATTCCTAGAGAAGTACGGATACCTCAATGAACAGGTCCCCAA       200
CGCCTCCGTAAGGATCTCTTCATGCCTATGGAGTTACTTGTCCAGGGGTT
 A  E  A  F  L  E  K  Y  G  Y  L  N  E  Q  V  P  K AGCTCCCACCTCCACTCGATTCAGCGATGCCATCAGAGCGTTTCAGTGGG       250
TCGAGGGTGGAGGTGAGCTAAGTCGCTACGGTAGTCTCGCAAAGTCACCC
 A  P  T  S  T  R  F  S  D  A  I  R  A  F  Q  W TGTCCCAGCTACCTGTCAGCGGCGTGTTGGACCGCGCCACCCTGCGCCAG       300
ACAGGGTCGATGGACAGTCGCCGCACAACCTGGCGCGGTGGGACGCGGTC
 V  S  Q  L  P  V  S  G  V  L  D  R  A  T  L  R  Q ATGACTCGTCCCCGCTGCGGGGTTACAGATACCAACAGTTATGCGGCCTG       350
TACTGAGCAGGGGCGACGCCCCAATGTCTATGGTTGTCAATACGCCGGAC
 M  T  R  P̲  R̲  C̲  G̲  V̲  T̲  D̲  T  N  S  Y  A  A  W GGCTGAGAGGATCAGTGACTTGTTTGCTAGACACCGGACCAAAATGAGGC       400
CCGACTCTCCTAGTCACTGAACAAACGATCTGTGGCCTGGTTTTACTCCG
 A  E  R  I  S  D  L  F  A  R  H  R  T  K  M  R GTAAGAAACGCTTTGCAAAGCAAGGTGACAAATGGTACAAGCAGCACCTC       450
CATTCTTTGCGAAACGTTTCGTTCCACTGTTTACCATGTTCGTCGTGGAG
 R̲  K̲  K̲  R̲  F  A  K  Q  G  D  K  W  Y  K  Q  H  L catalytic domain
TCCTACCGCCTGGTGAACTGGCCTGAGCATCTGCCGGAGCCGGCAGTTCG       500
AGGATGGCGGACCACTTGACCGGACTCGTAGACGGCCTCGGCCGTCAAGC
 S  Y  R  L  V  N  W  P  E  H  L  P  E  P  A  V  R GGGCGCCGTGCGCGCCGCCTTCCAGTTGTGGAGCAACGTCTCAGCGCTGG       550
CCCGCGGCACGCGCGGCGGAAGGTCAACACCTCGTTGCAGAGTCGCGACC
 G  A  V  R  A  A  F  Q  L  W  S  N  V  S  A  L AGTTCTGGGAGGCCCCAGCCACAGGCCCCGCTGACATCCGGCTCACCTTC       600
TCAAGACCCTCCGGGGTCGGTGTCCGGGGCGACTGTAGGCCGAGTGGAAG
 E  F  W  E  A  P  A  T  G  P  A  D  I  R  L  T  F
```

FIG.4A

```
TTCCAAGGGGACCACAACGATGGGCTGGGCAATGCCTTTGATGGCCCAGG                                650
AAGGTTCCCCTGGTGTTGCTACCCGACCCGTTACGGAAACTACCGGGTCC
 F  Q  G  D  H  N  D  G  L  G  N  A  F  D  G  P  G

GGGCGCCCTGGCGCACGCCTTCCTGCCCCGCCGCGGCGAATTTTACTTCG                                700
CCCGCGGGACCGCGTGCGGAAGGACGGGGCGGCGCCGCTTAAAATGAAGC
  G  A  L  A  H  A  F  L  P  R  R  G  E  F  Y  F

ACCAAGATGAGCGCTGGTCCCTGAGCCGCCGCCGCGGGCGCAACCTGTTC                                750
TGGTTCTACTCGCGACCAGGGACTCGGCGGCGGCGCCCGCGTTGGACAAG
 D  Q  D  E  R  W  S  L  S  R  R  R  G  R  N  L  F

GTGGTGCTGGCGCACGAGATCGGTCACACGCTTGGCCTCACCCACTCGCC                                800
CACCACGACCGCGTGCTCTAGCCAGTGTGCGAACCGGAGTGGGTGAGCGG
 V  V  L  A  H  E  I  G  H  T  L  G  L  T  H  S  P

CGCGCCGCGCGCTCATGGCGCCCTACTACAAGAGGCTGGGCCGCGACG                                  850
GCGCGGCGCGCGCGAGTACCGCGGGATGATGTTCTCCGACCCGGCGCTGC
  A  P  R  A  L  M  A  P  Y  Y  K  R  L  G  R  D

CGCTGCTCAGCTGGGACGACGTGCTGGCCGTGCAGAGCCTGTATGGGAAG                                900
GCGACGAGTCGACCCTGCTGCACGACCGGCACGTCTCGGACATACCCTTC
  A  L  L  S  W  D  D  V  L  A  V  Q  S  L  Y  G  K hinge region
CCCCTAGGGGGCTCAGTGGCCGTCCAGCTCCCAGGAAAGCTGTTCACTGA                                950
GGGGATCCCCCGAGTCACCGGCAGGTCGAGGGTCCTTTCGACAAGTGACT
  P  L  G  G  S  V  A  V  Q  L  P  G  K  L  F  T  D CTTTGAGACCTGGGACTCCTACAGCCCCCAAGGAAGGCGCCCTGAAACGC                                1000
GAAACTCTGGACCCTGAGGATGTCGGGGGTTCCTTCCGCGGGACTTTGCG
  F  E  T  W  D  S  Y  S  P  Q  G  R  R  P  E  T hemopexin domain
AGGGCCCTAAATACTGCCACTCTTCCTTCGATGCCATCACTGTAGACAGG                                1050
TCCCGGGATTTATGACGGTGAGAAGGAAGCTACGGTAGTGACATCTGTCC
  Q  G  P  K  Y  C  H  S  S  F  D  A  I  T  V  D  R CAACAGCAACTGTACATTTTTAAAGGGAGCCATTTCTGGGAGGTGGCAGC                                1100
GTTGTCGTTGACATGTAAAAATTTCCCTCGGTAAAGACCCTCCACCGTCG
 Q  Q  Q  L  Y  I  F  K  G  S  H  F  W  E  V  A  A TGATGGCAACGTCTCAGAGCCCCGTCCACTGCAGGAAAGATGGGTCGGGC                                1150
ACTACCGTTGCAGAGTCTCGGGGCAGGTGACGTCCTTTCTACCCAGCCCG
   D  G  N  V  S  E  P  R  P  L  Q  E  R  W  V  G TGCCCCCCAACATTGAGGCTGCGGCAGTGTCATTGAATGATGGAGATTTC                                1200
ACGGGGGGTTGTAACTCCGACGCCGTCACAGTAACTTACTACCTCTAAAG
  L  P  P  N  I  E  A  A  A  V  S  L  N  D  G  D  F
```

FIG.4B

```
TACTTCTTCAAAGGGGGTCGATGCTGGAGGTTCCGGGGCCCCAAGCCAGT    1250
ATGAAGAAGTTTCCCCCAGCTACGACCTCCAAGGCCCCGGGGTTCGGTCA
 Y  F  F  K  G  G  R  C  W  R  F  R  G  P  K  P  V

GTGGGGTCTCCCACAGCTGTGCCGGGCAGGGGGCCTGCCCCGCCATCCTG    1300
CACCCCAGAGGGTGTCGACACGGCCCGTCCCCGGACGGGGCGGTAGGAC
  W  G  L  P  Q  L  C  R  A  G  G  L  P  R  H  P

ACGCCGCCCTCTTCTTCCCTCCTGTGCGCCGCCTCATCCTCTTCAAGGGT    1350
TGCGGCGGGAGAAGAAGGGAGGACACGCGGCGGAGTAGGAGAAGTTCCCA
 D  A  A  L  F  F  P  P  V  R  R  L  I  L  F  K  G

GCCCGCTACTACGTGCTGGCCCGAGGGGGACTGCAAGTGGAGCCCTACTA    1400
CGGGCGATGATGCACGACCGGGCTCCCCCTGACGTTCACCTCGGGATGAT
 A  R  Y  Y  V  L  A  R  G  G  L  Q  V  E  P  Y  Y

CCCCCGAAGTCTGCAGGACTGGGGAGGCATCCCTGAGGAGGTCAGCGGCG    1450
GGGGGCTTCAGACGTCCTGACCCCTCCGTAGGGACTCCTCCAGTCGCCGC
  P  R  S  L  Q  D  W  G  G  I  P  E  E  V  S  G

CCCTGCCGAGGCCCGATGGCTCCATCATCTTCTTCCGAGATGACCGCTAC    1500
GGGACGGCTCCGGGCTACCGAGGTAGTAGAAGAAGGCTCTACTGGCGATG
  A  L  P  R  D  G  S  I  I  F  F  R  D  D  R  Y

TGGCGCCTCGACCAGGCCAAACTGCAGGCAACCACCTCGGGCCGCTGGGC    1550
ACCGCGGAGCTGGTCCGGTTTGACGTCCGTTGGTGGAGCCCGGCGACCCG
  W  R  L  D  Q  A  K  L  Q  A  T  T  S  G  R  W  A

CACCGAGCTGCCCTGGATGGGCTGCTGGCATGCCAACTCGGGGAGCGCCC    1600
GTGGCTCGACGGGACCTACCCGACGACCGTACGGTTGAGCCCCTCGCGGG
  T  E  L  P  W  M  G  C  W  H  A  N  S  G  S  A

TGTTCTGAAGGCACCTCCTCACCTCAGAAACTGGTGGTGCTCTCAGGGCA    1650
ACAAGACTTCCGTGGAGGAGTGGAGTCTTTGACCACCACGAGAGTCCCGT
 L  F  *

AAATCATGTTCCCCACCCCCGGGGCAGAACCCCTCTTAGAAGCCTCTGAG    1700
TTTAGTACAAGGGGTGGGGGCCCCGTCTTGGGGAGAATCTTCGGAGACTC

TCCCTCTGCAGAAGACCGGGCAGCAAAGCCTCCATCTGGAAGTCTGTCTG    1750
AGGGAGACGTCTTCTGGCCCGTCGTTTCGGAGGTAGACCTTCAGACAGAC

CCTTTGTTCCTTGAAGAATGCAGCATTGTCTTTGTCTGTCCCCACCACAT    1800
GGAAACAAGGAACTTCTTACGTCGTAACAGAAACAGACAGGGGTGGTGTA

GGAGGTGGGGGTGGGATCAATCTTAGGAAAAGCAAAAAAGGGTCCCAGAT    1850
CGTCCCCCTACTTTTTTGAGTCGTCTCTTTAAGCTCTGGTkAAACGTTCTG
```

FIG.4C

```
CCTCCACCCCCACCCTAGTTAGAATCCTTTTCGTTTTTTCCCAGGGTCTA      1900
GGGAACCGGGAAAGGAGGCTCCTGAAGATAGGAGGGGTCCGGAAACAAAG

TTCGGCTAAAGGTACAGTTCCTTTCAAGAGGTAACAGCACTGGGATCCAA      1950
AAGCCGATTTCCATGTCAAGGAAAGTTCTCCATTGTCGTGACCCTAGGTT

GCAGGGGGATGAAAAACTCAGCAGAGAAATTCGAGACCATTTTGCAAGAC      2000
CGTCCCCCTACTTTTTGAGTCGTCTCTTTAAGCTCTGGTAAAACGTTCTG

TGTGCCCTTCTCCTCAGGACCCCCTGGCTCAGTTCTTGAAAAACGGTGTC      2050
ACACGGGAAGAGGAGTCCTGGGGGACCGAGTCAAGAACTTTTTGCCACAG

ATATTTAGTCAGAGGCCCCACCCCCAGGAAGCATGGATGGGGATGAAGGC      2100
TATAAATCAGTCTCCGGGGTGGGGGTCCTTCGTACCTACCCCTACTTCCG

ACAGGCGTCTCCAACCTCAGAGGCCCTTTGTGGGGTCAGGACACAGAGTG      2150
TGTCCGCAGAGGTTGGAGTCTCCGGGAAACACCCCAGTCCTGTGTCTCAC

GGAGGGAGACTGATGCAGGCCTACCAGTCCCTGGCTTTTTGTCTGGGGCT      2200
CCTCCCTCTGACTACGTCCGGATGGTCAGGGACCGAAAAACAGACCCCGA

GGAATAAAGAGGTGCCTTCAGCTGGTGGGCCGAGAGGCAGGAAGCAAAAA      2250
CCTTATTTCTCCACGGAAGTCGACCACCCGGCTCTCCGTCCTTCGTTTTT

AAAAAAAAAAAAAAAAAAAAAAAAA                               2275
TTTTTTTTTTTTTTTTTTTTTTTTT
```

FIG.4D

```
                      1                                                      50
MMP19         .......... .......MVA RVGLLLRALQ LLLWGHLDAQ PAEREGQELR
Matrilysin    .......... .......... ...MRLTVLC AVCL.LPGSL ALPLPQEAGG
Gelatinase A  .......... ..MEALMARG ALTGPLRALC LLGCLLSHA. AAAPSPIIKF
Gelatinase B  .......... .....MSLWQ PL...VLVLL VLGCCFAAP. RQRQSTLVLF
Stromelysin 1 .......... .......... ..MKSLPLLL LLCVAVCSAY PLDGAARGED
Stromelysin 2 .......... .......... ..MMHLAFLV LLCLPVCSAY PLSGAAKEED
Stromelysin 3 .......... MAPAAWLRSA AARALLPPML LLLLQPPPLL ARALPPDVHH
Collagenase 1 .......... ........M HSFPPLLLLL FWGV.VSHSF PATLETQEQD
Collagenase 2 .......... ........M FSLKTLPFLL LLHVQISKAF P..VSSKEKN
Collagenase 3 .......... .......... MHPGVLAAFL FLSWTHCRAL PLPSGGDEDD
MMP12         .......... .......... ...MKFLLIL LLQATASGAL PLNSSTSLEK
MMP18         .......... .......... .MNCQQLWLG FLLPMTVSGR VLGLAEVAPV
mt1MMP        ....MSPAPR PSRC...... ........LL LPLLTLGTAL ASLGSAQSSS
mt2MMP        MGSDPSAPGR PGWTGSLLGD REEAARPRLL PLLLVLLGCL GLGVAAEDAE
mt3MMP        .......... MILLTFSTGR RLDFVHHSGV FFLQTLLWIL CATVCGTEQY
mt4MMP        .......... .......... .......... .......... ..........
Consensus     ---------- ---------- -----L--LL LLLL-L--AL PL--S--E--

51                                                    100
MMP19         ......KEAE AFLEKYGYLN EQVP...KAP TST.RFSDAI RAFQWVSQLP
Matrilysin    MSELQWEQAQ DYLKRFYLYD SETKN..... ..ANSLEAKL KEMQKFFGLP
Gelatinase A  PGDVAPK.TD KELAVQYL.. NTFYGCPKES CNLFVLKDTL KKMQKFFGLP
Gelatinase B  PGDLRTNLTD RQLAEEYLYR YGYTRVAEMR GESKSLGPAL LLLQKQLSLP
Stromelysin 1 TS...MNLVQ KYLENYYDLK KDVKQFVRRK DSGPVV.KKI REMQKFLGLE
Stromelysin 2 SN...KDALQ QYLEKYYNLE KDVKQF.RRK DSNLIV.KKI QGMQKFLGLE
Stromelysin 3 LH......AE RR........ GPQPWHAALP .SSPAPAPAT QEAPR.....
Collagenase 1 V.....DLVQ KYLEKYYNLK NDGRQVEKRR NSGPVV.EKL KQMQEFFGLK
Collagenase 2 T.....KTVQ DYLEKFYQLP SNQYQSTRKN GTNVIV.EKL KEMQRFFGLN
Collagenase 3 LSEEDLQFAE RYLRSYYH.P TNLAGILKEN AASSMT.ERL REMQSFFGLE
MMP12         NNVL...FGE RYLEKFYGLE INKLPVTKMK YSGNLMKEKI QEMQHFLGLK
MMP18         .......... DYLSQYGYLQ KPLE..GSNN FKPEDITEAL RAFQEASELP
mt1MMP        FS......PE AWLQQYGYLP PGDLRTHTQR .SPQSLSAAI AAMQKFYGLQ
mt2MMP        VH......AE NWLRLYGYLP QPSRHRSTMR .SAQILASAL AEMQRFYGIP
mt3MMP        FN......VE VWLQKYGYLP PTSPRMSVVR .SAETMQSAL AAMQQFYGIN
mt4MMP        .......... .......... .......... .......... ..MQQFGGLE
Consensus     --------A- -YLEKYY-LP ---------R -S---L-EAL -EMQKFFGLP
```

FIG.5A

```
              101                                                           150
MMP19         VSGVLDRANL  RQMTRPRCGV  TDTNSYAAWA  ERISDLFARH  RTKMRRKKRF
Matrilysin    ITGMLNSRVI  EIMQKPRCGV  PDVAEYSLFP  N.........  ..........
Gelatinase A  QTGDLDQNTI  ETMRKPRCGN  PDVANYNFFP  R.........  ..........
Gelatinase B  ETGELDSATL  KAMRTPRCGV  PDLGRFQTFE  G.........  ..........
Stromelysin 1 VTGKLDSDTL  EVMRKPRCGV  PDVGHFRTFP  G.........  ..........
Stromelysin 2 VTGKLDTDTL  EVMRKPRCGV  PDVGHFSSFP  G.........  ..........
Stromelysin 3 ........PA  SSLRPPRCGV  PDPSDGLSAR  N.........  .....RQKRF
Collagenase 1 VTGKPDAETL  KVMKQPRCGV  PDVAQFVLTE  G.........  ..........
Collagenase 2 VTGKPNEETL  DMMKKPRCGV  PDSGGFMLTP  G.........  ..........
Collagenase 3 VTGKLDDNTL  DVMKKPRCGV  PDVGEYNVFP  R.........  ..........
MMP12         VTGQLDTSTL  EMMHAPRCGV  PDVHHFREMP  G.........  ..........
MMP18         VSGQLDDATR  ARMRQPRCGL  EDPFNQKTLK  Y.........  ..........
mt1MMP        VTGKADADTM  KAMRRPRCGV  PDKFGAEIKA  N.........  ..V..RRKRY
mt2MMP        VTGVLDEETK  EWMKRPRCGV  PDQFGVRVKA  N.........  ..LRRRRKRY
mt3MMP        MTGKVDRNTI  DWMKKPRCGV  PDQ..TRGSS  K.........  ..FHIRRKRY
mt4MMP        ATG,IDEATL  ALMKTPRCSL  PDLPVLT...  ..........  ...QARRRRQ
Consensus     VTGKLD--TL  E-MRKPRCGV  PDVG-F--FP  G---------  -----R-KR- 151                                                         200
MMP19         AKQGNKWYKQ  HLSYRLVNWP  EH..LPEPAV  RGAVRAAFQL  WSNVSALEFW
Matrilysin    ...SPKWTSK  VVTYRIVSYT  RD..LPHITV  DRLVSKALNM  WGKEIPLHFR
Gelatinase A  ...KPKWDKN  QITYRIIGYT  PD..LDPETV  DDAFARAFQV  WSDVTPLRFS
Gelatinase B  ...DLKWHHH  NITYWIQNYS  ED..LPRAVI  DDAFARAFAL  WSAVTPLTFT
Stromelysin 1 ...IPKWRKT  HLTYRIVNYT  PD..LPKDAV  DSAVEKALKV  WEEVTPLTFS
Stromelysin 2 ...MPKWRKT  HLTYRIVNYT  PD..LPRDAV  DSAIEKALKV  WEEVTPLTFS
Stromelysin 3 VLSGGRWEKT  DLTYRILRFP  WQ..LVQEQV  RQTMAEALKV  WSDVTPLTFT
Collagenase 1 ...NPRWEQT  HLTYRIENYT  PD..LPRADV  DHAIEKAFQL  WSNVTPLTFT
Collagenase 2 ...NPKWERT  NLTYRIRNYT  PQ..LSEAEV  ERAIKDAFEL  WSVASPLIFT
Collagenase 3 ...TLKWSKM  NLTYRIVNYT  PD..MTHSEV  EKAFKKAFKV  WSDVTPLNFT
MMP12         ...GPVWRKH  YITYRINNYT  PD..MNREDV  DYAIRKAFQV  WSNVTPLKFS
MMP18         LLLG.RWRKK  HLTFRILNLP  ST..LPPHTA  RAALRQAFQD  WSNVAPLTFO
mt1MMP        AIQGLKWQHN  EITFCIQNYT  PK..VGEYAT  YEAIRKAFRV  WESATPLRFR
mt2MMP        ALTGRKWNNH  HLTFSIQNYT  EK..LGWYHS  MEAVRRAFRV  WEQATPLVFQ
mt3MMP        ALTGQKWQHK  HITYSIKNVT  PK..VGDPET  RKAIRRAFDV  WQNVTPLTFE
mt4MMP        APAPTKWNKR  NLSWRVRTFP  RDSPLGHDTV  RALMYYALKV  WSDIAPLNFH
Consensus     A--GPKW-KT  HLTYRIVNYT  PD--LP---V  D-AIRKAF-V  WSNVTPLTFT
```

FIG.5B

```
              201                                                        250
MMP19         EAP.......  ATGPADIRLT  FFQGDHNDGL  GNAFDGPGGA  LAHAFLPR.R
Matrilysin    KV........  VWGTADIMIG  FARGAHGDSY  ..PFDGPGNT  LAHAFAPG.T
Gelatinase A  RI........  HDGEADIMIN  FGRWEHGDGY  ..PFDGKDGL  LAHAFAPG.T
Gelatinase B  RV........  YSRDADIVIQ  FGVAEHGDGY  ..PFDGKDGL  LAHAFPPG.P
Stromelysin 1 RL........  YEGEADIMIS  FAVREHGDFY  ..PFDGPGNV  LAHAYAPG.P
Stromelysin 2 RL........  YEGEADIMIS  FAVKEHGDFY  ..SFDGPGHS  LAHAYPPG.P
Stromelysin 3 EV........  HEGRADIMID  FARYWDGDDL  ..PFDGPGGI  LAHAFFPK.T
Collagenase 1 KV........  SEGQADIMIS  FVRGDHRDNS  ..PFDGPGGN  LAHAFQPG.P
Collagenase 2 RI........  SQGEADINIA  FYQRDHGDNS  ..PFDGPNGI  LAHAFQPG.Q
Collagenase 3 RL........  HDGIADIMIS  FGIKEHGDFY  ..PFDGPSGL  LAHAFPPG.P
MMP12         KI........  NTGMADILVV  FARGAHGDFH  ..AFDGKGGI  LAHAFGPG.S
MMP18         EVQ.......  A.GAADIRLS  .FHGRQSSYC  SNTFDGPGRV  LAHADIPE.L
mt1MMP        EVPYAYIREG  HEKQADIMIF  FAEGFHGDST  ..PFDGEGGF  LAHAYFPG.P
mt2MMP        EVPYEDIRLR  RQKEADIMVL  FASGFHGDSS  ..PFDGTGGF  LAHAYFPG.P
mt3MMP        EVPYSELENG  K.RDVDIPII  FASGFHGDSS  ..PFDGEGGF  LAHAYFPG.P
mt4MMP        EV........  AGSTADIQID  FSKADHNDGY  ..PFDARRHR  .AHAFFPGHH
Consensus     EV--------  -EGEADIMIS  FARGEHGD-Y  --PFDGPGG-  LAHAFFPG-P 251                                                        300
MMP19         ...GEAHFDQ  DERWSLSR..  ..........  ..........  ..........
Matrilysin    GLGGDAHFDE  DERWTDGSSL  ..........  ..........  ..........
Gelatinase A  GVGGDSHFDD  DELWTLGEGQ  VVRVKYGNAD  GEYCKFPFLF  NGKEYNSCTD
Gelatinase B  GIQGDAHFDD  DELWSLGKGV  VVPTRFGNAD  GAACHFPFIF  EGRSYSACTT
Stromelysin 1 GINGDAHFDD  DEQWTKDTT.  ..........  ..........  ..........
Stromelysin 2 GLYGDIHFDD  DEKWTEDAS.  ..........  ..........  ..........
Stromelysin 3 HREGDVHFDY  DETWTIG...  ..........  ..........  ..........
Collagenase 1 GIGGDAHFDE  DERWTNNFR.  ..........  ..........  ..........
Collagenase 2 GIGGDAHFDA  EETWTNTSA.  ..........  ..........  ..........
Collagenase 3 NYGGDAHFDD  DETWTSSSK.  ..........  ..........  ..........
MMP12         GIGGDAHFDE  DEFWTTHSG.  ..........  ..........  ..........
MMP18         ...GSVHFDE  DEFWTEGT..  ..........  ..........  ..........
mt1MMP        NIGGDTHFDS  AEPWTVRNE.  ..........  ..........  ..........
mt2MMP        GLGGDTHFDA  DEPWTFSST.  ..........  ..........  ..........
mt3MMP        GIGGDTHFDS  DEPWTLGNP.  ..........  ..........  ..........
mt4MMP        HTAGYTHFND  DEAWTFRSS.  ..........  ..........  ..........
Consensus     GIGGDAHFDD  DE-WT-GS--  ----------  ----------  ----------
```

FIG.5C

```
              301                                                      350
MMP19         ..........  ..........  ..........  ..........  ..........
Matrilysin    ..........  ..........  ..........  ..........  ..........
Gelatinase A  TGRSDGFLWC  STTYNFEKDG  KYGFCPHEAL  FTMGGNAEGQ  PCKFPFRFQG
Gelatinase B  DGRSDGLPWC  STTANYDTDD  RFGFCPSERL  YTRDGNADGK  PCQFPFIFQG
Stromelysin 1 ..........  ..........  ..........  ..........  ..........
Stromelysin 2 ..........  ..........  ..........  ..........  ..........
Stromelysin 3 ..........  ..........  ..........  ..........  ..........
Collagenase 1 ..........  ..........  ..........  ..........  ..........
Collagenase 2 ..........  ..........  ..........  ..........  ..........
Collagenase 3 ..........  ..........  ..........  ..........  ..........
MMP12         ..........  ..........  ..........  ..........  ..........
MMP18         ..........  ..........  ..........  ..........  ..........
mt1MMP        ..........  ..........  ..........  ..........  ..........
mt2MMP        ..........  ..........  ..........  ..........  ..........
mt3MMP        ..........  ..........  ..........  ..........  ..........
mt4MMP        ..........  ..........  ..........  ..........  ..........
Consensus     ----------  ----------  ----------  ----------  ----------

351                                                      400
MMP19         ..........  ..........  ..........  ..........  ..........
Matrilysin    ..........  ..........  ..........  ..........  ..........
Gelatinase A  TSYDSCTTEG  RTDGYRWCGT  TEDYDRDKKY  GFCPETAMST  V.GGNSEGAP
Gelatinase B  QSYSACTTDG  RSDGYRWCAT  TANYDRDKLF  GFCPTRADST  VMGGNSAGEL
Stromelysin 1 ..........  ..........  ..........  ..........  ..........
Stromelysin 2 ..........  ..........  ..........  ..........  ..........
Stromelysin 3 ..........  ..........  ..........  ..........  ..........
Collagenase 1 ..........  ..........  ..........  ..........  ..........
Collagenase 2 ..........  ..........  ..........  ..........  ..........
Collagenase 3 ..........  ..........  ..........  ..........  ..........
MMP12         ..........  ..........  ..........  ..........  ..........
MMP18         ..........  ..........  ..........  ..........  ..........
mt1MMP        ..........  ..........  ..........  ..........  ..........
mt2MMP        ..........  ..........  ..........  ..........  ..........
mt3MMP        ..........  ..........  ..........  ..........  ..........
mt4MMP        ..........  ..........  ..........  ..........  ..........
Consensus     ----------  ----------  ----------  ----------  ----------
```

FIG.5D

```
              401                                                      450
MMP19         ..........  ..........  ..........  ..........  ...RRGRNLF
Matrilysin    ..........  ..........  ..........  ..........  .....GINFL
Gelatinase A  CVFPFTFLGN  KYESCTSAGR  SDGKMWCATT  ANYDDDRKWG  FCPDQGYSLF
Gelatinase B  CVFPFTFLGK  EYSTCTSEGR  GDGRLWCATT  SNFDSDKKWG  FCPDQGYSLF
Stromelysin 1 ..........  ..........  ..........  ..........  .....GTNLF
Stromelysin 2 ..........  ..........  ..........  ..........  .....GTNLF
Stromelysin 3 ..........  ..........  ..........  ..........  ..DDQGTDLL
Collagenase 1 ..........  ..........  ..........  ..........  .....EYNLH
Collagenase 2 ..........  ..........  ..........  ..........  .....NYNLF
Collagenase 3 ..........  ..........  ..........  ..........  .....GYNLF
MMP12         ..........  ..........  ..........  ..........  .....GTNLF
MMP18         ..........  ..........  ..........  ..........  ...YRGVNLR
mt1MMP        ..........  ..........  ..........  ..........  ..DLNGNDIF
mt2MMP        ..........  ..........  ..........  ..........  ..DLHGNNLF
mt3MMP        ..........  ..........  ..........  ..........  ..NHDGNDLF
mt4MMP        ..........  ..........  ..........  ..........  ..DAHGMDLF
Consensus     ----------  ----------  ----------  ----------  -----GYNLF 451                                                      500
MMP19         VVLAHEIGHT  LGLTHSPAPR  ALMAPYYKR.  LG..RDALLS  WDDVLAVQSL
Matrilysin    YAATHELGHS  LGMGHSSDPN  AVMYPTYGN.  .GDPQNFKLS  QDDIKGIQKL
Gelatinase A  LVAAHEFGHA  MGLEHSQDPG  ALMAPIY...  .TYTKNFRLS  QDDIKGIQEL
Gelatinase B  LVAAHEFGHA  LGLDHSSVPE  ALMYPMY...  .RTFEGPPLH  KDDVNGIRHL
Stromelysin 1 LVAAHEIGHS  LGLFHSANTE  ALMYPLYHS.  LTDLTRFRLS  QDDINGIQSL
Stromelysin 2 LVAAHELGHS  LGLFHSANTE  ALMYPLYNS.  FTELAQFRLS  QDDVNGIQSL
Stromelysin 3 QVAAHEFGHV  LGLQHTTAAK  ALMSAFY.T.  FRYP..LSLS  PDDCRGVQHL
Collagenase 1 RVAAHELGHS  LGLSHSTDIG  ALMYPSY.T.  F..SGDVQLA  QDDIDGIQAI
Collagenase 2 LVAAHEFGHS  LGLAHSSDPG  ALMYPNY.A.  FRETSNYSLP  QDDIDGIQAI
Collagenase 3 LVAAHEFGHS  LGLDHSKDPG  ALMFPIY.T.  YTGKSHFMLP  DDDVQGIQSL
MMP12         LTAVHEIGHS  LGLGHSSDPK  AVMFPTY.K.  YVDINTFRLS  ADDIRGIQSL
MMP18         IIAAHEVGHA  LGLGHSRYSQ  ALMAPVYEG.  YR..PHFKLH  PDDVAGIQAL
mt1MMP        LVAVHELGHA  LGLEHSSDPS  AIMAPFY.Q.  WMDTENFVLP  DDDRRGIQQL
mt2MMP        LVAVHELGHA  LGLEHSSNPN  AIMAPFY.Q.  WKDVDNFKLP  EDDLRGIQQL
mt3MMP        LVAVHELGHA  LGLEHSNDPT  AIMAPFY.Q.  YME.QTLQLP  NDDYR..HQR
mt4MMP        AVAVHEFGHA  IGLSHVAAAH  SIMRPYYQGP  VGDPLRYGLP  YEDKVRVWQL
Consensus     LVAAHE-GH-  LGL-HSSDP-  ALM-P-Y---  --D--NF-LS  QDDIRGIQSL
```

FIG.5E

```
              501                                                      550
MMP19         YGKPLGGSVA VQLPGKLF.. .......... .......... ..........
Matrilysin    YGKR...SNS RKK*...... .......... .......... ..........
Gelatinase A  YGAS...PDI D......... .......... .......... ..........
Gelatinase B  YGPR...PEP EPRPPTTTTP QPTAPPTVCP TGPPTVHPSE RPTAGPTGPP
Stromelysin 1 YGPP...PDS PETP...... .......... .......... ..........
Stromelysin 2 YGPP...PAS TEEP...... .......... .......... ..........
Stromelysin 3 YG........ .QPWPTVTSR .......... ....TPALGP QAGIDTNEIA
Collagenase 1 YGRS...QNP VQ........ .......... .......... ..........
Collagenase 2 YGLS...SNP IQ........ .......... .......... ..........
Collagenase 3 YGPG...DED PN........ .......... .......... ..........
MMP12         YGDP...KEN QRLP...... .......... .......... ..........
MMP18         YGKK...SPV IRDEEEEE.. .......... .......... ..........
mt1MMP        YGGESGFPTK MPPQPRTTSR .......... ......PSVPD KPKNPT....
mt2MMP        YGTPDGQPQP TQPLPTVTPR RPGRPDHRPP RPPQPPPPGG KPERPPKPGP
mt3MMP        YMSPDKIPPP TRPLPTVPPH R......... .....SIPPA DPRKNDRPKP
mt4MMP        YGVRESVSPT AQP....... .......... .......... ..........
Consensus     YG-P---P-P -QPPP----- ---------- ---------- ----------

551                                                      600
MMP19         ....TDFETW DSYSPQGRRP ETQGPKYCHS SFDAITVDRQ QQLYIFGSH
Matrilysin    .......... .......... .......... .......... .........
Gelatinase A  .LGTGPTPTL GPVTPEICKQ DIV....... .FDGIAQ.IR GEIFFFKDRF
Gelatinase B  SAGPTGPPTA GPSTATTVPL SPVDDACNVN IFDAIAE.IG NQLYLFKDGK
Stromelysin 1 .LVPTEPVPP EPGTPANCDP AL........ SFDAVST.LR GEILIFKDRH
Stromelysin 2 .LVPTKSVPS GSEMPAKCDP AL........ SFDAIST.LR GEYLFFKDRY
Stromelysin 3 PLEPDA.... ...PPDACEA S......... .FDAVST.IR GELFFFKAGF
Collagenase 1 ........PI GPQTPKACDS KL........ TFDAITT.IR GEVMFFKDRF
Collagenase 2 ........PT GPSTPKPCDP SL........ TFDAITT.LR GEILFFKDRY
Collagenase 3 ........PK HPKTPDKCDP SL........ SLDAITS.LR GETMIFKDRF
MMP12         ........NP DNSEPALCDP NL........ SFDAVTT.VG NKIFFFKDRF
MMP18         ....TELPT. ...VPPVPTE PSPMPDPCSS ELDAMMLGPR GKTYAFKGDY
mt1MMP        .......... ..YGPNICDG N......... .FDTVAM.LR GEMFVFKKRW
mt2MMP        PVQPRATERP DQYGPNICDG D......... .FDTVAM.LR GEMFVFKGRW
mt3MMP        PRPPTGRPSY PGAKPNICDG N......... .FNTLAI.LR REMFVFKDQW
mt4MMP        ..EEPPLLPE PPDNRSSAPP RKDVPHRCST HFDAVA.QIR GEAFFFKGKY
Consensus     ---PT---P- GP-TP--CDP -L-------- SFDAIAT-LR GE-FFFKDRF
```

FIG.5F

```
              601                                                      650
MMP19         FWEVAADGNV SEPRP..LQE RWVGLP...P NIEAAAVSLN DGDFYFFKGG
Matrilysin    .......... .......... .......... .......... ..........
Gelatinase A  IWRTVTPRD. KPMGPLLVAT FWPELP...E KIDAVYEAPQ EEKAVFFAGN
Gelatinase B  YWRFSEGRGS RPQGPFLIAD KWPALP...R KLDSVFEEPL SKKLFFFSGR
Stromelysin 1 FWRKSLRKLE PELH..LISS FWPSLP...S GVDAAYEVTS KDLVFIFKGN
Stromelysin 2 FWRRSHWNPE PEFH..LISA FWPSLP...S YLDAATEVNS RDTVFIFKGN
Stromelysin 3 VWRLRGGQLQ PGY.PALASR HWQGLP...S PVDAAFE.DA QGHIWFFQGA
Collagenase 1 YMRTNPFYPE VELN..FISV FWPQLP...N GLEAAYEFAD RDEVRFFKGN
Collagenase 2 FWRRHPQLQR VEMN..FISL FWPSLP...T GIQAAYEDFD RDLIFLFKGN
Collagenase 3 FWRLHPQQVD AELF..LTKS FWPELP...N RIDAAYEHPS HDLIFIFRGR
MMP12         FWLKVSERPK TSVN..LISS LWPTLP...S GIEAAYEIEA RNQVFLFKDD
MMP18         VWTVSDSGPG PLFR...VSA LWEGLP...G NLDAAVYSPR TQWIHFFKGD
mt1MMP        FWRVRNNQVM DGY.PMPIGQ FWRGLP...A SINTAYE.RK DGKFVFFKGD
mt2MMP        FWRVRHNRVL DNY.PMPIGH FWRGLP...G DISAAYE.RQ DGRFVFFKGD
mt3MMP        FWRVRNNRVM DGY.PMQITY FWRGLP...P SIDAVYE.NS DGNFVFFKGN
mt4MMP        FWRLTRDRHL VSLQPAQMHR FWRGLPLHLD SVDAVYERTS DHKIVFFKGD
Consensus     FWRV---R-- -E--P-LIS- FWPGLP---- -IDAAYE--S D--IFFFKGN 651                                                      700
MMP19         RCWRFRGPKP VWGLPQLCR. ...AGGLPRH PDAALFF.PP LRRLILFKGA
Matrilysin    .......... .......... .......... .......... ..........
Gelatinase A  EYWIY.SAST LERGYPKPLT SLGLPPDVQR VDAAF.NWSK NKKTYIFAGD
Gelatinase B  QVWVYTGASV LG...PRRLD KLGLGADVAQ VTGAL..RSG RGKMLLFSGR
Stromelysin 1 QFWAIRGNEV RAGYPRGIHT .LGFPPTVRK IDAAI.SDKE KNKTYFFVED
Stromelysin 2 EFWAIRGNEV QAGYPRGIHT .LGFPPTIRK IDAAV.SDKE KKKTYFFAAD
Stromelysin 3 QYWVYDGEKP VLG.PAPL.T EL..GLVRFP VHAALVWGPE KNKIYFFRGR
Collagenase 1 KYWAVQGQNV LHGYPKDIYS SFGFPRTVKH IDAAL.SEEN TGKTYFFVAN
Collagenase 2 QYWALSGYDI LQGYPKDI.S NYGFPSSVQA IDAAV.F..Y RSKTYFFVND
Collagenase 3 KFWALNGYDI LEGYPKKI.S ELGLPKEVKK ISAAV.HFED TGKTLLFSGN
MMP12         KYWLISNLRP EPNYPKSIHS .FGFPNFVKK IDAAV.FNPR FYRTYFFVDN
MMP18         KVWRYINFKM SPGFPK..K. ...LNRSEPN LDAALYW.PL NQKVFLFKGS
mt1MMP        KHWVFDEASL EPGYPKHI.K ELGRGLPTDK IDAALFWMPN .GKTYFFRGN
mt2MMP        RYWLFREANL EPGYPQPL.T SYGLGIPYDR IDTAIWWEPT .GHTFFFQED
mt3MMP        KYWVFKDTTL QPGYPHDL.I TLGSGIPPHG IDSAIWWEDV .GKTYFFKGD
mt4MMP        RYWVFKDNNV EEGYPRPVS. ..DFSLPPGG IDAAFSW.AH NDRTYFFKDQ
Consensus     KYW-F-G--V LPGYPK-I-T -LGFP--V-K IDAAL-W-P- -GKTYFF-GD
```

FIG.5G

```
              701                                                        750
MMP19         RYY...VLAR  GGLQVEPYYP  RSLQD.WGGI  PEEVSGALPR  PDGSIIFFRD
Matrilysin    ..........  ..........  ..........  ..........  ..........
Gelatinase A  KFWRYNEVKK  K...MDPGFP  KLIADAWNAI  PDNLDAVVDL  QGGGHSYFFK
Gelatinase B  RLWRFDVKAQ  M...VDPRSA  SEVDRMFPGV  P..LDTHDVF  QYREKAYFCQ
Stromelysin 1 KYWRFDEKRN  S...MEPGFP  KQIAEDFPGI  DSKIDAVF.E  EFGFFYFFTG
Stromelysin 2 KYWRFDENSQ  S...MEQGFP  RLIADDFPGV  EPKVDAVL.Q  AFGFFYFFSG
Stromelysin 3 DYWRFHPSTR  R...VDSPVP  RRATDWRGVP  SEIDAAFQDA  D.GYAYFLRG
Collagenase 1 KYWRYDEYKR  S...MDPGYP  KMIAHDFPGI  GHKVDAVF.M  KDGFFYFFHG
Collagenase 2 QFWRYDNQRQ  F...MEPGYP  KSISGAFPGI  ESKVDAVF.Q  QEHFFHVFSG
Collagenase 3 QVWRYDDTNH  I...MDKDYP  RLIEEDFPGI  GDKVDAVY.E  KNGYIYFFNG
MMP12         QYWRYDERRQ  M...MDPGYP  KLITKNFQGI  GPKIDAVFYS  KNKYYYFFQG
MMP18         GYWQWDELAR  TDF...SSYP  KPIKGLFTGV  PNQPSAAMSW  QDGRVYFFKG
mt1MMP        KYYRFNEELR  A...VDSEYP  KNIKVWEGIP  ESPRGSFMGS  DEVFTYFYKG
mt2MMP        RYWRFNEETQ  R...GDPGYP  KPISVWQGIP  ASPKGAFLSN  DAAYTYFYKG
mt3MMP        RYWRYSEEMK  T...MDPGYP  KPITVWKGIP  ESPQGAFVHK  ENGFTYFYKE
mt4MMP        LYWRYDDHTR  ...HMDPGYP  AQ.SPLWRGV  PSTLDDAMRW  SDGASYFFRG
Consensus     KYWRYDE--R  ----MDPGYP  K-I---FPGI  PSKVDAV---  --GF-YFF-G 751                                                        800
MMP19         DRYWRLDQAK  LQATTSGRWA  TELPWMGCWH  ..........  ..ANSGSALF
Matrilysin    ..........  ..........  ..........  ..........  ..........
Gelatinase A  GAYY.LKLEN  QS.LKSV.KF  ...GSIKSDW  LGC*......  ..........
Gelatinase B  DRFY.WRVSS  RSELNQVDQV  ...GYVTYDI  LQCPED*...  ..........
Stromelysin 1 SSQLEFDPNA  KKVTHTLKSN  ...SWLNC*.  ..........  ..........
Stromelysin 2 SSQFEFDPNA  RMVTHILKSN  ...SWLHC*.  ..........  ..........
Stromelysin 3 RLYWKEDPVK  VKALEGFPRL  VCPDFFGCAE  PANTFL*...  ..........
Collagenase 1 TRQYKFDPKT  KRILTLQKAN  ...SWFNCRK  N*........  ..........
Collagenase 2 PRYYAFDLIA  QRVTRVARGN  ...KWLNCRY  G*........  ..........
Collagenase 3 PIQFEYSIWS  NRIVRVMPAN  ...SILWC*.  ..........  ..........
MMP12         SNQFEYDFLL  QRITKTLKSN  ...SWFGC*.  ..........  ..........
MMP18         KVYWRLNQ.Q  LRVEKGYPRN  ISHNWMHCRP  RTIDTTPSGG  NTTPSGTGIT
mt1MMP        NKYWKFNNQK  LKVEPGYPKS  ALRDWMGC..  ..........  ..........
mt2MMP        TKYWKFDNER  LRMEPGYPKS  ILRDFMGCQE  HVEPGPRWPD  VARPPFNPHG
mt3MMP        GVLEIQTTRY  SRLEPGHPRS  ILKDLSGCD.  ..........  ..........
mt4MMP        QEYWKVLDGE  LEVAPGYPQS  TARDWLVCGD  SQADGSVAAG  VDAAEGPRAP
Consensus     --YWKFD---  LRVT-G-P-N  ----WLGC--  ----------  ----------
```

FIG. 5H

```
                 801                                                       850
MMP19            *.........  ..........  ..........  ..........  ..........
Matrilysin       ..........  ..........  ..........  ..........  ..........
Gelatinase A     ..........  ..........  ..........  ..........  ..........
Gelatinase B     ..........  ..........  ..........  ..........  ..........
Stromelysin 1    ..........  ..........  ..........  ..........  ..........
Stromelysin 2    ..........  ..........  ..........  ..........  ..........
Stromelysin 3    ..........  ..........  ..........  ..........  ..........
Collagenase 1    ..........  ..........  ..........  ..........  ..........
Collagenase 2    ..........  ..........  ..........  ..........  ..........
Collagenase 3    ..........  ..........  ..........  ..........  ..........
MMP12            ..........  ..........  ..........  ..........  ..........
MMP18            LDTTLSATET  TFEY*.....  ..........  ..........  ..........
mt1MMP           ...PSGGRPD  EGTEEEETEVI IIEVDEEGGG  ..........  .AVSAAAVVL
mt2MMP           GAEPGADSAE  GDVGDGDGDF  GAGVNKDGGS  RVVVQMEEVA  RTVNVVMVLV
mt3MMP           ..GPTDRVKE  GHSPPDDVDI  VIKLDNTAS.  ..........  .TVKAIAIVI
mt4MMP           PDQHDQSRSE  DGYEVCSCTS  GASSPPGAPG  PLVAATMLLL  LPPLSPGALW
Consensus        ----------  ----------  ----------  ----------  ----------

851                                               889
MMP19            ..........  ..........  ..........  .........
Matrilysin       ..........  ..........  ..........  .........
Gelatinase A     ..........  ..........  ..........  .........
Gelatinase B     ..........  ..........  ..........  .........
Stromelysin 1    ..........  ..........  ..........  .........
Stromelysin 2    ..........  ..........  ..........  .........
Stromelysin 3    ..........  ..........  ..........  .........
Collagenase 1    ..........  ..........  ..........  .........
Collagenase 2    ..........  ..........  ..........  .........
Collagenase 3    ..........  ..........  ..........  .........
MMP12            ..........  ..........  ..........  .........
MMP18            ..........  ..........  ..........  .........
mt1MMP           PVLLLLLVLA  VGLAVFFFRR  HGTPRRLLYC  QRSLLDKV*
mt2MMP           PLLLLLCVLG  LTYALVQMQR  KGAPRVLLYC  KRSLQEWV*
mt3MMP           PCILALCLLV  LVYTVFQFKR  KGTPRHILYC  KRSMQEWV*
mt4MMP           TAAQALTL*.  ..........  ..........  .........
Consensus        ----------  ----------  ----------  ---------
```

FIG. 51

HUMAN MATRIX METALLOPROTEASE GENE, PROTEINS ENCODED THEREFROM AND METHODS OF USING SAME

This is a Continuation-in-Part of U.S. application Ser. No. 08/814,394 filed Mar. 11, 1997, now abandoned.

BACKGROUND OF THE INVENTION

1. Field of the Invention

The present invention relates generally to therapeutic and diagnostic agents in cancer and inflammatory diseases. More specifically, the present invention relates to polynucleotide sequences encoding matrix metalloprotease proteins, as well as methods which utilize these sequences, which are useful for the detection, diagnosis, staging, monitoring, prognosis, prevention, or treatment of cancer or inflammatory diseases.

2. Description of the Related Art

The matrix metalloproteases (MMPs) are a multi-enzyme family capable of completely degrading the components of the extracellular matrix (ECM), their natural substrates (W. B. Ennis, and L. M. Matrisian, *J. Neuro-Oncology*, 18: 105–109 (1994)). The ECM is a meshwork of cells and various types of collagens and proteoglycans, collectively called connective tissue, which provides mechanical support and helps to maintain the structural integrity of tissues and organs. The function of the ECM is particularly apparent in articular cartilage where it provides cushioning and ease of movement between bones in joints. The MMPs are secreted by the cellular components of the ECM (fibroblasts, chondrocytes and synoviocytes) and inflammatory cells (neutrophils and macrophages) in inactive forms (zymogens) which are converted extracellularly to the active enzymes by various proteinases. Normally MMPs function in a highly regulated fashion as part of the physiological turnover of the ECM, effectively renewing and remodeling the ECM. However, in the clinical features of several diseases, the ECM is degraded and there is much evidence to support that MMPs play a significant pathological role in ECM degradation.

At least fourteen members of the MMP family have been identified and most assigned EC numbers; several more have been discovered recently. They can be classified generally according to four subgroups based on substrate preference or cellular localization; e.g., collagenases prefer Type I and II collagen, gelatinases prefer Type IV collagen, and stromelysins prefer proteoglycans (L. M. Matrisian, *Bio. Essays* 14: 455–463 (1992)). The fourth subgroup are the membrane type MMPs (mtMMPs) which are characterized by the presence of a hydrophobic transmembrane domain near the C-terminus for anchoring the protein in the cell membrane. All of the other MMPs are secreted into the extracellular milieu.

Most of the known MMPs contain zinc in their catalytic sites and require calcium for activity. The major human MMPs have been cloned and exhibit greater than 50% homology. They contain a leader sequence for signaling their secretion by cells; a highly conserved pro-enzyme sequence removed upon activation; a catalytic site with a highly conserved zinc binding domain; and a carboxy terminal region containing a conserved sequence similar to hemopexin, a heme binding protein. Although MMPs can be readily activated in vitro using mercurial compounds or trypsin, the precise mechanism for propeptide removal and activation of MMPs in vivo is not understood. Some MMPs can undergo an autoactivation process, while recent evidence indicates that membrane type MMPs may function as activators of other MMPs.

A growing line of evidence implicates the MMPs as important enzymes in cancer metastasis. Although different cancer cell lines have been shown to express various MMPs when grown in culture, gelatinase A in particular has been the focus of a number of recent studies which demonstrates its role in the invasiveness of cancer cells (W. G. Stetler-Stevenson, et al., *FASEB J*. 7: 1434–1441 (1993)). For example, gelatinase A is found in the urine of bladder cancer patients and specific monoclonal antibodies have been used to detect the enzyme in breast tumor sections (I. M. Margulies, et al., 1: 467–474 (1992)). The enzyme is expressed in an invasive prostate cancer cell line (PC-3 ML) and cells transfected with the gelatinase A gene are capable of extravasation when injected into mice (M. E. Stearns, and M. Wang, *Oncology Res*. 6: 195–201 (1994)). These studies and others implicate the involvement of gelatinase A in tumor metastasis, and suggest that inhibitors of this enzyme may offer therapeutic potential in certain forms of cancer. A broad spectrum matrix metalloproteinase inhibitor has been shown to decrease the tumor burden of mice bearing ovarian carcinoma xenographs (B. Davies, et al., *Cancer Res*. 53: 2087–2091 (1993)). This compound (BB-94, batimastat) is currently being evaluated in clinical trials for malignant ascites (S. A. Watson, et al., *Cancer Research*, 55: 3629–3633 (1995)); however, its poor bioavailability necessitates parental administration. Gelatinase A selective succinyl hydroxamates have been suggested as anti-cancer agents as well, yet these compounds possess the same peptidic backbone as batimastat (Porter, J. R.; Beeley, N. R. A.; Boyce, B. A.; Mason, B.; Millican, A.; Millar, K.; Leonard, J.; Morphy, J. R.; O'Connell, J. P. Potent and selective inhibitors of gelatinase A 1. Hydroxamic acid derivatives. *Bioorg. Med. Chem. Lett*., 4: 2741–2746 (1994)). More recently, an orally active, broad spectrum, MMP inhibitor (BB-2516, marimastat) was reported to stop progression of colorectal, ovarian, prostatic and pancreatic cancer (R. P. Beckett, et al., *D. D. T*., 1: 16–26 (1996)).

Several lines of evidence indicate that the unregulated activity of MMPs is responsible for the joint degradation observed in rheumatoid arthritis and osteoarthritis. In these human arthritides, activated forms of the MMPs and their products (glycosaminoglycans and collagen fragments) are found in synovial fluids and joint tissues in abnormally high amounts (see E. D. Harris Jr., Role of collagenase in joint destruction. *The Joints and Synovial Fluid*, Vol., 1, Sokologg, L., Ed., Orlando, Fla., Academic Press, 1977, T. E. Cawston, et al., *Arthritis Rheum*., 27: 285–290 (1984), Cawston, T. *Ann. Rheumatic Diseases*., 52: 769–770 (1993), Y. L. Okada, et al., *J. Biol. Chem*., 261: 14245–14255 (1986), D. L. Scott, et al., *Molec. Aspects Med*., 12: 341–394 (1991), and E. D. Harris, et al., *Arthritis Rheum*., 12: 92–102 (1992)). These arthritic tissues also show a greater-than-normal expression of MMPs (S. S. McCachren, *Arthritis and Rheumatism*, 34: 1085–1093 (1991), A. J. P. Docherty and G. Murphy, *Ann. Rheumat. Dis*., 49: 469–479 (1990)) which is induced by cytokines and growth factors, also found abundantly in these tissues (D. L. Scott, et al., (1991), supra, S. M. Frisch and H. E. Ruley, *J. Biol. Chem*., 262: 16300–16304 (1987)). In addition, the activities of MMPs in normal tissues are thought to be regulated by the presence of endogenous tissue inhibitors of MMPs, (TIMPs, see T. E. Cawston, *Curr. Med. Lit. Rheum*., 3: 127–0 (1984)). The ratio of the amounts of TIMP and MMPs is thought to maintain a balance between the rates of degradation and synthesis of ECM. In tissues from rheumatoid arthritics, an abnormally high expression of MMPs results in an imbalance of these enzymes and degradation of ECM (S. S.

McCachren (1991) and T. E. Cawston (1984), supra). Thus in arthritis, inhibition of the exacerbated degradative activities of MMPs by specific agents could help restore this balance. In rodent models which mimic the biochemical features of arthritis, there is evidence that the combined action of proteoglycan loss (due to stromelysin activity) and cartilage degradation (due to collagenase) are early events in this disease (R. M. Hembry, et al., *Am. J. Pathol.*, 143: 628–642 (1993), K. A. Hasty, et al., *Arthritis and Rheumatism*, 33: 388–397 (1990)). Several prototype inhibitors of MMPs have been shown to reduce cartilage degradation in these animal models (M. J. DiMartino, et al., *J. Cell Biochem. suppl.*, 19E: 179 (1991), P. Brown, et al., Orally active inhibitors of cartilage degradation. Abst. # 81, Abstracts of Inflammation '93, Vienna, Austria, p. 29. (1993)).

There is much evidence to suggest that MMPs mediate the migration of inflammatory cells into endothelium (D., Moscatelli and D. B. Rifkin, *Biochim. Biophys. Acta.*, 948: 67–85 (1988), P. Zaoui, et al., Matrix metalloproteases (MMP) exocytosis from neutrophils is inhibited by endothelial adhesion. Abst. # 83, Abstracts of Inflammation '93, Vienna, Austria, p. 29 (1993)) participating in periodontal diseases (H. Birkedal-Hansen, *J. Peridontol.*, 64: 474–484 (1993)) and facilitating the growth of atherosclerotic plaques (A. M. Henny, et al., *Proc. Natl. Acad. Sci.*, 8: 8154–8158 (1991)). Recently, gelatinase-A was reported to promote cleavage of the amyloid protein precursor which would suggest a role in Alzheimers disease for this MMP (N. Peress, et al., *J. Neuropathol. Exp. Neurol.*, 54: 16–22 (1995), R. N. Lipage, et al., *FEBS Lett.*, 377: 267–270 (1995)). Thus, there is compelling evidence that MMPs play an important role in arthritis and other inflammatory diseases and that targeted inhibition of these proteinases by pharmaceutical agents could have beneficial effects.

It would be advantageous to provide specific methods and reagents for the diagnosis, staging, prognosis, monitoring, prevention or treatment of diseases and conditions associated with imbalances in the production or activity of MMPs or to indicate possible predisposition to these conditions. Such methods would include assaying a test sample for products of the gene. Such methods would comprise making cDNA from mRNA in the test sample, amplifying (when necessary) portions of the cDNA corresponding to the gene or a fragment thereof, and detecting the cDNA product as an indication of the presence of the cancer; or detecting translation products of the mRNAs comprising gene sequences as an indication of the presence of the disease. These reagents include polynucleotide(s), or fragment(s) thereof which may be used in diagnostic methods such as reverse transcriptase-polymerase chain reaction (RT-PCR), PCR, or hybridization assays of biopsied tissue; or proteins which are the translation products of such mRNAs; or antibodies directed against these proteins. Such assays would include methods for assaying a sample for product(s) of the gene and detecting the product(s) as an indication of disease. Drug treatment or gene therapy for conditions or diseases associated with these detected diseases and conditions then can be based on these identified gene sequences or their expressed proteins, and efficacy of any particular therapy can be monitored using the diagnostic methods disclosed herein.

Studies to understand the role of MMPs in tumor growth, metastases, or inflammatory conditions and diseases such as arthritis and their potential as a therapeutic or diagnostic tools are limited to previously described MMP proteins. It would be advantageous to identify novel human MMPs which may be directly involved in the physiology of, for example, tumor growth, extravasation, or invasion. Isolation of DNA sequences encoding human MMPs would permit more extensive studies on the association and regulation of individual MMPs in specific cancers or tumor types, and in diseases such as arthritis or other inflammatory conditions. In addition, the identification of tissue-specific or disease-specific MMPs would provide more direct targets for therapeutics designed to attenuate these diseases.

SUMMARY OF THE INVENTION

This present invention provides an isolated and purified polynucleotide encoding a matrix metalloprotease (provisionally named MMP-ABT), polynucleotide fragments thereof, expression vectors containing those polynucleotides, host cells transformed with those expression vectors, processes for making the MMP-ABT protein using those polynucleotides and vectors, isolated and purified MMP-ABT protein and polypeptide fragments thereof, and antibodies raised to synthetic peptides derived from the MMP-ABT protein. The invention also provides diagnostic assays to identify the presence of the MMP-ABT polynucleotide or polypeptide, assays used to identify agents that affect the function of the MMP-ABT polynucleotide or polypeptide, and the use as therapeutic agents of the MMP-ABT polynucleotide, polypeptides, or antibodies.

The cDNA clone was obtained by screening a human cDNA expression database with a consensus sequence to twelve other human MMPs. The sequence of the partial cDNA isolated indicated that the gene product is a novel MMP protein that is expressed in a limited number of tissues.

BRIEF DESCRIPTION OF THE DRAWINGS

FIG. 1 shows the MMP-ABT consensus sequence used to query the LifeSeq™ database. The functional motifs present in all MMPs are double underlined.

FIG. 2 shows the complete nucleotide and translated sequence (frame 3) of EST #907334 in LifeSeq™. A putative cysteine switch motif (PRCGVTD which is SEQ ID NO:8) and a putative furin recognition site (RKKR which is SEQ ID NO:9) are double underlined.

FIGS. 4A–4D show the doubled stranded complete nucleotide sequence (SEQ ID NO:1 and SEQ ID NO:2, top and bottom strand respectively) of the MMP-ABT gene and the translated amino acid sequence (SEQ ID NO:10) of MMP-ABT (shown beneath in single letter codes). Indicated in bold type are the structural domains found in other MMPs. The cysteine switch, furin recognition site, and zinc binding site are double underlined. The putative poly adenylation signal in the 3' untranslated region of the mRNA is single underlined. Boxes indicate the position of the 3' end of the primers used in the synthesis of DNA constructs for the expression of the catalytic portion of MMP-ABT.

FIGS. 5A–5I show the alignment of the polypeptide encoded by SEQ ID NO:10 with the amino acid sequences of all known human MMPs, namely, matrilysin (GenBank Accession No. L22524, SEQ ID NO:18), Gelatinase A (GenBank Accession No. M55593, SEQ ID NO:19), Gelatinase B (GenBank Accession No. J05070, SEQ ID NO:20), Stromelysin 1 (GenBank Accession No. J03209, SEQ ID NO:21), Stromelysin 2 (GenBank Accession No. X07820, SEQ ID NO:22), Stromelysin 3, (GenBank Accession No. X57766, SEQ ID NO:23), Collagenase 1 (GenBank Accession No. M 13509, SEQ ID NO:24), Collagenase 2 (GenBank Accession No. J05556, SEQ ID NO:25), Collagenase 3 (GenBank Accession No. X75308, SEQ ID NO:26), MMP12 (GenBank Accession No. L23808, SEQ ID NO:27), MMP18 (GenBank Accession No. Y08622 or X92521, SEQ ID NO:28), mt1MMP (GenBank Accession No. D26512, SEQ ID NO:29), mt2MMP (GenBank Accession No. Z48482, SEQ ID NO:30), mt3MMP (GenBank Accession No. D50477, SEQ ID NO:31), and mt4MMP (GenBank Accession No. X89576, SEQ ID NO:32). The consensus sequence was generated using a plurality of 5. Characteristic motifs found in MMPs are double underlined.

DETAILED DESCRIPTION OF THE INVENTION

Figure 3:
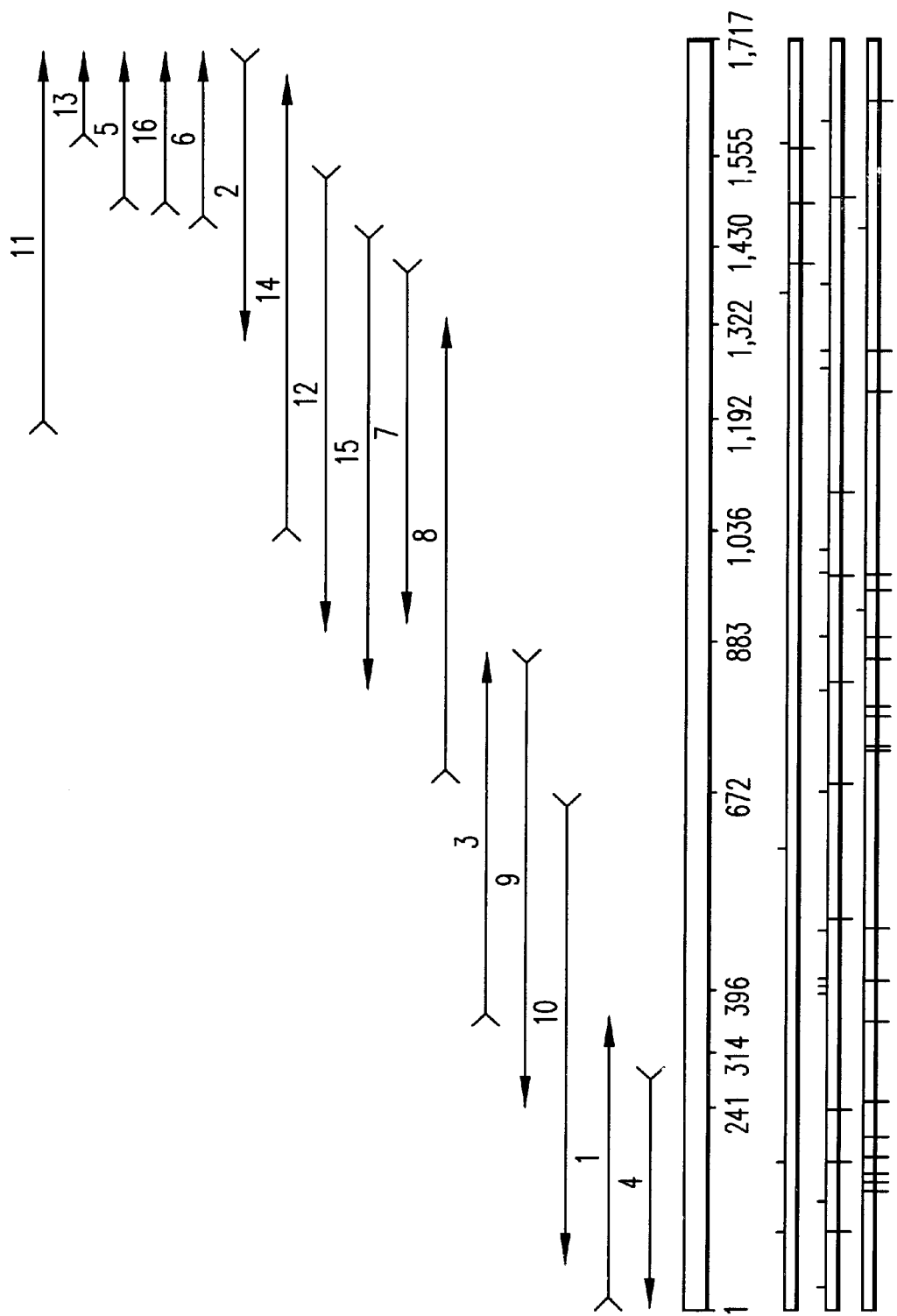
FIG. 3 shows the length and position of individual sequencing reactions to generate the double stranded nucleotide sequence of the insert in clone #907334. The boxes at the bottom are graphic representations of the three forward reading frames with start codons shown as short upward lines and stop codons as longer downward lines. Frame 1 contains the longest open reading frame.

The present invention provides isolated and purified polynucleotides that encode a human matrix metalloprotease, fragments thereof, expression vectors containing those polynucleotides, host cells transformed with those expression vectors, a process of making the MMP-ABT using those polynucleotides and vectors, and isolated and purified recombinant MMP-ABT and polypeptide fragments thereof.

The present invention also provides for the use of MMP-ABT in developing treatments for any disorder mediated (directly or indirectly) by insufficient amounts or production of MMP-ABT protein. Purified human MMP-ABT protein may be administered to a patient with such a condition. Alternatively, gene therapy techniques for producing MMP-ABT polypeptide in vivo are also provided.

The present invention also provides methods for assaying a test sample for products of the MMP-ABT gene, which comprises making cDNA from mRNA in the test sample, and detecting the cDNA as an indication of the presence of the MMP-ABT gene. The method may include an amplification step, wherein portions of the cDNA corresponding to the gene or fragment thereof is amplified. Methods also are provided for assaying for the translation products of mRNAs. Test samples, which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain cDNA sequences in test samples. Also disclosed are nucleic acid sequences, which permit the production of encoded polypeptide sequences, which are useful as standards or reagents in diagnostic immunoassays, targets for pharmaceutical screening assays and/or as components or target sites for various therapies. Monoclonal and polyclonal antibodies directed against at least one epitope contained within these polypeptide sequences are useful for diagnostic tests as well as delivery agents for therapeutic agents and for screening for diseases or conditions associated with cancers, arthritis, or inflammation. Isolation of sequences of other portions of the gene of interest can be accomplished by utilizing probes or PCR primers derived from these nucleic acid sequences, thus allowing additional probes and polypeptides of the genome of interest to be established, which also will be useful in the diagnosis, prognosis and/or treatment of diseases and conditions characterized by the MMP-ABT gene disclosed herein.

The techniques for determining the amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. The techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two amino acid sequences likewise can be compared by determining their "percent identity." The programs available in the Wisconsin Sequence Analysis Package (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of cancer, arthritis, or inflammation resulting from or associated with an MMP-ABT disorder; the information obtained therefrom will aid in the diagnosis, staging, monitoring, prognosis and/or therapy of those same diseases or conditions. Test methods include, for example, probe assays which utilize the sequence(s) provided herein and which also may utilize nucleic acid amplification methods such as the polymerase chain reaction (PCR), the ligase chain reaction (LCR); and hybridization. In addition, the nucleotide sequences provided herein contain open reading frames which encode one or more immunogenic epitopes. Such epitopes are believed to be unique to the disease state or condition associated with MMP-ABT related cancer, arthritis, or inflammation. The uniqueness of any epitope may be determined by its immunological reactivity in diseased tissues and lack of immunological reactivity with non-diseased tissues. Methods for determining immunological reactivity are well-known and include but are not limited to, for example, radioimmunoassay (RIA), enzyme-linked immunosorbent assay (ELISA), hemagglutination (HA), fluorescence polarization immunoassay (FPIA); chemiluminescent immunoassay (CLIA), and others; several examples of suitable methods are described herein.

Unless otherwise stated, the following terms shall have the following meanings:

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide.

An MMP-ABT polynucleotide, as used herein, is defined as follows: For polynucleotides greater than about 100 nucleotides, MMP-ABT polynucleotides encompass polynucleotide sequences encoded by "MMP-ABT variants" in accordance with the definition of those terms, described below. For polynucleotides less than about 100 nucleotides in length, MMP-ABT sequences encompass sequences that "selectively hybridize" to sequences of MMP-ABT or its variants in accordance with the definition of that phrase, given below. Furthermore, MMP-ABT polynucleotides include polynucleotides encoding MMP-ABT polypeptides, as that term is defined below.

"MMP-ABT variants", as used herein, refers to polynucleotides that have at least about at least about 80% and even more preferably, at least about 90% global sequence identity over a length (at least comparable to SEQ ID NO:1) of the polynucleotide sequence, to the MMP-ABT sequences disclosed herein.

"Sequence identity" is determined essentially as follows: Two polynucleotides, one of which is the MMP-ABT polynucleotide and preferably, the full length MMP-ABT sequence, are considered to be identical to each other if, when aligned using the default parameters of the search algorithm BLAST 2.0, the second polynucleotide encodes at least about 90% of the catalytic region of the MMP-ABT polypeptide, and more preferably, at least about 95%. The catalytic region of the MMP-ABT is from about amino acid position 151 to about amino acid position 510 of SEQ ID NO:10. The BLAST 2.0 program is publicly available.

As used herein, a nucleic acid sequence or fragment (such as for example, primers or probes), is considered to selectively hybridize to an MMP-ABT sequence, if such a sequence is capable of specifically hybridizing to an MMP-ABT sequence or a variant thereof (e.g. a probe that hybridizes to MMP-ABT nucleic acid but not to a polynucleotide from other members of the MMP family) or specifically priming a polymerase chain reaction: (i) under typical hybridization and wash conditions, such as those described, for example, in Maniatis, (Molecular Cloning: A Laboratory Manual, 2nd Edition, 1989) where preferred hybridization conditions are those of lesser stringency and more preferred, higher stringency; or (ii) using reduced stringency wash conditions that allow at most about 25–30% basepair mismatches, for example, 2×SSC, 0.1% SDS, at room temperature twice, for 30 minutes each; then 2×SSC, 0.1% SDS, 37 C, once for 30 minutes; the 2×SSC at room temperature twice, 10 minutes each or (iii) under standard PCR conditions such as those described by Saiki, R. K. et al. or under "touch-down" PCR conditions such as described by Roux, K. H., (1994), Biotechiques, 16:812–814).

"A sequence corresponding to a cDNA" means that the sequence contains a polynucleotide sequence that is identical to or complementary to a sequence in the designated DNA. The degree (or "percent") of identity or complementarity to the cDNA will be approximately 50% or greater, will preferably be at least about 70% or greater, and more preferably will be at least about 90%. The sequence that corresponds will be at least about 50 nucleotides in length, will preferably be about 60 nucleotides in length, and more preferably, will be at least about 70 nucleotides in length. The correspondence between the gene or gene fragment of interest and the cDNA can be determined by methods known in the art, and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density. Thus, "purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

A polynucleotide fragment or segment refers to a polynucleotide sequence which is comprised of a sequence of at least about 6 nucleotides, is preferably at least about 8 nucleotides, is more preferably at least about 10 nucleotides, is more preferably at least about 12 nucleotides, and is even more preferably at least about 15–20 nucleotides corresponding, i.e., identical to or complementary to, a region of a designated nucleotide sequence. The sequence may be complementary to or identical to a sequence, which is unique to a particular polynucleotide sequence as determined by techniques known in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The polynucleotide fragment or segment will not necessarily be derived physically from the nucleotide sequence of interest under study, but may be generated in any manner, including but not limited to chemical synthesis, replication, reverse transcription or transcription, which is based on the information provided by the sequence of bases in the region(s) from which the polynucleotide is derived; as such, it may represent either a sense or an antisense orientation of the original polynucleotide. In addition, combinations of regions corresponding to that of the designated sequence may be modified in ways known in the art to be consistent with an intended use.

The term "primer" denotes a specific oligonucleotide sequence complementary to a target nucleotide sequence and used to hybridize to the target nucleotide sequence and serve as an initiation point for nucleotide polymerization catalyzed by either DNA polymerase, RNA polymerase or reverse transcriptase.

The term "probe" denotes a defined nucleic acid segment (or nucleotide analog segment, i.e., PNA) which can be used to identify specific DNA or RNA present in samples bearing the complementary sequence.

"Polypeptide" as used herein indicates a molecular chain of amino acids and does not refer to a specific length of the product. Thus, peptides, oligopeptides and proteins are included within the definition of polypeptide. This term, however, is not intended to refer to post-expression modifications of the polypeptide, for example, glycosylations, acetylations, phosphorylations and the like.

A "polypeptide" or "amino acid" sequence derived from a designated nucleic acid sequence refers to a polypeptide having an amino acid sequence identical to that of a polypeptide encoded in the sequence or a portion thereof wherein the portion consists of at least 3 to 5 contiguous amino acids, and more preferably at least 8 to 10 contiguous amino acids, and even more preferably 15 to 20 contiguous amino acids, or which is immunologically identifiable with a polypeptide encoded in the sequence.

A "recombinant polypeptide" as used herein means at least a polypeptide which by virtue of its origin or manipulation is not associated with all or a portion of the polypeptide with which it is associated in nature and/or is linked to a polypeptide other than that to which it is linked in nature. A recombinant or derived polypeptide is not necessarily translated from a designated nucleic acid sequence. It also may be generated in any manner, including chemical synthesis or expression of a recombinant expression system.

A polypeptide homologous to MMP-ABT polypeptides, is one which is encoded by a nucleic acid that selectively hybridizes to sequences of MMP-ABT or its variants.

The term "synthetic peptide" as used herein means a polymeric form of amino acids of any length, which may be chemically synthesized by methods well-known to the routineer. These synthetic peptides are useful in various applications "Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

An "Expressed Sequence Tag" or "EST" refers to the partial sequence of a cDNA insert which has been made by reverse transcription of mRNA extracted from a tissue, followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. "Specific binding member" as used herein means a member of a specific binding pair. That is, two different molecules where one of the molecules through chemical or physical means specifically binds to the second molecule. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazol or adamantane.

The various "signal-generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents.

The present invention provides reagents such as human MMP-ABT polynucleotide sequences derived from an MMP-ABT of interest, polypeptides encoded therein, and antibodies developed from these polypeptides. The present invention also provides reagents such as oligonucleotide fragments derived from the disclosed polynucleotides and nucleic acid sequences complementary to the polynucleotides. The polynucleotides or polypeptides or antibodies of the present invention may be used in the diagnosis, prognosis, and/or treatment of individuals with conditions associated with the expression of the MMP-ABT gene, such as cancer, arthritis, or inflammation, or to identify a predisposition to these conditions. The sequences disclosed herein represent unique polynucleotides which can be used in assays or for producing a disease specific profile of gene transcription activity.

Selected MMP-ABT polynucleotides can be used in the methods described herein for the detection of normal or altered gene expression. Such methods may employ the MMP-ABT polynucleotides disclosed herein or oligonucleotides, fragments or derivatives thereof, or nucleic acid sequences complementary to these polynucleotides.

The polynucleotides disclosed herein, their complementary sequences or fragments of either can be used in assays to detect, amplify or quantify genes, cDNAs or mRNAs relating to cancer, arthritis, or inflammation and associated conditions. They also can be used to identify an entire or partial coding region which encodes for MMP-ABT polypeptide. They further can be provided in individual containers in the form of a kit for assays, or provided as individual compositions. If provided in a kit for assays, other suitable reagents such as buffers, conjugates and the like may be included.

The polynucleotide(s) may be in the form of mRNA or DNA. Polynucleotides in the form of DNA, cDNA, genomic DNA, and synthetic DNA are within the scope of the present invention. The DNA may be double-stranded or single-stranded, and if single stranded may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and additional coding sequence such as a leader or secretory sequence or a proprotein sequence, or the coding sequence for the polypeptide (and optionally additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence, which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the polypeptide. The polynucleotides may also encode for a proprotein which is the protein plus additional amino acid residues at the N-terminus. A protein having a prosequence is a proprotein and may in some cases be an inactive form of the protein. Once the prosequence is cleaved an active protein remains. Thus, the polynucleotide of the present invention may encode for a protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein. See, for example, I. Wilson, et al., *Cell* 37:767 (1984).

It is contemplated that polynucleotides will be considered to hybridize to the sequences provided herein if there is at least 50%, and preferably at least 70% identity between the polynucleotide and the sequence.

Probes constructed according to the polynucleotide sequences of the present invention can be used in various assay methods to provide various types of analysis. For example, such probes can be used in Fluorescent In Situ Hybridization (FISH) technology to perform chromosomal analysis, and used to identify cancer-specific structural alterations in the chromosomes, such as deletions or translocations that are visible from chromosome spreads or detectable using PCR-generated and/or allele specific oligonulcleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in fixed tissue specimens or cells.

The present invention further relates to an MMP-ABT polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the MMP-ABT polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are preferably provided in an isolated form, and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, eg, replacement of leucine with isoleucine or threonine with serine. In contrast, variations may include nonconservative changes, eg, replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Preferably, a polypeptide of the present invention is one having at least 40% identity, more preferably, at least 50% identity, even more preferably at least 60% identity and even more preferably, at least 70% identity to SEQ ID NO:10. Such a polypeptide may also possess the ability to cleave at least the substrate described as SEQ ID NO:13.

The present invention also provides an antibody produced by using a purified MMP-ABT polypeptide of which at least a portion of the polypeptide is encoded by MMP-ABT polynucleotide selected from the polynucleotides provided herein. These antibodies may be used in the methods provided herein for the detection of MMP-ABT polypeptides in test samples. The antibody also may be used for therapeutic purposes, for example, in neutralizing the activity of a MMP-ABT polypeptide in conditions associated with altered or abnormal expression of the MMP-ABT gene.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al, published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall, et al., *PCR Methods and Applications* 4: 80–84 (1994), which also is incorporated herein by reference.

Other known amplification methods which can be utilized herein include but are not limited to the so-called "NASBA" or "3SR" technique described in *PNAS USA* 87:1874–1878 (1990) and also described in *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 [1996]) and European Patent Application No. 684315; and target mediated amplification, as described by PCT Publication WO 9322461.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method herein provided are labeled with capture and detection labels wherein probes are labeled with one type of label and primers are labeled with the other type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences are generally selected to be shorter than the primer sequences and therefore have a lower melt temperature than the primers. Accordingly, the melt temperature of the amplicon produced by the primers should also have a higher melt temperature than the probes. Thus, as the mixture is cooled, the re-formation of the double stranded amplicon is expected although as previously stated, this is not the case. Instead, the probes are found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

A test sample is typically anything suspected of containing a target sequence. Test samples can be prepared using methodologies well known in the art such as by obtaining a specimen from an individual and, if necessary, disrupting any cells contained therein to release target nucleic acids. Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can include well known amplification reactions that utilize thermal cycle reaction mixtures, particularly PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

While the amplification primers initiate amplification of the target sequence, in some cases, the detection (or hybridization) probe is not involved in amplification. Detection probes are generally nucleic acid sequences or uncharged nucleic acid analogs such as, for example, peptide nucleic acids which are disclosed in International Patent Application WO 92/20702; morpholino analogs which are described in U.S. Pat. Nos. 5,185,444, 5,034,506, and 5,142,047; and the like. Depending upon the type of label carried by the probe, the probe is employed to capture or detect the amplicon generated by the amplification reaction. The probe is not involved in amplification of the target sequence and therefore may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendable.

Accordingly, the ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Alternatively, a probe may be involved in the amplifying a target sequence, via a process known as "nested PCR". In nested PCR, the probe has characteristics, which are similar to those of the first and second primers normally used for amplification (such as length, melting temperature etc.), and as such, may itself serve as a primer in an amplification reaction. Generally in nested PCR, a first pair of primers ($P_1$ and $P_2$) are employed to form primary extension products. One of the primary primers (for example, $P_1$) may optionally be a capture primer (i.e. linked to a member of a first reactive pair), whereas the other primary primer ($P_2$) is not. A secondary extension product is then formed using a probe ($P_{1'}$) and a probe ($P_{2'}$) which may also have a capture type label (such as a member of a second reactive pair) or a detection label at its 5' end. The probes are complementary to and hybridize at a site on the template near or adjacent the site where the 3' termini of $P_1$ and $P_2$ would hybridize if still in solution. Alternatively, a secondary extension product can be formed using the $P_1$ primer with the probe ($P_{2'}$) or the $P_2$ primer with the probe ($P_{1'}$) sometimes referred to as "heminested PCR". Thus, a labeled primer/probe set generates a secondary product which is shorter than the primary extension product. Furthermore, the secondary product may be detected either on the basis of its size or via its labeled ends (by detection methodologies well known to those of ordinary skill in the art). In this process, probe and primers are generally employed in equivalent concentrations.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II™ (Clontech). The amines can be reacted to various haptens using conventional activation and linking chemistries. In addition, copending applications U.S. Ser. Nos. 625,566, filed Dec. 11, 1990 and 630,908, filed Dec. 20, 1990, which are each incorporated herein by reference, teach methods for labeling probes at their 5' and 3' termini, respectively. Publications WO92/10505, published Jun. 25, 1992 and WO 92/11388 published Jul. 9, 1992 teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., Tet. Letters 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

Capture labels are carried by the primers or probes and can be a specific binding member which forms a binding pair with the solid phase reagent's specific binding member. It will be understood, of course that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides wherein at least one polynucleotide is provided herein, hybridizing the test sample with the plurality of polynucleotides and detecting the hybridization complexes. The hybridization complexes are identified and quantitated to compile a profile which is indicative of cancer, metastases, arthritis or inflammatory conditions. Expressed RNA sequences may further be detected by reverse transcription and amplification of the DNA product by procedures well-known in the art, including polymerase chain reaction (PCR).

Antisense and Gene Therapy.

The present invention also encompasses the use of gene therapy methods for the introduction of anti-sense MMP-ABT gene derived molecules such as polynucleotides or oligonucleotides of the present invention into patients having conditions (such as cancer, arthritis or inflammation) that are associated with bnormal expression of MMP-ABT polynucleotides. These molecules, including antisense RNA and DNA fragments and ribozymes, are designed to inhibit the translation of a MMP-ABT polynucleotide mRNA, and may be used therapeutically in the treatment of conditions associated with altered or abnormal expression of the MMP-ABT polynucleotide.

Alternatively, the oligonucleotides described above can be delivered to cells by procedures in the art such that the anti-sense RNA or DNA is subsequently expressed in vivo whereby it inhibits production of MMP-ABT polypeptide in the manner described above. Antisense constructs to MMP-ABT polynucleotide, therefore, reverse the action of MMP-ABT transcripts and may be used for treating cancer, arthritis, inflammation and related disease states. These antisense constructs may also be used to treat tumor metastases.

Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of MMP-ABT polypeptide. For triple helix, see, for example, Lee et al., *Nucl. Acids. Res.* 6:3073 (1979); Cooney et al., *Science* 241:456 (1988); and Dervan et al., *Science* 251:1360 (1991) The antisense RNA oligonucleotide hybridizes to the mRNA in vivo and blocks translation of an mRNA molecule into the MMP-ABT polypeptide. For antisense, see, for example, Okano, *J. Neurochem.* 56:560 (1991); and "Oligodeoxynucleotides as Antisense Inhibitors of Gene Expression", CRC Press, Boca Raton, Fla. (1988). Antisense oligonucleotides act with greater efficacy when modified to contain artificial internucleotide linkages which render the molecule resistant to nucleolytic cleavage. Such artificial internucleotide linkages include but are not limited to methylphosphonate, phosphorothiolate and phosphoroamydate internucleotide linkages.

The present invention also encompasses gene therapy whereby the gene encoding MMP-ABT is regulated in a patient. Various methods of transferring or delivering DNA to cells for expression of the gene product protein, otherwise referred to as gene therapy, are disclosed in "Gene Transfer into Mammarian Somatic Cells in vivo", N. Yang, *Crit. Rev. Biotechn.* 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating medical problems with gene therapy include therapeutic strategies such as identifying the defective gene and then adding a functional gene to either replace the function of the defective gene or to augment a slightly functional gene; or prophylactic strategies, such as adding a gene which encodes a protein product that will treat the condition or that will make the tissue or organ more susceptible to a treatment regimen.

Many protocols for transfer of MMP-ABT DNA or MMP-ABT regulatory sequences are envisioned in this invention. Transfection of promoter sequences, other than one specifically associated with MMP-ABT, or other sequences which would increase production of MMP-ABT protein are also envisioned as methods of gene therapy. An example of this technology is found in Transkaryotic Therapies, Inc., of Cambridge, Mass., using homologous recombination to insert a "genetic switch" that turns on an erythroprotein gene in cells. See *Genetic Engineering News,* Apr. 15, 1994. Such "genetic switches" could be used to activate MMP-ABT (or a MMP-ABT receptor) in cells not normally expressing these proteins.

Gene transfer methods for gene therapy fall into three broad categories: (1) physical (e.g., electroporation, direct gene transfer and particle bombardment), (2) chemical (e.g. lipid-based carriers and other non-viral vectors) and (3) biological (e.g. virus derived vectors). For example, non-viral vectors such as liposomes coated with DNA may be directly injected intravenously into the patient. It is believed that the liposome/DNA complexes are concentrated in the liver where they deliver the DNA to macrophages and Kupffer cells. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses. In vivo gene transfer involves introducing the DNA into the cells of the patient when the cells are within the patient. All three of the broad based categories described above may be used to achieve gene transfer in vivo, ex vivo, and in vitro.

Mechanical (i.e. physical) methods of DNA delivery can be achieved by direct injection of DNA, such as microinjection of DNA into germ or somatic cells, pneumatically delivered DNA-coated particles, such as the gold particles used in a "gene gun," and inorganic chemical approaches such as calcium phosphate transfection. It has been found that physical injection of plasmid DNA into muscle cells yields a high percentage of cells which are transfected and have a sustained expression of marker genes. The plasmid DNA may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art.

Chemical methods of gene therapy involve carrier mediated gene transfer through the use of fusogenic lipid vesicles such as liposomes or other vesicles for membrane fusion. A carrier harboring a DNA of interest can be conveniently introduced into body fluids or the bloodstream and then site specifically directed to the target organ or tissue in the body. Liposomes, for example, can be developed which are cell specific or organ specific. The foreign DNA carried by the liposome thus will be taken up by those specific cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then resides in the cytoplasm or in the nucleoplasm of the recipient cell. DNA can be coupled to carrier nuclear proteins in specifically engineered vesicle complexes and carried directly into the nucleus.

Carrier mediated gene transfer may also involve the use of lipid-based proteins which are not liposomes. For example, lipofectins and cytofectins are lipid-based positive ions that bind to negatively charged DNA, forming a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream; target cells that have the cell surface receptor will specifically bind the ligand and transport the ligand-DNA complex into the cell.

Biological gene therapy methodologies usually employ viral vectors to insert genes into cells. The term "vector" as used herein in the context of biological gene therapy means a carrier that can contain or associate with specific polynucleotide sequences and which functions to transport the specific polynucleotide sequences into a cell. The transfected cells may be cells derived from the patient's normal tissue, the patient's diseased tissue, or may be non-patient cells. Examples of vectors include plasmids and infective microorganisms such as viruses, or non-viral vectors such as the ligand-DNA conjugates, liposomes, and lipid-DNA complexes discussed above.

It may be desirable that a recombinant DNA molecule comprising a MMP-ABT DNA sequence is operatively linked to an expression control sequence to form an expression vector capable of expressing MMP-ABT. Alternatively, gene regulation of MMP-ABT may be accomplished by administering proteins that bind to control regions associated with the MMP-ABT gene, or its corresponding RNA transcript to modify the rate of transcription or translation.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome. For example, altered retrovirus vectors have been used in ex vivo methods to introduce genes into peripheral and tumor-infiltrating lymphocytes, hepatocytes, epidermal cells, myocytes, or other somatic cells (which may then introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Drug Screening.

The present invention also provides a method of screening a plurality of compounds for specific binding to a MMP-ABT polypeptide, or any fragment thereof, to identify at least one compound which specifically binds the MMP-ABT polypeptide. Such a method comprises the steps of providing at least one compound; combining the MMP-ABT polypeptide with each compound under suitable conditions for a time sufficient to allow binding; and detecting MMP-ABT polypeptide binding to each compound.

The present invention also provides a method of screening a plurality of compounds for inhibition of the activity of a MMP-ABT polypeptide, or any fragment thereof, to identify at least one compound which specifically inhibits the activity of the MMP-ABT polypeptide. Such a method comprises the steps of providing at least one compound; combining the MMP-ABT polypeptide with each compound under suitable conditions for a time sufficient to allow interaction or binding; and detecting MMP-ABT polypeptide inhibition by each compound.

The polypeptide or peptide fragment employed in such a test may either be free in solution, affixed to a solid support, borne on a cell surface or located intracellularly. One method of drug screening utilizes eukaryotic or prokaryotic host cells which are stably transformed with recombinant nucleic acids which can express the polypeptide or peptide fragment. Drugs may be screened against such transformed cells in competitive binding or enzymatic inhibition assays. For example, the formation of complexes between a polypeptide and the agent being tested can be measured in either viable or fixed cells.

The present invention thus provides methods of screening for drugs or any other agent which can be used to treat conditions associated with cancer, arthritis, or inflammation resulting from abnormal MMP-ABT production. These methods comprise contacting the agent with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is a measure of the ability of the particular drug to bind to polypeptide or to interfere with the polypeptide/cell complex.

The present invention also encompasses the use of competitive drug screening assays in which neutralizing antibodies capable of binding polypeptide specifically compete with a test drug for binding to the polypeptide or fragment thereof. In this manner, the antibodies can be used to detect the presence of any polypeptide in the test sample which shares one or more antigenic determinants with a polypeptide provided herein.

Another technique for drug screening provides high throughput screening for compounds having suitable binding affinity to at least one polypeptide disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the drug screening techniques described herein. In addition, non-neutralizing antibodies can be used to capture the polypeptide and immobilize it on the solid support. See, for example, EP 84/03564, published on Sep. 13, 1984, which is incorporated herein by reference.

Drug Design

The goal of rational drug design is to produce structural analogs of biologically active polypeptides of interest or of the small molecules including agonists, antagonists, or inhibitors with which they interact. Such structural analogs can be used to fashion drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J Biochem.* (*Tokyo*) 113 (6):742–746 (1993), incorporated herein by reference.

It also is possible to isolate a target-specific antibody, selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then could be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which are derivable from the nucleic acid sequence provided herein will provide guidance to those employing computer modeling techniques in place of or in addition to x-ray crystallography.

Antibodies specific to the MMP-ABT polypepeptide may further be used to inhibit the biological action of the polypeptide by binding to the polypeptide. In this manner, the antibodies may be used in therapy, for example, to treat cancer and its metastases.

Further, such antibodies can detect the presence or absence of the MMP-ABT polypeptide and, therefore, are useful as diagnostic markers for the diagnosis of cancers, arthritis, and inflammatory conditions. Such antibodies may also function as a diagnostic marker for these conditions. The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of the MMP-ABT polypeptide by binding to the MMP-ABT polypeptide, or in some cases the antagonist may be an oligonucleotide. Examples of small molecule inhibitors include but are not limited to small peptides or peptide-like molecules.

The antagonists and inhibitors may be employed as a composition with a pharmaceutically acceptable carrier, including but not limited to saline, buffered saline, dextrose, water, glycerol, ethanol and combinations thereof. Administration of MMP-ABT polypeptide inhibitors are preferably systemic. The present invention also provides an antibody which inhibits the action of such polypeptide.

Recombinant Technology.

The present invention provides host cells and expression vectors comprising polynucleotides of the present invention and methods for the production of polypeptides they encode. Such methods comprise culturing the host cells under conditions suitable for the expression of the MMP-ABT polynucleotide and recovering the MMP-ABT polypeptide. from the cell culture.

The present invention also provides vectors which include polynucleotides of the present invention, host cells which are genetically engineered with vectors of the present invention and the production of polypeptides of the present invention by recombinant techniques.

Host cells are genetically engineered (transduced or transformed or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying the MMP-ABT genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include but are not limited to LTR or SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Salmonella typhimurium*; Streptomyces sp.; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pSPORTI (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacZ, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retrovirus, and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology", 2nd edition, Appleton and Lang, Paramount Publishing, East Norwalk, Conn. (1994).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan.

Various mammalian cell culture systems can also be employed to express recombinant protein. Examples of mammalian expression systems include the COS-7 lines of monkey kidney fibroblasts described by Gluzman, *Cell* 23:175 (1981), and other cell lines capable of expressing a compatible vector, such as the C 127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

MMP-ABT polypeptide is recovered and purified from recombinant cell cultures by known methods including ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price, et al., *J. Biol. Chem.* 244:917 [1969]). Protein refolding steps can be used, as necessary, in completing configuration of the protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to the ordinarily skilled artisan.

The following is the general procedure for the isolation and analysis of cDNA clones. In a particular embodiment disclosed herein, an EST homologous to a portion of human MMPs was identified by comparison with a consensus sequence to human MMPs.

The cDNA insert was sequenced in entirety, analyzed in detail set forth in the Examples and is disclosed in the Sequence Listing as SEQ NO:4. These polynucleotides may contain an entire open reading frame with or without associated regulatory sequences for a particular gene, or they may encode only a portion of the gene of interest. This is attributed to the fact that many genes are several hundred, and sometimes several thousand, bases in length and, with current technology, cannot be cloned in their entirety because of vector limitations, incomplete reverse transcription of the first strand, or incomplete replication of the second strand. Contiguous, secondary clones containing additional nucleotide sequence may be obtained using a variety of methods known to those of skill in the art.

Methods for DNA sequencing are well known in the art. Conventional enzymatic methods employ DNA polymerase, Klenow fragment, Sequenase (US Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while the other two reading frames tend to contain numerous stop codons. In such cases reading frame determination is straightforward. In other more difficult cases, further analysis is required.

Algorithms have been created to analyze the occurrence of individual nucleotide bases at each putative codon triplet. See, for example J. W. Fickett, *Nuc Acids Res* 10:5303 (1982). Coding DNA for particular organisms (bacteria, plants, and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well established recombinant DNA techniques. See J. Sambrook et al., supra. Vectors of interest include cloning vectors, such as plasmids, cosmids, phage derivatives, phagemids, as well as sequencing, replication, and expression vectors, and the like. In general, such vectors contain an origin of replication functional in at least one organism, convenient restriction endonuclease digestion sites, and selectable markers appropriate for particular host cells. The vectors can be transferred by a variety of means known to those of skill in the art into suitable host cells which then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel, et al., *Current Protocols in Molecular Biology*, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and as such may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequence.

Expression of a particular cDNA may be accomplished by subcloning the cDNA into an appropriate expression vector and transfecting this vector into an appropriate expression host. The cloning vector used for the generation of the cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription and a number of unique restriction sites, including EcoR I, for cloning. The vector can be transfected into an appropriate host strain of *E. coli*.

Induction of the isolated bacterial strain with isopropylthiogalactoside (IPTG) using standard methods will produce a fusion protein which contains the first seven residues of beta-galactosidase, about 15 residues of linker, and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include but are not limited to MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays.

The polypeptides including their fragments or derivatives or analogs thereof of the present invention, or cells expressing them, can be in a variety of assays, many of which are described herein, for the detection of antibodies. They also can be used as an immunogen to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide corresponding to a sequence of the present invention can be obtained by direct injection of the polypeptide into an animal or by administering the polypeptide to an animal such as a mouse, rabbit, goat or human. A mouse, rabbit or goat is preferred. The antibody so obtained then will bind the polypeptide itself. In this manner, even a sequence encoding only a fragment of the polypeptide can be used to generate antibodies that bind the native polypeptide. Such antibodies can then be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495–497 (1975), the trioma technique, the human B-cell hybridoma technique as described by Kozbor et al, *Immun. Today* 4:72 (1983), and the EBV-hybridoma technique to produce human monoclonal antibodies as described by Cole, et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the monoclonal antibodies or fragment thereof of the present invention can be employed in various assay systems to determine the presence, if any, of MMP-ABT polypeptide in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of a MMP-ABT polypeptide antigen present in the test sample and captured on the solid phase, if any, is determined by detecting the measurable signal generated by the signal generating compound. The amount of MMP-ABT polypeptide antigen present in the test sample is proportional to the signal generated.

Or, a polyclonal or monoclonal MMP-ABT polypeptide antibody or fragment thereof, or a combination of these antibodies which is bound to a solid support, the test sample and an indicator reagent comprising a monoclonal or polyclonal antibody or fragments thereof, which specifically binds to MMP-ABT polypeptide antigen, or a combination of these antibodies to which a signal generating compound is attached, are contacted to form a mixture. This mixture is incubated for a time and under conditions sufficient to form antibody/antigen/antibody complexes. The presence, if any, of MMP-ABT polypeptide present in the test sample and captured on the solid phase is determined by detecting the measurable signal generated by the signal generating compound. The amount of MMP-ABT polypeptide proteins present in the test sample is proportional to the signal generated.

In another assay format, one or a combination of at least two monoclonal antibodies of the invention can be employed as a competitive probe for the detection of antibodies to MMP-ABT polypeptide protein. For example, MMP-ABT polypeptide proteins such as the recombinant antigens disclosed herein, either alone or in combination, are coated on a solid phase. A test sample suspected of containing antibody to MMP-ABT polypeptide antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of MMP-ABT polypeptide antigens in fixed tissue sections, as well as fixed cells by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific MMP-ABT polypeptide proteins from cell cultures or biological tissues such as to purify recombinant and native MMP-ABT polypeptide antigens and proteins.

The monoclonal antibodies of the invention can also be used for the generation of chimeric antibodies for therapeutic use, or other similar applications.

The monoclonal antibodies or fragments thereof can be provided individually to detect MMP-ABT polypeptide antigens. Combinations of the monoclonal antibodies (and fragments thereof) provided herein also may be used together as components in a mixture or "cocktail" of at least one MMP-ABT polypeptide antibody of the invention with antibodies to other MMP-ABT polypeptide regions, each having different binding specificities. Thus, this cocktail can include the monoclonal antibodies of the invention which are directed to MMP-ABT polypeptide proteins and other monoclonal antibodies to other antigenic determinants of the MMP-ABT polypeptide genome.

The polyclonal antibody or fragment thereof which can be used in the assay formats should specifically bind to a MMP-ABT polypeptide region or other MMP-ABT polypeptide proteins used in the assay. The polyclonal antibody used preferably is of mammalian origin; human, goat, rabbit or sheep anti- MMP-ABT polypeptide polyclonal antibody can be used. Most preferably, the polyclonal antibody is rabbit polyclonal anti-MMP-ABT polypeptide antibody. The polyclonal antibodies used in the assays can be used either alone or as a cocktail of polyclonal antibodies. Since the cocktails used in the assay formats are comprised of either monoclonal antibodies or polyclonal antibodies having different MMP-ABT polypeptide specificity, they would be useful for diagnosis, evaluation and prognosis of MMP-ABT polypeptide condition, as well as for studying MMP-ABT polypeptide protein differentiation and specificity.

It is contemplated and within the scope of the present invention that the MMP-ABT polypeptide may be detectable in assays by use of a recombinant antigen as well as by use of a synthetic peptide or purified peptide, which contains an amino acid sequence of MMP-ABT polypeptide. It also is within the scope of the present invention that different synthetic, recombinant or purified peptides identifying different epitopes of the MMP-ABT polypeptide can be used in combination in an assay to diagnose, evaluate, or prognose the disease condition. In this case, these peptides can be coated onto one solid phase, or each separate peptide may be coated on separate solid phases, such as microparticles, and then combined to form a mixture of peptides which can be later used in assays. Furthermore, it is contemplated that multiple peptides which define epitopes from different polypeptides may be used in combination to make a diagnosis, evaluation, or prognosis of disease. Peptides coated on solid phases or labelled with detectable lables are then allowed to compete with peptides from a patient sample for a limited amount of antibody. A reduction in binding of the synthetic, recombinant, or purified peptides to the antibody (or antibodies) is an indication of the presence of MMP-ABT polypeptides in the patient sample, which in turn indicates the presence of disease in the patient. Such variations of assay formats are known to those of ordinary skill in the art and are discussed herein below.

In another assay format, the presence of antibody and/or antigen to MMP-ABT polypeptide can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/ indicator reagent complexes. The presence of one or more analytes is determined by detecting a signal generated in connection with the complexes formed on either or both solid phases as an indication of the presence of one or more analytes in the test sample. In this assay format, recombinant antigens derived from human expression systems may be utilized as well as monoclonal antibodies produced from the proteins derived from the mammalian expression systems as disclosed herein. Such assay systems are described in greater detail in EP Publication No. 0473065.

In yet other assay formats, the polypeptides disclosed herein may be utilized to detect the presence of anti-MMP-ABT polypeptide in test samples. For example, a test sample is incubated with a solid phase to which at least one recombinant protein has been attached. These are reacted for a time and under conditions sufficient to form antigen/ antibody complexes. Following incubation, the antigen/ antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent.

After incubation for a time and under conditions sufficient for antibody/antigen complexes to form, the solid phase is separated from the free phase, and the label is detected in either the solid or free phase as an indication of the presence of MMP-ABT polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as *E. coli* is used as a capture antigen on a solid phase, a test sample is added to the so-prepared solid phase, and a recombinant protein derived from a different source (i.e., non-*E. coli*) is utilized as a part of an indicator reagent. Likewise, combinations of a recombinant antigen on a solid phase and synthetic peptide in the indicator phase also are possible. Any assay format which utilizes an antigen specific for MMP-ABT polypeptide from a first source as the capture antigen and an antigen specific for MMP-ABT polypeptide from a different second source are contemplated. Thus, various combinations of recombinant antigens, as well as the use of synthetic peptides, purified proteins, and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (either recombinant or synthetic) employed in the assay. Other components such as buffers, controls, and the like, known to those of ordinary skill in art, may be included in such test kits. It also is contemplated to provide test kits which have means for collecting test samples comprising accessible body fluids, eg. blood, urine, saliva, and stool. Such collection means include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization, and preservation of test specimens obtained by surgery or needle biopsy are also useful. It is contemplated that all kits may be configured in two components; one component for collection and transport of the specimen, and the other component for the analysis of the specimen. Further, kits for the collection, stabilization, and preservation of test specimens may be configured for use by untrained personnel and may be available in the open market for use at home with subsequent transportation to a laboratory for analysis of the test sample.

*E. coli* bacteria (clone #907334) has been deposited at the American Type Culture Collection (A.T.C.C.), 12301 Parklawn Drive, Rockville, Md. 20852, as of Mar. 10, 1997, under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The cDNA sequence in all of the deposited material is incorporated herein by reference. Clone #907334 was accorded A.T.C.C. Deposit No.

Having now generally described the invention, a complete understanding can be obtained by reference to the following specific examples. The following examples are given for the purpose of illustrating various embodiments of the invention and are not meant to limit the present invention in any fashion.

EXAMPLE 1

Isolation of Human cDNA Clones Homologous to MMPs

A consensus of twelve human matrix metalloprotease amino acid sequences was obtained by aligning sequences using the PILEUP program in the Wisconsin Sequence Analysis Package (Genetics Computer Group [GCG], Madison, Wis.). The consensus sequence was derived from a plurality of seven sequences at a given amino acid position. The letter "x" was substituted for each amino acid that differed from the determined consensus residue and was used to represent any amino acid.

The MMP consensus sequence (SEQ ID NO:7, see FIG. 1) was used to search the LIFESEQ™ human expression database (Incyte Pharmaceuticals, Inc., Palo Alto, Calif.) for human MMP sequences. This database is comprised of partial sequences of cDNA clone inserts, so-called expressed sequence tags (ESTs), derived from cDNA libraries from various human tissues. A search of LIFESEQ™ using the BLAST and Smith-Waterman similarity search algorithms with the MMP consensus sequence identified an EST (from clone #907334) unique to the LIFESEQ™ database and whose deduced amino acid sequence of one reading frame contained the amino acid sequence PRCGVTD (SEQ ID NO:8), similar to the "cysteine switch" motif in the propeptide region of all MMPs. The EST from clone #907334 was derived from a colon tissue library using oligo-dT for the reverse transcription reaction. The cDNA clone #907334 in pSPORT1 plasmid (GIBCO BRL, Gaithersburg, Md.) was obtained for further study.

Clone #907334 was amplified in bacteria and digested with the restriction enzymes EcoRI and NotI to determine the size of the cDNA insert. Insert length was determined to be approximately 1700 base pairs. The complete nucleotide sequence of the clone was obtained by initially sequencing with plasmid primers and subsequently with primers near the end of each newly obtained sequence. All sequence information from each reaction was compiled and analyzed using the Sequencher™ program (Gene Codes Corporation, Ann Arbor, Mich.). Sequencing was continued until both strands of the cloned cDNA insert were sequenced in entirety.

Figure 6:
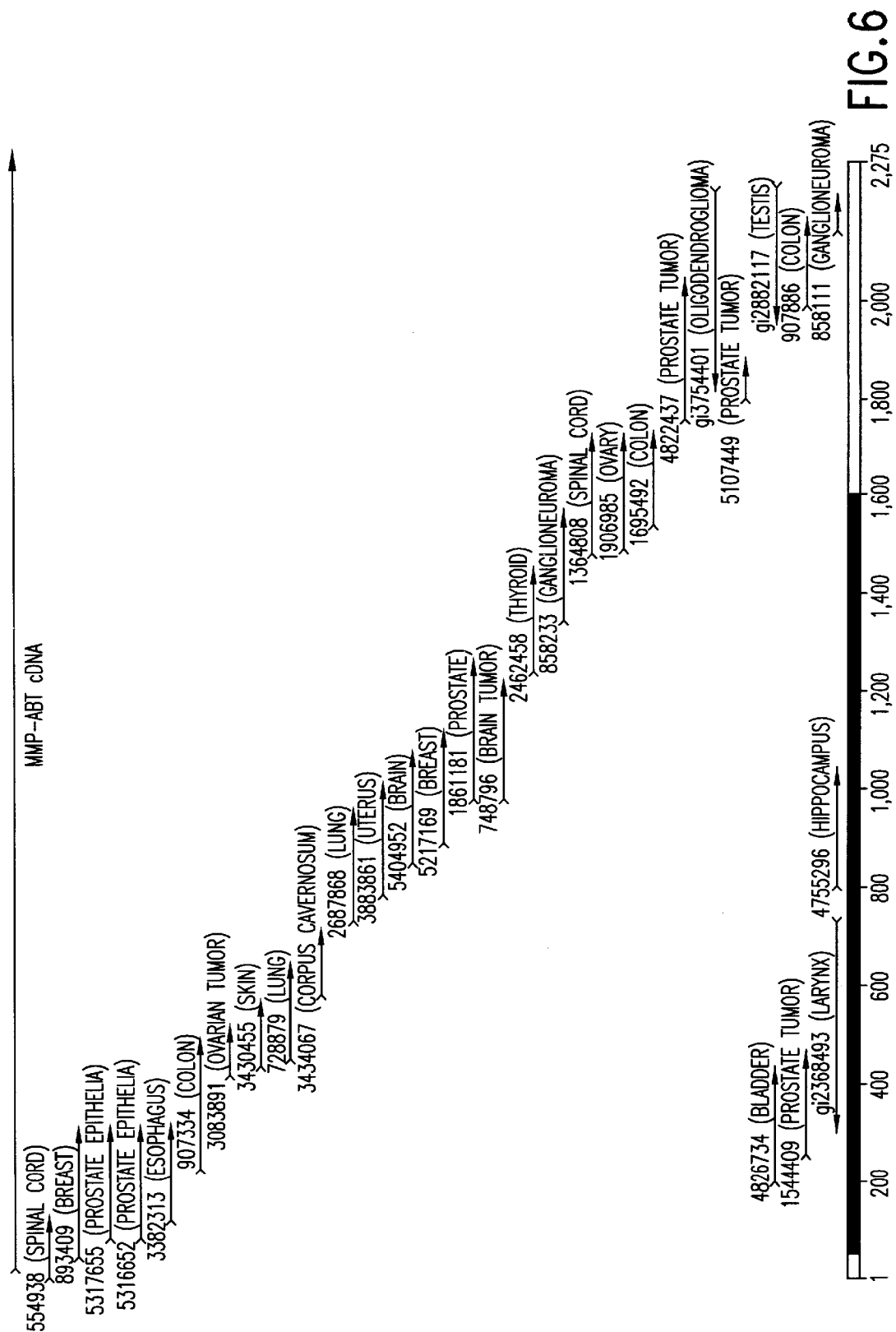
FIG. 6 shows the alignment and tissue distibution of ESTs found in LifeSeq™ which are identical or have overlapping sequences to regions of MMP-ABT cDNA.
Figure 7:
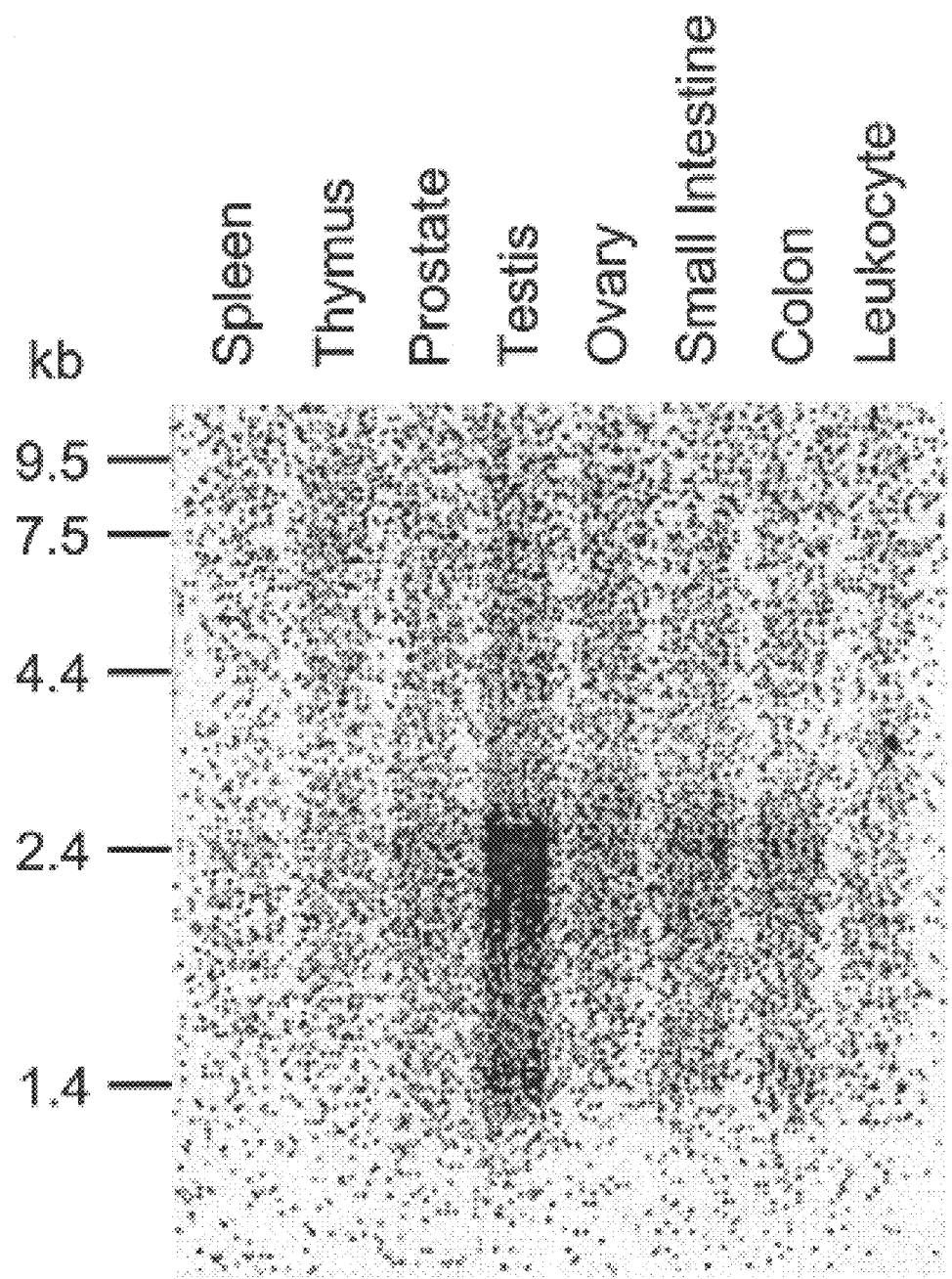
FIG. 7 shows a Phospholmage of a Northern blot of human RNA (2 µg of poly A+ RNA/lane) probed with a $^{32}$P-labeled MMP-ABT cDNA probe.

The nucleotide sequence of clone 907334 (nucleic acid positions 209 to 1870 of SEQ ID NO:1) was then compared to LIFESEQ™ and other public databases (for example, GenBank and the Washington University/Merck EST databases), using the BLAST and Smith-Waterman programs (default parameters). Twenty-eight ESTs having sequences identical to some portion of the clone 907334 cDNA were found in LIFESEQ™ (see FIG.6). These new ESTs had been sequenced from cDNA libraries derived from a variety of tissue types. Thus, the tissues indicated in FIG. 6 express at least small amounts of the mRNA encoded by MMP-ABT cDNA.

Another four ESTs were found having certain regions that were not homologous to MMP-ABT. We presume that these clones contain unspliced intronic sequence or represent splice variants of MMP-ABT mRNA.

Six of the 31 identified ESTs contained overlapping and identical upstream sequences relative to the start of clone #907334. From an analysis of these overlapping sequences, additional sequence upstream from the 5' end of clone #907334 was obtained (SEQ ID NO:34). An in-frame methionine codon was identified 153 nucleotides upstream from the 5' end of clone #907334. At least five observations suggest that this is the translation start codon used in MMP-ABT mRNA:

1) a segment of these upstream nucleotides (i.e. SEQ ID NO:34, GGCGGC(A/G)AGATGG) containing the in-frame Met codon closely matches the Kozak consensus sequence for translation initiation (i.e. SEQ ID NO:35, GCCGCC(A/G)CCATGG), 2) the amino acid sequence encoded by the first ~20 residues is a hydrophobic region with similarity to signal peptides present in secreted proteins and found in all MMPs, 3) the position of this methionine is consistent with the position of the start codon from other MMPs (see FIG. 5), 4) the size of the open reading frame using this methionine as a start codon is consistent with the observed size of the mature mRNA on Northern blots (~2.4 kb), and 5) there are no upstream ATG codons. In addition, we obtained clone #554938 for sequencing and confirmed that the downstream, overlapping region was identical to clone #907334.

The full-length sequence of the MMP-ABT cDNA, including the methionine start codon is shown in FIG. 4; the sense strand (SEQ ID NO:1) is shown on top with its complement (SEQ ID NO:2) aligned directly beneath. The deduced amino acid sequence (SEQ ID NO:10) is shown beneath the complementary (lower) strand.

The amino acid sequence was compared to those of other MMPs (FIG. 5) and shown to contain a cysteine switch motif (SEQ ID NO:8) within the putative pro-peptide domain which was 86% homologous to the consensus cysteine switch motif of the other MMPs (PRCGVPD, SEQ ID NO:11). In addition, MMP-ABT contained an identical version (100%) of the highly conserved zinc binding consensus sequence (HEXaaGHXaaLGLXaaHS, SEQ ID NO:12) found in the putative catalytic domain. The sequence also contained a potential recognition and cleavage site (RXKR, SEQ ID NO:33) for Kex2-like proteases shown to be involved in enzyme activation of stromelysin 3 and the membrane-type MMPs.

EXAMPLE 2

Localization of Clone #907334 Transcripts

A. Nothern Blotting: In order to determine whether MMP-ABT mRNA sequences could be detected by hybridization, a 1717 bp fragment of MMP-ABT cDNA (corresponding to nucleotide positions 200–1917 of SEQ ID NO:1) was radiolabelled with $^{32}$P using a commercial random primer labeling kit (Pharmacia, Piscataway, N.J.). Specific activity of the labeled fragment was determined to be ~5×10⁸ cpm/μg DNA. The labeled cDNA was used as a probe to hybridize to mRNA (2 μg polyA+RNA) on Northern blots (specifically, Multiple Tissue Northerns 1 and 2, obtained from Clontech, Palo Alto, Calif.) which contained various human tissue RNA. The blots were prehybridized at 60° C. for 1 hour in Express Hyb solution (supplied with the blots) and hybridized (also in Express Hyb solution) at the same temperature for two hours in the presence of denatured probe at $1\times10^6$ cpm/mL. After washing the blots once in 2×SSPE+0. 1% SDS (20 min), and twice under stringent conditions (0.2×SSPE+0.1% SDS, 50° C., 20 min. each wash), the filters were exposed and analyzed on a Phosphorimager (Molecular Dynamics, Sunnyvale, Calif.). By Northern blotting, it was determined that MMP-ABT mRNA transcript is approximately 2.4 kb and is present in human testes and to a lesser extent in human colon, ovary, small intestine, and prostate tissue (FIG. 11). Smaller less abundant transcripts with similar tissue distribution were also observed.

B. Ribonuclease Protection Assay: Alternatively, instead of or in addition to performing a Northern blot, a ribonuclease protection assay may be performed to determine whether MMP-ABT is present in particular tissues. A ribonuclease protection assay is performed as follows:

1. Labeling of Complementary RNA (cRNA) Hybridization Probes. Labeled sense and antisense riboprobes are transcribed from the EST sequence, which contains an RNA polymerase promoter such as SP6 or T7. The sequence may be from a vector containing the appropriate EST insert or from a PCR-generated product of the insert using PCR primers which incorporate am RNA polymerase promoter sequence. The transcripts are prepared in a 20 μL reaction volume containing 1 μg of DNA template, 2 μL of 100 mM dithiothreitol, 0.8 μL of RNasin (10–40U), 500 μM each of ATP, CTP, GTP, 5 μL (alpha³²P) UTP or 100–500 μM biotinylated UTP, and 1 μL of RNA polymerase in transcription buffer (40 mM Tris-HCl, pH 7.5, 6 mM MgCl₂, 2 mM spermidine HCl, 5 mM NaCl). Following incubation at 37° C. for one hour, the transcripts are treated with DNase I (15 U) for an additional 30 min to digest the template. The probes then are isolated by spin columns, salt precipitation or electrophoresis techniques which are well-known in the art. Finally, the probes are dissolved in lysis buffer (5 M Guanidine Thiocyanate, 0.1 M EDTA, pH 7.0).

2. Hybridization of Labeled Probe to Target. Approximately 20 μg of extracted total cellular RNA, prepared as described in Sambrook, et al. supra, is placed in 10 μL of lysis buffer and mixed with either (i) $1\times10^5$ cpm of radioactively labeled probe or (ii) 250 pg of non-isotopically labeled probe, each in 2 μL of lysis buffer. The mixture then is incubated at 60° C. for 5 min and hybridized overnight at room temperature. See, T. Kaabache et al., *Anal. Biochem.* 232: 225–230 (1995).

3. RNase Digestion. Hybridizations are terminated by incubation with 380 μL of a solution containing 40 μg/mL RNase A and 625 U/mL RNase T1 in 1 mM EDTA, 300 mM NaCl, 30 mM Tris-HCl pH 7.4 for 45–60 min at room temperature. RNase digestion then is terminated by the addition of 60 μL of proteinase-K (1.7 mg/mL) containing 3.3% SDS, followed by incubation for 30 min at 37° C. The digested mixture then is extracted with phenol:chloroform:isoamyl alcohol to remove protein. The mRNA:cRNA hybrids are precipitated from the aqueous phase by the addition 4 μg yeast tRNA and 800 μL of ethanol, and incubation at −80° C. for 30 min. The precipitates are collected by centrifugation.

4. Fragment Analysis. The precipitates are dissolved in 5 μL of denaturing gel loading dye (80% formamide, 10 mM EDTA, pH 8.0, 1 mg/mL xylene cyanol, 1 mg/mL bromophenol blue) and electrophoresed in 6% polyacrylamide TBE, 8 M urea denaturing gels. The gels are dried under vacuum and autoradiographed. Quantitation can be performed by comparing the counts obtained from the test samples to a calibration curve that was generated by utilizing calibrators that are the sense strand. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents. Again, expression of an mRNA which is detectable by the labeled probe in a particular tissue suggests that MMP-ABT is produced in that tissue.

C. Dot Blot/Slot Blot: Dot and slot blot assays are also quick methods to evaluate the presence of a specific nucleic acid sequence in a complex mix of nucleic acid. To perform, up to 20 μg of RNA is mixed in 50 μL of 50% formamide, 7% formaldehyde, 1×SSC, incubate 15 min at 68° C. and cool on ice. Then, 100 μL of 20×SSC is added to the RNA mixture and loaded under vacuum onto a manifold apparatus that has a prepared nitrocellulose or nylon membrane. The membrane is soaked in water, 20×SSC for 1 hour, placed on two sheets of 20×SSC prewet Whatman #3 filter paper, and loaded into a slot blot or dot blot vacuum manifold apparatus. The slot blot is analyzed with probes prepared and labeled as described supra. Other methods and buffers not specifically detailed here are described in J. Sambrook et al., supra.

D. In Situ Hybridization: This method is useful to directly detect specific target nucleic acid sequences in cells using detectable nucleic acid hybridization probes.

Tissues are prepared with cross-linking fixatives agents such as paraformaldehyde or glutaraldehyde for maximum cellular RNA retention. See, L. Angerer et al., *Methods in Cell Biol.* 35: 37–71 (1991). Briefly, the tissue is placed in greater than 5 volumes of 1% glutaraldehyde in 50 mM sodium phosphate, pH 7.5 at 4° C. for 30 min. The solution is changed with fresh solution for a further 30 min fixing. The fixing solution should have an osmolality of approximately 0.375% NaCl. The tissue is washed once in isotonic NaCl to remove the phosphate.

The fixed tissues then are embedded in paraffin, as follows. The tissue is dehydrated through a series of ethanol concentrations for 15 min each: 50% twice, 70% twice, 85%, 90% and 100% twice. The tissue next is soaked in two changes of xylene for 20 min each at room temperature; then it is soaked in two changes of 1 xylene:1 paraffin for 20 min each at 60° C.; and then it is soaked in three final changes in paraffin for 15 min each.

The tissue next is cut in 5 μm sections using a standard microtome and placed on a slide previously treated with the tissue adhesive 3-aminopropyltriethoxysilane.

Paraffin is removed from the tissue by two 10 min xylene soaks and rehydrated in a series of ethanol concentrations; 99% twice, 95%, 85%, 70%, 50%, 30% and distilled water twice. The sections are pre-treated with 0.2 M HCl for 10 min and permeabilized with 2 μg/mL Proteinase-K at 37° C. for 15 min.

Labeled riboprobes transcribed from the pSPORT1 plasmid containing fragments of MMP-ABT cDNA are hybridized to the prepared tissue sections and hybridized overnight at 56° C. in 3× standard saline extract and 50% formamide.

Excess probe is removed by washing in 2× standard saline citrate and 50% formamide followed by digestion with 100 μg/mL RNase A at 37° C. for 30 min. Fluorescence probe is visualized by illumination with UV light under a microscope. Fluorescence in the cytoplasm is indicative of mRNA production. Fluorescence in the nucleus detects the presence of genomic material. Alternatively, the sections can be visualized by autoradiography.

EXAMPLE 3

Expression of MMP-ABT Sequences

A. Construction of Expression Vectors Containing, DNA Fragments Encoding the Catalytic Domains of MMP-ABT Protein: The plasmid containing clone 907334 was used as template in PCR reactions to generate DNA fragments encoding the clone 907334 protein for introduction into two eukaryotic expression vectors, pcDNA3.1 (Invitrogen, San Diego, Calif.) and pCINeo (Promega, Madison, Wis.). The two upstream primers used in PCR reactions, SEQ ID NO:3 (5'-GTATCTCTAGACACCATGTTTGCAAAGCAA-GGTAACAAATGGTACAAGC-3') and SEQ ID NO:4 (5'-GTATCTCTAGACACCATGAAGGTTCTGTGGGCT-GCGTTGCTGGTCACATTCCTGGCAGGAT-GCCAGGCCTTTGCAAAGCAAGGTAACAAATGG-3') contained sequences to create an XbaI restriction enzyme site, a Kozak consensus sequence for translation initiation, an ATG start codon, and a sequence of nucleotides from nucleotide position 214 to nucleotide position 244 of SEQ ID NO:1, which corresponded to the N-terminus of the putative catalytic domain of the enzyme. SEQ ID NO:4 also contained a sequence which encodes a signal peptide (from the secreted protein, apolipoprotein E), for transport of the translated protein into the secretory pathway. The signal peptide sequence was placed upstream from and in frame with the sequence encoding the N-terminus of the putative catalytic domain. Downstream primers used in PCR reactions were either SEQ ID NO:5 (5'-GTACTTCTAGACTACTTGTCATCGTCGTCCTTG-TAGTCACCACCGAACAGGGCGCTCCCCGAGTTG-GCATGCC-3') which encodes an epitope recognized by anti-FLAG M2, (available from Sigma Biosciences, St. Louis, Mo.) or SEQ ID NO :6 (5'-GTACTTCTAGAGATCTTCTTCACTGATCA-GCTTCTGTTCACCACCGAACAGGGCGCTCCCCGA-GTTGGCATGCC-3') which encodes an epitope recognized by anti-c-Myc (Santa Cruz Biotechnology, Santa Cruz, Calif.). In both downstream primers, these epitope sequences were in frame with the last codon in the open reading frame of the cDNA and were followed by a stop codon (TGA) and an XbaI restriction enzyme site.

PCR amplifications were performed using primers sets SEQ ID NOS:3 and 5, SEQ ID NOS:3 and 6, SEQ ID NOS:4 and 5 and SEQ ID NOS:4 and 6 under standard PCR conditions, i.e. in a total reaction volume of 50 μL containing 200 μM of each dNTP wherein N was A, T, G and C, 1 μM of each primer, ~50 ng template DNA and 1 unit of Ampli-Taq DNA polymerase (Perkin Elmer, Norwalk, Conn.). Amplifications were performed for a total of 35 cycles (1 cycle=94° C. for 1 min, 60° C. for 1 min, and 72° C. for 2 min). After amplification, PCR products were digested with XbaI, gel purified, and ligated into the XbaI site of pcDNA3.1 and pCINeo. After transformation of the ligated DNA into appropriate bacterial hosts (for example DH5a), plasmid DNA was prepared from individual clones and subjected to restriction enzyme and sequence analysis to identify clones that contained clone 907334 DNA with the correct sequence and in the proper orientation.

To generate a full length clone, clone 554936 was subsequently moved as an EcoRI/NotI fragment into the pcDNA3.1. The plasmid was named MMP-ABT full-length (abbreviated MMP-ABT FL).

B. Transfection of MMP-ABT DNA Expression Vectors into HEK293 Cells: Expression of MMP-ABT constructs in HEK293 cells is achieved by transfection using a modified calcium-phosphate procedure (Chen and Okayama, *Mol. Cell. Biol.* 7: 2745–2752, 1987). HEK-293 cells (ATCC CRL1573) are grown in minimal essential medium (MEM) containing 10% fetal bovine serum (FBS) and antibiotic/antimycotic solution at 37° C. in 5% $CO_2$, 95% $O_2$. Cells are transfected with purified plasmid MMP-ABT DNA (20 μg/2.5×10$^6$ cells/10 cm plate). For stable transfections, cells are grown in the presence of G418 and MEM/FBS. For both transient and stable transfections, serum-free media is harvested 3 days after medium replacement.

C. Detection of MMP-ABT protein (Western blot): Media from transfected cells is mixed (vol:vol, 1:1) with 2× denaturing buffer (10 mM Tris-HCl, pH6.8, 4% SDS, 20% glycerol, 1% β-mercaptoethanol, 0.02% bromphenol blue) and denatured by heating 5 minutes, 95° C. Aliquots (20 μl) of each sample are electrophoresed for ~1 hour on a 10–20% Tris-tricine minigel (10×10 cm) at ~50 mA constant current. Gels are transferred to PVDF membranes by electroblotting at 200 mA for 1.5 hours. Non-specific binding sites on PVDF membranes are blocked for 1 hour at room temperature with 5% nonfat dry milk in Tris-buffered saline containing Tween-20 (TBS-Tween) (20 mM Tris, pH 7.6, 140 mM NaCl, 0.1% Tween-20). Blots are then incubated for 1 hour at room temperature in TBS-Tween/5% milk containing an appropriate amount of primary antibody (either anti-FLAG or anti-c-Myc). Blots are washed in 3 changes of TBS-Tween for a total of 45 minutes at room temperature before incubating with the detection antibody (1:1000 dilution) for 1 hour at room temperature in TBS-Tween/5% milk. Blots are again washed in 3 changes of TBS-Tween for 45 minutes at room temperature. Protein bands are visualized by autoradiography using ECL Western blotting detection reagents (Amersham, Arlington Heights, Ill.).

EXAMPLE 4

Assays of Enzymatic Activity of MMP-ABT

Purification of the MMP-ABT protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, medium from transfected HEK293 cells is exchanged into 50 mM Tris-HCl pH 7.5, 150 mM NaCl buffer using a Sephadex G-25 (Pharmacia Biotech Inc., Uppsala, Sweden) column. Protein in this buffer is applied to the anti-FLAG M2 antibody affinity column, non-binding protein is eluted by washing the column with 50 mM Tris-HCl pH 7.5, 150 mM NaCl buffer, and bound protein is eluted using an excess of FLAG peptide in 50 mM Tris-HCl, pH 7.5, 150 mM NaCl. The excess FLAG peptide is removed by size exclusion chromatography and column fractions containing MMP-ABT protein are dialyzed in 50 mM Tris-HCl, pH 7.5, 150 mM NaCl, 10 MM CaCl.

Assays to determine enzyme activity are performed using a fluorogenic peptide substrate Gly-Glu(EDANS)-Gly-Pro-Leu-Gly-Leu-Tyr-Ala-Lys(DABCYL)-Gly (SEQ ID NO:13). SEQ ID NO:13 was synthesized and purified according the procedure of E.D. Matayoshi et al., *Science*, 247: 954–958, 1990). Hydrolysis of the Gly-Leu bond in SEQ ID NO:13 results in a 40-fold increase in fluorescence.

Purified MMP-ABT protein from transfected HEK293 cell medium is serially diluted and incubated in microtiter plate wells with 100 μM fluorogenic peptide substrate, 50 mM Tris-HCl, pH 7.5, 150 mM NaCl in a final volume of 150 μL. Assay mixtures are incubated at room temperature and the progress of the reaction monitored for up to 1 hour in an Titertek Fluoroskan II instrument (ICN Biomedicals, Huntsville, Ala.) with an excitation filter set at 335 nm and emission filter at 485 nm. Background fluorescence is determined using identical reactions in the absence of MMP-ABT. Data is collected online with a Macintosh computer using DELTA SOFT II, version 4.0 (BioMetallics, Inc., Princeton, N.J.). Nonlinear curve fitting is performed using KaleidaGraph (Synergy Software, Reading, Pa.). Compounds which potentially inhibit MMP-ABT activity are screened by including serial dilutions of each compound with the above reaction and comparing the MMP-ABT enzymatic activity in the presence and absence of compound.

EXAMPLE 5

Proteolysis of Pro-MMPs by MMP-ABT

Interaction of MMP-ABT with other MMPs is determined by incubation of purified active MMP-ABT with the zymogen (pro-peptide) forms of Gelatinase-A (72 kD) [MMP-2] and Gelatinase-B (92 kD) [MMP-9]. Gelatinase-A and Gelatinase-B are isolated from HT-1080 cell cultures stimulated with TNFa as described in *J. Antibiotics* 45: 1733–1737, 1992 and *Biochem. J.* 285: 603–611, 1992. After 1 hour incubation at 37° C. in buffer containing 50 mM Tris-HCl, pH 7.5, 150 mM NaCl and approximately 250 ng of each enzyme, aliquots are removed and electrophoresed on 10–20% Tris-Tricine gels. Western blots of gels are performed using antibodies to Gelatinse A and Gelatinase B (Oncogene Science, Cambridge, Mass.) as described above and proteolysis is indicated by the presence of bands of lower molecular weight relative to the pro-enzyme forms of Gelatinase A and Gelatinase B.

EXAMPLE 6

Production of Polyclonal Antibodies to MMP-ABT

Synthetic peptides (SEQUENCE ID NOS:14–17, see Table 1 below) are prepared based upon the predicted amino acid sequence of the MMP-ABT polypeptide.

TABLE I

| Sequence | SEQ ID NO: |
|---|---|
| RHRTKMRRKKRFAKQGN | 14 |
| FQGDHNDGLGNAFDG | 15 |
| RSLQDWGGIPEEVSGALPRPDGSII | 16 |
| ATELPWMGCWHANSGSALF | 17 |

Peptides are synthesized on an ABI Peptide Synthesizer (Applied Biosystems, Foster City, Calif.), using standard reagents and conditions known in the art for solid phase peptide synthesis (see for example, Stewart, J. M., and Young, D. J., *Solid Phase Peptide Synthesis*, W.H. Freeman Co., San Francisco, 1963). Cleavage of the peptide from the resin and final deprotection of the peptide are achieved by adding the resin to 20 ml trifluoroacetic acid (TFA), 0.3 ml water, 0.2 ml ethanedithiol, 0.2 ml thioanisole and 100 mg phenol, and stirring at room temperature for 1.5 hours. The resin then is filtered by suction and the peptide obtained by precipitation of the TFA solution with ether, followed by filtration. Each peptide is purified via reverse-phase preparative HPLC using a water/acetonitrile/0.1% TFA gradient and lyophilized. The product is confirmed by mass spectrometry.

To generate antigens for immunization, the purified peptides are conjugated to Keyhole Limpet Hemocyanin (KLH) and bovine serum albumin (BSA) using an Imject Activated Immunogen Conjugation Kit (Pierce, Rockford, Ill.) in accordance with the manufacturer's instructions.

Polyclonal antisera are generated using the protocol of the Berkeley Antibody Company (Berkeley, Calif.). Before receiving the first immunization, a sample of preimmune blood (5 ml) is drawn from each of at least 2 rabbits. Afterward, each rabbit is injected subcutaneously with an aliquot of KLH-conjugated peptide (200–500 mg) in Complete Freunds Adjuvant. After 21 days, the immune response is boosted with a second subcutaneous injection of KLH-conjugated peptide (100–250 mg) in Incomplete Freund's Adjuvant. Blood (50 ml) is collected on day 31 and serum tested for reactivity to BSA-coupled peptide using an enzyme linked immunoadsorbant assay (ELISA). Subsequent boosts with KLH-conjugated peptide are given on days 42, 63 and 84 (post injection #1) and production bleeds (50 ml) drawn on days 52, 73 and 94 for testing by ELISA to determine antibody titer. Serum is then stored at −20° C. until further use.

What is claimed:

1. An isolated or purified polynucleotide comprising a nucleotide sequence selected from the group consisting of
   a) the sense sequence of SEQ ID NO:1,
   b) a sequence complementary to the sequence of (a);
   c) sequences that, on expression, encode a polypeptide encoded by the sequences of (a) or (b); and
   d) sequences that
      (i) have at least 90% global sequence identity to the sequences of (a) and (b); and
      (ii) encode MMP-ABT which catalyze the cleavage of a substrate consisting of the amino acid sequence of SEQ ID NO:13.

2. The purified polynucleotide of claim 1 wherein said purified polynucleotide is produced by recombinant techniques.

3. A recombinant expression system comprising the nucleotide sequence of claim 1 operably linked to a control sequence compatible with a desired host.

4. A host cell comprising the recombinant expression system of claim 3.

5. A purified polynucleotide which encodes an MMP-ABT protein having SEQ IND NO:10.

6. A purified polynucleotide which encodes an MMP-ABT protein comprising an amino acid sequence which has at least 90% global sequence identity to SEQ ID NO:10 and catalyzes the cleavage of a substrate consisting of the amino acid sequence of SEQ ID NO:13.

7. A purified polynucleotide encoding an epitope of MMP-APT of SEQ ID NO:10 wherein said epitope is selected from the group consisting of SEQ ID NO:14, SEQ ID NO: 15, SEQ ID NO:16, and SEQ ID NO:17.

* * * * *

SEQUENCE LISTING

<160> NUMBER OF SEQ ID NOS: 35

<210> SEQ ID NO 1
<211> LENGTH: 2275
<212> TYPE: DNA
<213> ORGANISM: Homo sapiens

<400> SEQUENCE: 1

-continued

```
ccacgcgtcc ggctgcccga gccgggctgc accggaggcg cgcgagatggt c gcgcgcgtc      60 ggccttctgc tgcgcgccct gcagctgcta ctgtggggcc acctggacgc c cagcccgcg    120 gagcgcgaag gccaggagct gcgcaaggag cggaggcat tcctagagaa g tacggatac     180 ctcaatgaac aggtccccaa agctcccacc tccactcgat tcagcgatgc c atcagagcg    240 tttcagtggg tgtcccagct acctgtcagc ggcgtgttgg accgcgccac c ctgcgccag   300 atgactcgtc cccgctgcgg ggttacagat accaacagtt atgcggcctg g gctgagagg   360 atcagtgact tgtttgctag acaccggacc aaaatgaggc gtaagaaacg c tttgcaaag   420 caaggtgaca aatggtacaa gcagcacctc tcctaccgcc tggtgaactg g cctgagcat   480 ctgccggagc cggcagttcg gggcgccgtg cgcgccgcct ccagttgtg g agcaacgtc    540 tcagcgctgg agttctggga ggccccagcc acaggccccg ctgacatccg g ctcaccttc   600 ttccaagggg accacaacga tgggctgggc aatgcctttg atggcccagg g ggcgccctg   660 gcgcacgcct tcctgccccg ccgcggcgaa ttttacttcg accaagatga g cgctggtcc   720 ctgagccgcc gccgcgggcg caacctgttc gtggtgctgg cgcacgagat c ggtcacacg   780 cttggcctca cccactcgcc cgcgccgcgc gcgctcatgg cgccctacta c aagaggctg   840 ggccgcgacg cgctgctcag ctgggacgac gtgctggccg tgcagagcct g tatgggaag   900 cccctagggg gctcagtggc cgtccagctc ccaggaaagc tgttcactga c tttgagacc   960 tgggactcct acagccccca aggaaggcgc cctgaaacgc agggccctaa a tactgccac  1020 tcttccttcg atgccatcac tgtagacagg caacagcaac tgtacatttt t aaagggagc  1080 catttctggg aggtggcagc tgatggcaac gtctcagagc cccgtccact g caggaaaga  1140 tgggtcgggc tgccccccaa cattgaggct gcggcagtgt cattgaatga t ggagatttc  1200 tacttcttca aggggggtcg atgctggagg ttccggggcc caagccagt g tggggtctc  1260 ccacagctgt gccgggcagg gggcctgccc cgccatcctg acgccgccct c ttcttccct  1320 cctgtgcgcc gcctcatcct cttcaagggt gcccgctact acgtgctggc c cgaggggga  1380 ctgcaagtga gcccctacta ccccgaagt ctgcaggact ggggaggcat c cctgaggag  1440 gtcagcggcg ccctgccgag gcccgatggc tccatcatct tcttccgaga t gaccgctac  1500 tggcgcctcg accaggccaa actgcaggca accacctcgg gccgctgggc c accgagctg  1560 ccctggatgg gctgctggca tgccaactcg gggagcgccc tgttctgaag g cacctcctc  1620 acctcagaaa ctggtggtgc tctcaggca aaatcatgtt ccccaccccc g gggcagaac  1680 ccctcttaga agcctctgag tccctctgca gaagaccggg cagcaaagcc t ccatctgga  1740 agtctgtctg cctttgttcc ttgaagaatg cagcattgtc tttgtctgtc c ccaccacat  1800 ggaggtgggg gtgggatcaa tcttaggaaa agcaaaaaag ggtcccagat c ccttggccc  1860 tttcctccga ggacttctat cctcccccagg cctttgtttc ttcggctaaa g gtacagttc  1920 ctttcaagag gtaacagcac tgggatccaa gcaggggat gaaaaactca g cagagaaat  1980 tcgagaccat tttgcaagac tgtgcccttc tcctcaggac ccctggctc a gttcttgaa  2040 aaacggtgtc atatttagtc agaggcccca ccccaggaa gcatggatgg g gatgaaggc  2100 acaggcgtct ccaacctcag aggcccttg tggggtcagg acacagagtg g gagggagac  2160 tgatgcaggc ctaccagtcc ctggcttttt gtctggggct ggaataaaga g gtgccttca  2220 gctggtgggc cgagaggcag gaagcaaaaa aaaaaaaaaa aaaaaaaaaa a aaaa       2275
```

<210> SEQ ID NO 2
<211> LENGTH: 2275

-continued

```
<212> TYPE: DNA
<213> ORGANISM: Homo sapiens

<400> SEQUENCE: 2
ggtgcgcagg ccgacgggct cggcccgacg tggcctccgc cgctctacca g cgcgcgcag       60 ccggaagacg acgcgcggga cgtcgacgat gacaccccgg tggacctgcg g gtcgggcgc      120 ctcgcgcttc cggtcctcga cgcgttcctc cgcctccgta aggatctctt c atgcctatg      180 gagttacttg tccaggggtt tcgagggtgg aggtgagcta agtcgctacg g tagtctcgc      240 aaagtcaccc acagggtcga tggacagtcg ccgcacaacc tggcgcggtg g gacgcggtc      300 tactgagcag gggcgacgcc ccaatgtcta tggttgtcaa tacgccggac c cgactctcc      360 tagtcactga acaaacgatc tgtggcctgg ttttactccg cattctttgc g aaacgtttc      420 gttccactgt ttaccatgtt cgtcgtggag aggatggcgg accacttgac c ggactcgta      480 gacggcctcg gccgtcaagc cccgcggcac gcgcggcgga aggtcaacac c tcgttgcag      540 agtcgcgacc tcaagaccct ccggggtcgg tgtccgggc gactgtaggc c gagtggaag       600 aaggttcccc tggtgttgct acccgacccg ttacggaaac taccgggtcc c ccgcgggac      660 cgcgtgcgga aggacggggc ggcgccgctt aaaatgaagc tggttctact c gcgaccagg      720 gactcggcgg cggcgcccgc gttggacaag caccacgacc gcgtgctcta g ccagtgtgc      780 gaaccggagt gggtgagcgg gcgcggcgcg cgcgagtacc gcgggatgat g ttctccgac      840 ccggcgctgc gcgacgagtc gaccctgctg cacgaccggc acgtctcgga c ataccccttc     900 ggggatcccc cgagtcaccg gcaggtcgag ggtccttttcg acaagtgact g aaactctgg     960 accctgagga tgtcgggggt tccttccgcg ggactttgcg tcccgggatt t atgacggtg     1020 agaaggaagc tacggtagtg acatctgtcc gttgtcgttg acatgtaaaa a tttccctcg     1080 gtaaagaccc tccaccgtcg actaccgttg cagagtctcg gggcaggtga c gtcctttct     1140 acccagcccg acgggggggtt gtaactccga cgccgtcaca gtaacttact a cctctaaag    1200 atgaagaagt tccccccagc tacgacctcc aaggccccgg ggttcggtca c ccccagag     1260 ggtgtcgaca cggcccgtcc cccggacggg gcggtaggac tgcggcggga g aagaaggga    1320 ggacacgcgg cggagtagga gaagttccca cgggcgatga tgcacgaccg g gctccccct    1380 gacgttcacc tcgggatgat gggggcttca gacgtcctga cccctccgta g ggactcctc    1440 cagtcgccgc gggacggctc cgggctaccg agtagtaga agaaggctct a ctggcgatg     1500 accgcggagc tggtccggtt tgacgtccgt tggtggagcc cggcgacccg g tggctcgac    1560 gggacctacc cgacgaccgt acggttgagc ccctcgcggg acaagacttc c gtggaggag    1620 tggagtcttt gaccaccacg agagtcccgt tttagtacaa ggggtggggg c cccgtcttg    1680 gggagaatct tcggagactc agggagacgt cttctggccc gtcgtttcgg a ggtagacct    1740 tcagacagac ggaaacaagg aacttcttac gtcgtaacag aaacagacag g ggtggtgta    1800 cctccacccc caccctagtt agaatccttt tcgttttttc ccagggtcta g gaaccggg     1860 aaaggaggct cctgaagata ggaggggtcc ggaaacaaag aagccgattt c catgtcaag    1920 gaaagttctc cattgtcgtg accctaggtt cgtcccccta cttttgagt c gtctcttta    1980 agctctggtk aaacgttctg acacgggaag aggagtcctg ggggaccgag t caagaactt    2040 tttgccacag tataaatcag tctccggggt ggggtcctt cgtacctacc c ctacttccg     2100 tgtccgcaga ggttggagtc tccggaaaac accccagtcc tgtgtctcac c ctccctctg    2160 actacgtccg gatggtcagg gaccgaaaaa cagaccccga ccttatttct c cacggaagt    2220
```

-continued cgaccacccg gctctccgtc cttcgttttt tttttttttt tttttttttt t tttt    2275

<210> SEQ ID NO 3
<211> LENGTH: 49
<212> TYPE: DNA
<213> ORGANISM: Artificial Sequence
<220> FEATURE:
<223> OTHER INFORMATION: Upstream primer

<400> SEQUENCE: 3
gtatctctag acaccatgtt tgcaaagcaa ggtaacaaat ggtacaagc    49

<210> SEQ ID NO 4
<211> LENGTH: 93
<212> TYPE: DNA
<213> ORGANISM: Artificial Sequence
<220> FEATURE:
<223> OTHER INFORMATION: Upstream primer

<400> SEQUENCE: 4
gtatctctag acaccatgaa ggttctgtgg gctgcgttgc tggtcacatt c ctggcagga    60 tgccaggcct ttgcaaagca aggtaacaaa tgg    93

<210> SEQ ID NO 5
<211> LENGTH: 73
<212> TYPE: DNA
<213> ORGANISM: Artificial Sequence
<220> FEATURE:
<223> OTHER INFORMATION: Downstream primer

<400> SEQUENCE: 5
gtacttctag actacttgtc atcgtcgtcc ttgtagtcac caccgaacag g gcgctcccc    60 gagttggcat gcc    73

<210> SEQ ID NO 6
<211> LENGTH: 74
<212> TYPE: DNA
<213> ORGANISM: Artificial Sequence
<220> FEATURE:
<223> OTHER INFORMATION: Downstream primer

<400> SEQUENCE: 6
gtacttctag agatcttctt cactgatcag cttctgttca ccaccgaaca g ggcgctccc    60 cgagttggca tgcc    74

<210> SEQ ID NO 7
<211> LENGTH: 820
<212> TYPE: PRT
<213> ORGANISM: Artificial Sequence
<220> FEATURE:
<223> OTHER INFORMATION: MMP Consensus Sequence
<223> OTHER INFORMATION: Xaa = Unknown or Other in each instance

<400> SEQUENCE: 7

Xaa Xaa Xaa Xaa Xaa Xaa Xaa Xaa Xaa Xaa X aa Xaa Xaa Xaa Xaa Xaa
 1               5                  10                  15

Xaa Xaa Xaa Leu Xaa Xaa Leu Leu Leu Leu X aa Xaa Xaa Xaa Xaa Xaa
            20                  25                  30

Xaa Leu Xaa Xaa Xaa Xaa Xaa Xaa Xaa Xaa X aa Xaa Xaa Xaa Xaa Xaa
        35                  40                  45

Xaa Xaa Xaa Xaa Xaa Xaa Xaa Tyr Leu Xaa X aa Tyr Tyr Xaa Leu Xaa
    50                  55                  60

-continued

```
Xaa Xaa Xaa Xaa Xaa Xaa Xaa Xaa Xaa Xaa Xaa Xaa Xaa Xaa Xaa
 65                  70                  75                  80

Xaa Xaa Xaa Leu Xaa Xaa Met Gln Xaa Phe Phe Gly Leu Xaa Val Thr
                 85                  90                  95

Gly Lys Leu Asp Xaa Xaa Thr Leu Glu Xaa Met Xaa Lys Pro Arg Cys
                100                 105                 110

Gly Val Pro Asp Xaa Xaa Xaa Xaa Xaa Xaa Xaa Xaa Val Xaa Xaa
                115                 120                 125

Phe Xaa Leu Xaa Pro Xaa Xaa Pro Lys Trp Xaa Xaa Xaa Xaa Thr
130                 135                 140

Tyr Arg Ile Xaa Asn Tyr Thr Pro Asp Leu Xaa Xaa Xaa Xaa Val Asp
145                 150                 155                 160

Xaa Ala Ile Xaa Lys Ala Phe Xaa Val Trp Ser Xaa Val Thr Pro Leu
                165                 170                 175

Xaa Phe Xaa Xaa Val Xaa Xaa Xaa Xaa Xaa Xaa Xaa Xaa Glu Gly
                180                 185                 190

Xaa Ala Asp Ile Met Ile Xaa Phe Ala Xaa Xaa Glu His Gly Asp Xaa
                195                 200                 205

Xaa Pro Phe Asp Gly Pro Gly Xaa Leu Ala His Ala Phe Xaa Pro
210                 215                 220

Gly Pro Gly Ile Gly Gly Asp Ala His Phe Asp Asp Asp Glu Xaa Trp
225                 230                 235                 240

Thr Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa Xaa
                370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Gly Xaa Asn Leu Phe Leu Val Ala Ala His Glu
                420                 425                 430

Xaa Gly His Ser Leu Gly Leu Xaa His Ser Xaa Asp Pro Xaa Ala Leu
                435                 440                 445

Met Tyr Pro Xaa Tyr Xaa Xaa Phe Xaa Asp Xaa Xaa Xaa Phe Xaa Leu
                450                 455                 460

Xaa Xaa Asp Asp Ile Xaa Gly Ile Gln Xaa Leu Tyr Gly Xaa Xaa Xaa
465                 470                 475                 480

Xaa Xaa Xaa Xaa Xaa Xaa Xaa Xaa Xaa Xaa Xaa Xaa Xaa Xaa Xaa
```

```
                         485                 490                 495

Xaa Xaa Xaa Xaa Xaa Xaa Xaa Xaa Xaa Xaa Xaa Xaa Xaa Xaa Xaa
                500                 505                 510

Xaa Xaa Xaa Xaa Xaa Xaa Xaa Xaa Xaa Xaa Xaa Xaa Xaa Xaa Xaa
                515                 520                 525

Xaa Xaa Xaa Xaa Xaa Xaa Xaa Xaa Pro Xaa Xaa Cys Asp Xaa Xaa Xaa
                530                 535                 540

Xaa Xaa Xaa Xaa Xaa Xaa Xaa Xaa Phe Asp Ala Ile Xaa Xaa Xaa
545                 550                 555                 560

Arg Gly Glu Xaa Phe Phe Lys Asp Arg Phe Phe Trp Arg Xaa Xaa
                565                 570                 575

Xaa Xaa Xaa Xaa Xaa Xaa Xaa Xaa Xaa Xaa Xaa Leu Ile Xaa Xaa Phe
                580                 585                 590

Trp Pro Xaa Leu Pro Xaa Xaa Ile Asp Ala Ala Tyr Glu Xaa Xaa Xaa
                595                 600                 605

Xaa Xaa Xaa Val Phe Phe Phe Lys Gly Xaa Xaa Tyr Trp Xaa Tyr Xaa
                610                 615                 620

Gly Xaa Xaa Xaa Xaa Xaa Gly Tyr Pro Xaa Xaa Ile Xaa Xaa Xaa Leu
625                 630                 635                 640

Gly Phe Pro Xaa Xaa Val Xaa Xaa Ile Asp Ala Ala Xaa Xaa Xaa Xaa
                645                 650                 655

Xaa Xaa Xaa Xaa Lys Thr Tyr Phe Phe Xaa Xaa Xaa Xaa Tyr Trp Arg
                660                 665                 670

Tyr Asp Glu Xaa Xaa Xaa Xaa Met Asp Pro Gly Tyr Pro Lys Xaa Ile
                675                 680                 685

Xaa Xaa Xaa Phe Xaa Gly Ile Xaa Xaa Xaa Val Asp Ala Val Phe Xaa
                690                 695                 700

Xaa Xaa Xaa Xaa Gly Phe Xaa Tyr Phe Phe Xaa Gly Xaa Xaa Xaa Tyr
705                 710                 715                 720

Xaa Phe Xaa Xaa Xaa Xaa Xaa Xaa Val Xaa Xaa Xaa Xaa Xaa Xaa
                725                 730                 735

Xaa Xaa Xaa Xaa Trp Leu Xaa Cys Xaa Xaa Xaa Xaa Xaa Xaa Xaa
                740                 745                 750

Xaa Xaa Xaa Xaa Xaa Xaa Xaa Xaa Xaa Xaa Xaa Xaa Xaa Xaa Xaa
                755                 760                 765

Xaa Xaa Xaa Xaa Xaa Xaa Xaa Xaa Xaa Xaa Xaa Xaa Xaa Xaa Xaa
                770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
                805                 810                 815

Xaa Xaa Xaa Xaa
        820

<210> SEQ ID NO 8
<211> LENGTH: 7
<212> TYPE: PRT
<213> ORGANISM: Unknown
<220> FEATURE:
<223> OTHER INFORMATION: Putative cysteine switch motif

<400> SEQUENCE: 8

Pro Arg Cys Gly Val Thr Asp
 1               5
```

```
<210> SEQ ID NO 9
<211> LENGTH: 4
<212> TYPE: PRT
<213> ORGANISM: Unknown
<220> FEATURE:
<223> OTHER INFORMATION: Putative furin recognitio n site

<400> SEQUENCE: 9

Arg Lys Lys Arg
 1

<210> SEQ ID NO 10
<211> LENGTH: 520
<212> TYPE: PRT
<213> ORGANISM: Homo sapiens

<400> SEQUENCE: 10

Met Val Ala Arg Val Gly Leu Leu Arg A la Leu Gln Leu Leu Leu
 1               5                  10                  15

Trp Gly His Leu Asp Ala Gln Pro Ala G lu Arg Gly Gln Glu Leu
                20                  25                  30

Arg Lys Glu Ala Glu Ala Phe Leu Glu Lys T yr Gly Tyr Leu Asn Glu
            35                  40                  45

Gln Val Pro Lys Ala Pro Thr Ser Thr Arg P he Ser Asp Ala Ile Arg
        50                  55                  60

Ala Phe Gln Trp Val Ser Gln Leu Pro Val S er Gly Val Leu Asp Arg
65                  70                  75                  80

Ala Thr Leu Arg Gln Met Thr Arg Pro Arg C ys Gly Val Thr Asp Thr
                85                  90                  95

Asn Ser Tyr Ala Ala Trp Ala Glu Arg Ile S er Asp Leu Phe Ala Arg
            100                 105                 110

His Arg Thr Lys Met Arg Arg Lys Arg P he Ala Lys Gln Gly Asp
        115                 120                 125

Lys Trp Tyr Lys Gln His Leu Ser Tyr Arg L eu Val Asn Trp Pro Glu
    130                 135                 140

His Leu Pro Glu Pro Ala Val Arg Gly Ala V al Arg Ala Ala Phe Gln
145                 150                 155                 160

Leu Trp Ser Asn Val Ser Ala Leu Glu Phe T rp Glu Ala Pro Ala Thr
                165                 170                 175

Gly Pro Ala Asp Ile Arg Leu Thr Phe Phe G ln Gly Asp His Asn Asp
            180                 185                 190

Gly Leu Gly Asn Ala Phe Asp Gly Pro Gly G ly Ala Leu Ala His Ala
        195                 200                 205

Phe Leu Pro Arg Gly Glu Phe Tyr Phe A sp Gln Asp Glu Arg Trp
    210                 215                 220

Ser Leu Ser Arg Arg Gly Arg Asn Leu P he Val Val Leu Ala His
225                 230                 235                 240

Glu Ile Gly His Thr Leu Gly Leu Thr His S er Pro Ala Pro Arg Ala
                245                 250                 255

Leu Met Ala Pro Tyr Tyr Lys Arg Leu Gly A rg Asp Ala Leu Leu Ser
            260                 265                 270

Trp Asp Asp Val Leu Ala Val Gln Ser Leu T yr Gly Lys Pro Leu Gly
        275                 280                 285

Gly Ser Val Ala Val Gln Leu Pro Gly Lys L eu Phe Thr Asp Phe Glu
    290                 295                 300

Thr Trp Asp Ser Tyr Ser Pro Gln Gly Arg A rg Pro Glu Thr Gln Gly
305                 310                 315                 320
```

```
Pro Lys Tyr Cys His Ser Ser Phe Asp Ala Ile Thr Val Asp Arg Gln
                325                 330                 335
Gln Gln Leu Tyr Ile Phe Lys Gly Ser His Phe Trp Glu Val Ala Ala
            340                 345                 350
Asp Gly Asn Val Ser Glu Pro Arg Pro Leu Gln Glu Arg Trp Val Gly
        355                 360                 365
Leu Pro Pro Asn Ile Glu Ala Ala Val Ser Leu Asn Asp Gly Asp
    370                 375                 380
Phe Tyr Phe Phe Lys Gly Gly Arg Cys Trp Arg Phe Arg Gly Pro Lys
385                 390                 395                 400
Pro Val Trp Gly Leu Pro Gln Leu Cys Arg Ala Gly Gly Leu Pro Arg
                405                 410                 415
His Pro Asp Ala Ala Leu Phe Phe Pro Pro Val Arg Arg Leu Ile Leu
            420                 425                 430
Phe Lys Gly Ala Arg Tyr Tyr Val Leu Ala Arg Gly Gly Leu Gln Val
        435                 440                 445
Glu Pro Tyr Tyr Pro Arg Ser Leu Gln Asp Trp Gly Gly Ile Pro Glu
    450                 455                 460
Glu Val Ser Gly Ala Leu Pro Arg Pro Asp Gly Ser Ile Ile Phe Phe
465                 470                 475                 480
Arg Asp Asp Arg Tyr Trp Arg Leu Asp Gln Ala Lys Leu Gln Ala Thr
                485                 490                 495
Thr Ser Gly Arg Trp Ala Thr Glu Leu Pro Trp Met Gly Cys Trp His
            500                 505                 510
Ala Asn Ser Gly Ser Ala Leu Phe
        515                 520

<210> SEQ ID NO 11
<211> LENGTH: 7
<212> TYPE: PRT
<213> ORGANISM: Unknown
<220> FEATURE:
<223> OTHER INFORMATION: Consensus cysteine switch  motif

<400> SEQUENCE: 11

Pro Arg Cys Gly Val Pro Asp
1               5

<210> SEQ ID NO 12
<211> LENGTH: 12
<212> TYPE: PRT
<213> ORGANISM: Unknown
<220> FEATURE:
<223> OTHER INFORMATION: Zinc binding consensus sequence
<223> OTHER INFORMATION: Xaa = Unknown or Other at position 3
<223> OTHER INFORMATION: Xaa = Unknown or Other at postion 6
<223> OTHER INFORMATION: Xaa = Unknown or Other at position 10

<400> SEQUENCE: 12

His Glu Xaa Gly His Xaa Leu Gly Leu Xaa His Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Fluorogenic peptide subst rate

<400> SEQUENCE: 13
```

```
Gly Glu Gly Pro Leu Gly Leu Tyr Ala Lys Gly
 1               5                  10
```

<210> SEQ ID NO 14
<211> LENGTH: 17
<212> TYPE: PRT
<213> ORGANISM: Artificial Sequence
<220> FEATURE:
<223> OTHER INFORMATION: Synthetic peptides

<400> SEQUENCE: 14

```
Arg His Arg Thr Lys Met Arg Lys Lys Arg Phe Ala Lys Gln Gly
 1               5                  10                  15

Asn
```

<210> SEQ ID NO 15
<211> LENGTH: 15
<212> TYPE: PRT
<213> ORGANISM: Artificial Sequence
<220> FEATURE:
<223> OTHER INFORMATION: Synthetic peptides

<400> SEQUENCE: 15

```
Phe Gln Gly Asp His Asn Asp Gly Leu Gly Asn Ala Phe Asp Gly
 1               5                  10                  15
```

<210> SEQ ID NO 16
<211> LENGTH: 25
<212> TYPE: PRT
<213> ORGANISM: Artificial Sequence
<220> FEATURE:
<223> OTHER INFORMATION: Synthetic peptides

<400> SEQUENCE: 16

```
Arg Ser Leu Gln Asp Trp Gly Gly Ile Pro Glu Glu Val Ser Gly Ala
 1               5                  10                  15

Leu Pro Arg Pro Asp Gly Ser Ile Ile
                20                  25
```

<210> SEQ ID NO 17
<211> LENGTH: 19
<212> TYPE: PRT
<213> ORGANISM: Artificial Sequence
<220> FEATURE:
<223> OTHER INFORMATION: Synthetic peptides

<400> SEQUENCE: 17

```
Ala Thr Glu Leu Pro Trp Met Gly Cys Trp His Ala Asn Ser Gly Ser
 1               5                  10                  15

Ala Leu Phe
```

<210> SEQ ID NO 18
<211> LENGTH: 508
<212> TYPE: PRT
<213> ORGANISM: Homo sapiens

<400> SEQUENCE: 18

```
Met Asn Cys Gln Gln Leu Trp Leu Gly Phe Leu Leu Pro Met Thr Val
 1               5                  10                  15

Ser Gly Arg Val Leu Gly Leu Ala Glu Val Ala Pro Val Asp Tyr Leu
                20                  25                  30

Ser Gln Tyr Gly Tyr Leu Gln Lys Pro Leu Glu Gly Ser Asn Asn Phe
            35                  40                  45
```

-continued

```
Lys Pro Glu Asp Ile Thr Glu Ala Leu Arg Ala Phe Gln Glu Ala Ser
 50                  55                  60
Glu Leu Pro Val Ser Gly Gln Leu Asp Asp Ala Thr Arg Ala Arg Met
 65                  70                  75                  80
Arg Gln Pro Arg Cys Gly Leu Glu Asp Pro Phe Asn Gln Lys Thr Leu
                 85                  90                  95
Lys Tyr Leu Leu Leu Gly Arg Trp Arg Lys His Leu Thr Phe Arg
            100                 105                 110
Ile Leu Asn Leu Pro Ser Thr Leu Pro Pro His Thr Ala Arg Ala Ala
            115                 120                 125
Leu Arg Gln Ala Phe Gln Asp Trp Ser Asn Val Ala Pro Leu Thr Phe
130                 135                 140
Gln Glu Val Gln Ala Gly Ala Ala Asp Ile Arg Leu Ser Phe His Gly
145                 150                 155                 160
Arg Gln Ser Ser Tyr Cys Ser Asn Thr Phe Asp Gly Pro Gly Arg Val
                165                 170                 175
Leu Ala His Ala Asp Ile Pro Glu Leu Gly Ser Val His Phe Asp Glu
                180                 185                 190
Asp Glu Phe Trp Thr Glu Gly Thr Tyr Arg Gly Val Asn Leu Arg Ile
            195                 200                 205
Ile Ala Ala His Glu Val Gly His Ala Leu Gly Leu Gly His Ser Arg
            210                 215                 220
Tyr Ser Gln Ala Leu Met Ala Pro Val Tyr Glu Gly Tyr Arg Pro His
225                 230                 235                 240
Phe Lys Leu His Pro Asp Asp Val Ala Gly Ile Gln Ala Leu Tyr Gly
                245                 250                 255
Lys Lys Ser Pro Val Ile Arg Asp Glu Glu Glu Glu Thr Glu Leu
                260                 265                 270
Pro Thr Val Pro Pro Val Pro Thr Glu Pro Ser Pro Met Pro Asp Pro
            275                 280                 285
Cys Ser Ser Glu Leu Asp Ala Met Met Leu Gly Pro Arg Gly Lys Thr
            290                 295                 300
Tyr Ala Phe Lys Gly Asp Tyr Val Trp Thr Val Ser Asp Ser Gly Pro
305                 310                 315                 320
Gly Pro Leu Phe Arg Val Ser Ala Leu Trp Glu Gly Leu Pro Gly Asn
                325                 330                 335
Leu Asp Ala Ala Val Tyr Ser Pro Arg Thr Gln Trp Ile His Phe Phe
            340                 345                 350
Lys Gly Asp Lys Val Trp Arg Tyr Ile Asn Phe Lys Met Ser Pro Gly
            355                 360                 365
Phe Pro Lys Lys Leu Asn Arg Ser Glu Pro Asn Leu Asp Ala Ala Leu
370                 375                 380
Tyr Trp Pro Leu Asn Gln Lys Val Phe Leu Phe Lys Gly Ser Gly Tyr
385                 390                 395                 400
Trp Gln Trp Asp Glu Leu Ala Arg Thr Asp Phe Ser Ser Tyr Pro Lys
                405                 410                 415
Pro Ile Lys Gly Leu Phe Thr Gly Val Pro Asn Gln Pro Ser Ala Ala
                420                 425                 430
Met Ser Trp Gln Asp Gly Arg Val Tyr Phe Phe Lys Gly Lys Val Tyr
            435                 440                 445
Trp Arg Leu Asn Gln Gln Leu Arg Val Glu Lys Gly Tyr Pro Arg Asn
450                 455                 460
Ile Ser His Asn Trp Met His Cys Arg Pro Arg Thr Ile Asp Thr Thr
```

```
                465                 470                 475                 480
Pro Ser Gly Gly Asn Thr Thr Pro Ser Gly T hr Gly Ile Thr Leu Asp
                    485                 490                 495

Thr Thr Leu Ser Ala Thr Glu Thr Thr Phe G lu Tyr
                500                 505

<210> SEQ ID NO 19
<211> LENGTH: 660
<212> TYPE: PRT
<213> ORGANISM: Homo sapiens

<400> SEQUENCE: 19

Met Glu Ala Leu Met Ala Arg Gly Ala Leu T hr Gly Pro Leu Arg Ala
 1                   5                  10                  15

Leu Cys Leu Leu Gly Cys Leu Leu Ser His A la Ala Ala Ala Pro Ser
                 20                  25                  30

Pro Ile Ile Lys Phe Pro Gly Asp Val Ala P ro Lys Thr Asp Lys Glu
             35                  40                  45

Leu Ala Val Gln Tyr Leu Asn Thr Phe Tyr G ly Cys Pro Lys Glu Ser
         50                  55                  60

Cys Asn Leu Phe Val Leu Lys Asp Thr Leu L ys Lys Met Gln Lys Phe
 65                  70                  75                  80

Phe Gly Leu Pro Gln Thr Gly Asp Leu Asp G ln Asn Thr Ile Glu Thr
                 85                  90                  95

Met Arg Lys Pro Arg Cys Gly Asn Pro Asp V al Ala Asn Tyr Asn Phe
            100                 105                 110

Phe Pro Arg Lys Pro Lys Trp Asp Lys Asn G ln Ile Thr Tyr Arg Ile
        115                 120                 125

Ile Gly Tyr Thr Pro Asp Leu Asp Pro Glu T hr Val Asp Ala Phe
    130                 135                 140

Ala Arg Ala Phe Gln Val Trp Ser Asp Val T hr Pro Leu Arg Phe Ser
145                 150                 155                 160

Arg Ile His Asp Gly Glu Ala Asp Ile Met I le Asn Phe Gly Arg Trp
                165                 170                 175

Glu His Gly Asp Gly Tyr Pro Phe Asp Gly L ys Asp Gly Leu Leu Ala
            180                 185                 190

His Ala Phe Ala Pro Gly Thr Gly Val Gly G ly Asp Ser His Phe Asp
        195                 200                 205

Asp Asp Glu Leu Trp Thr Leu Gly Glu Gly G ln Val Val Arg Val Lys
    210                 215                 220

Tyr Gly Asn Ala Asp Gly Glu Tyr Cys Lys P he Pro Phe Leu Phe Asn
225                 230                 235                 240

Gly Lys Glu Tyr Asn Ser Cys Thr Asp Thr G ly Arg Ser Asp Gly Phe
                245                 250                 255

Leu Trp Cys Ser Thr Thr Tyr Asn Phe Glu L ys Asp Gly Lys Tyr Gly
            260                 265                 270

Phe Cys Pro His Glu Ala Leu Phe Thr Met G ly Gly Asn Ala Glu Gly
        275                 280                 285

Gln Pro Cys Lys Phe Pro Phe Arg Phe Gln G ly Thr Ser Tyr Asp Ser
    290                 295                 300

Cys Thr Thr Glu Gly Arg Thr Asp Gly Tyr A rg Trp Cys Gly Thr Thr
305                 310                 315                 320

Glu Asp Tyr Asp Arg Asp Lys Lys Tyr Gly P he Cys Pro Glu Thr Ala
                325                 330                 335
```

```
Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Ala Asn Tyr Asp Asp Asp
    370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
                420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
            450                 455                 460

Thr Pro Glu Ile Cys Lys Gln Asp Ile Val Phe Asp Gly Ile Ala Gln
465                 470                 475                 480

Ile Arg Gly Glu Ile Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
            515                 520                 525

Glu Glu Lys Ala Val Phe Phe Ala Gly Asn Glu Tyr Trp Ile Tyr Ser
    530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
    610                 615                 620

Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 20
<211> LENGTH: 707
<212> TYPE: PRT
<213> ORGANISM: Homo sapiens

<400> SEQUENCE: 20

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45
```

```
Leu Tyr Arg Tyr Gly Tyr Thr Arg Val Ala Glu Met Arg Gly Glu Ser
    50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                    85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Glu
    195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
        275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
    450                 455                 460
```

-continued

```
Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
            485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
            530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
            610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
            690                 695                 700

Pro Glu Asp
705

<210> SEQ ID NO 21
<211> LENGTH: 477
<212> TYPE: PRT
<213> ORGANISM: Homo sapiens

<400> SEQUENCE: 21

Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
            20                  25                  30

Leu Val Gln Lys Tyr Leu Glu Asn Tyr Asp Leu Lys Lys Asp Val
            35                  40                  45

Lys Gln Phe Val Arg Arg Lys Asp Ser Gly Pro Val Val Lys Lys Ile
    50                  55                  60

Arg Glu Met Gln Lys Phe Leu Gly Leu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
            115                 120                 125
```

-continued

```
Ala Val Asp Ser Ala Val Glu Lys Ala Leu Lys Val Trp Glu Glu Val
        130                 135                 140
Thr Pro Leu Thr Phe Ser Arg Leu Tyr Glu Gly Glu Ala Asp Ile Met
145                 150                 155                 160
Ile Ser Phe Ala Val Arg Glu His Gly Asp Phe Tyr Pro Phe Asp Gly
                165                 170                 175
Pro Gly Asn Val Leu Ala His Ala Tyr Ala Pro Gly Pro Gly Ile Asn
            180                 185                 190
Gly Asp Ala His Phe Asp Asp Glu Gln Trp Thr Lys Asp Thr Thr
        195                 200                 205
Gly Thr Asn Leu Phe Leu Val Ala Ala His Glu Ile Gly His Ser Leu
    210                 215                 220
Gly Leu Phe His Ser Ala Asn Thr Glu Ala Leu Met Tyr Pro Leu Tyr
225                 230                 235                 240
His Ser Leu Thr Asp Leu Thr Arg Phe Arg Leu Ser Gln Asp Asp Ile
                245                 250                 255
Asn Gly Ile Gln Ser Leu Tyr Gly Pro Pro Pro Asp Ser Pro Glu Thr
            260                 265                 270
Pro Leu Val Pro Thr Glu Pro Val Pro Pro Glu Pro Gly Thr Pro Ala
        275                 280                 285
Asn Cys Asp Pro Ala Leu Ser Phe Asp Ala Val Ser Thr Leu Arg Gly
    290                 295                 300
Glu Ile Leu Ile Phe Lys Asp Arg His Phe Trp Arg Lys Ser Leu Arg
305                 310                 315                 320
Lys Leu Glu Pro Glu Leu His Leu Ile Ser Ser Phe Trp Pro Ser Leu
                325                 330                 335
Pro Ser Gly Val Asp Ala Ala Tyr Glu Val Thr Ser Lys Asp Leu Val
            340                 345                 350
Phe Ile Phe Lys Gly Asn Gln Phe Trp Ala Ile Arg Gly Asn Glu Val
        355                 360                 365
Arg Ala Gly Tyr Pro Arg Gly Ile His Thr Leu Gly Phe Pro Pro Thr
    370                 375                 380
Val Arg Lys Ile Asp Ala Ala Ile Ser Asp Lys Glu Lys Asn Lys Thr
385                 390                 395                 400
Tyr Phe Phe Val Glu Asp Lys Tyr Trp Arg Phe Asp Glu Lys Arg Asn
                405                 410                 415
Ser Met Glu Pro Gly Phe Pro Lys Gln Ile Ala Glu Asp Phe Pro Gly
            420                 425                 430
Ile Asp Ser Lys Ile Asp Ala Val Phe Glu Glu Phe Gly Phe Phe Tyr
        435                 440                 445
Phe Phe Thr Gly Ser Ser Gln Leu Glu Phe Asp Pro Asn Ala Lys Lys
    450                 455                 460
Val Thr His Thr Leu Lys Ser Asn Ser Trp Leu Asn Cys
465                 470                 475

<210> SEQ ID NO 22
<211> LENGTH: 476
<212> TYPE: PRT
<213> ORGANISM: Homo sapiens

<400> SEQUENCE: 22

Met Met His Leu Ala Phe Leu Val Leu Leu Cys Leu Pro Val Cys Ser
1               5                   10                  15

Ala Tyr Pro Leu Ser Gly Ala Ala Lys Glu Glu Asp Ser Asn Lys Asp
```

-continued

```
              20                  25                  30
Leu Ala Gln Gln Tyr Leu Glu Lys Tyr Tyr Asn Leu Glu Lys Asp Val
             35                  40                  45
Lys Gln Phe Arg Arg Lys Asp Ser Asn Leu Ile Val Lys Lys Ile Gln
 50                  55                  60
Gly Met Gln Lys Phe Leu Gly Leu Glu Val Thr Gly Lys Leu Asp Thr
 65                  70                  75                  80
Asp Thr Leu Glu Val Met Arg Lys Pro Arg Cys Gly Val Pro Asp Val
                 85                  90                  95
Gly His Phe Ser Ser Phe Pro Gly Met Pro Lys Trp Arg Lys Thr His
                100                 105                 110
Leu Thr Tyr Arg Ile Val Asn Tyr Thr Pro Asp Leu Pro Arg Asp Ala
                115                 120                 125
Val Asp Ser Ala Ile Glu Lys Ala Leu Lys Val Trp Glu Glu Val Thr
130                 135                 140
Pro Leu Thr Phe Ser Arg Leu Tyr Glu Gly Glu Ala Asp Ile Met Ile
145                 150                 155                 160
Ser Phe Ala Val Lys Glu His Gly Asp Phe Tyr Ser Phe Asp Gly Pro
                165                 170                 175
Gly His Ser Leu Ala His Ala Tyr Pro Pro Gly Pro Gly Leu Tyr Gly
                180                 185                 190
Asp Ile His Phe Asp Asp Asp Glu Lys Trp Thr Glu Asp Ala Ser Gly
                195                 200                 205
Thr Asn Leu Phe Leu Val Ala Ala His Glu Leu Gly His Ser Leu Gly
                210                 215                 220
Leu Phe His Ser Ala Asn Thr Glu Ala Leu Met Tyr Pro Leu Tyr Asn
225                 230                 235                 240
Ser Phe Thr Glu Leu Ala Gln Phe Arg Leu Ser Gln Asp Asp Val Asn
                245                 250                 255
Gly Ile Gln Ser Leu Tyr Gly Pro Pro Pro Ala Ser Thr Glu Glu Pro
                260                 265                 270
Leu Val Pro Thr Lys Ser Val Pro Ser Gly Ser Glu Met Pro Ala Lys
                275                 280                 285
Cys Asp Pro Ala Leu Ser Phe Asp Ala Ile Ser Thr Leu Arg Gly Glu
290                 295                 300
Tyr Leu Phe Phe Lys Asp Arg Tyr Phe Trp Arg Arg Ser His Trp Asn
305                 310                 315                 320
Pro Glu Pro Glu Phe His Leu Ile Ser Ala Phe Trp Pro Ser Leu Pro
                325                 330                 335
Ser Tyr Leu Asp Ala Ala Tyr Glu Val Asn Ser Arg Asp Thr Val Phe
                340                 345                 350
Ile Phe Lys Gly Asn Glu Phe Trp Ala Ile Arg Gly Asn Glu Val Gln
                355                 360                 365
Ala Gly Tyr Pro Arg Gly Ile His Thr Leu Gly Phe Pro Pro Thr Ile
                370                 375                 380
Arg Lys Ile Asp Ala Ala Val Ser Asp Lys Glu Lys Lys Lys Thr Tyr
385                 390                 395                 400
Phe Phe Ala Ala Asp Lys Tyr Trp Arg Phe Asp Glu Asn Ser Gln Ser
                405                 410                 415
Met Glu Gln Gly Phe Pro Arg Leu Ile Ala Asp Asp Phe Pro Gly Val
                420                 425                 430
Glu Pro Lys Val Asp Ala Val Leu Gln Ala Phe Gly Phe Phe Tyr Phe
                435                 440                 445
```

```
Phe Ser Gly Ser Ser Gln Phe Glu Phe Asp Pro Asn Ala Arg Met Val
    450                 455                 460

Thr His Ile Leu Lys Ser Asn Ser Trp Leu His Cys
465                 470                 475

<210> SEQ ID NO 23
<211> LENGTH: 469
<212> TYPE: PRT
<213> ORGANISM: Homo sapiens

<400> SEQUENCE: 23

Met His Ser Phe Pro Pro Leu Leu Leu Leu Phe Trp Gly Val Val
  1               5                  10                  15

Ser His Ser Phe Pro Ala Thr Leu Glu Thr Gln Glu Gln Asp Val Asp
                 20                  25                  30

Leu Val Gln Lys Tyr Leu Glu Lys Tyr Tyr Asn Leu Lys Asn Asp Gly
                 35                  40                  45

Arg Gln Val Glu Lys Arg Arg Asn Ser Gly Pro Val Val Glu Lys Leu
 50                  55                  60

Lys Gln Met Gln Glu Phe Phe Gly Leu Lys Val Thr Gly Lys Pro Asp
 65                  70                  75                  80

Ala Glu Thr Leu Lys Val Met Lys Gln Pro Arg Cys Gly Val Pro Asp
                 85                  90                  95

Val Ala Gln Phe Val Leu Thr Glu Gly Asn Pro Arg Trp Glu Gln Thr
                100                 105                 110

His Leu Thr Tyr Arg Ile Glu Asn Tyr Thr Pro Asp Leu Pro Arg Ala
                115                 120                 125

Asp Val Asp His Ala Ile Glu Lys Ala Phe Gln Leu Trp Ser Asn Val
                130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
                180                 185                 190

Gly Asp Ala His Phe Asp Glu Asp Glu Arg Trp Thr Asn Asn Phe Arg
                195                 200                 205

Glu Tyr Asn Leu His Arg Val Ala Ala His Glu Leu Gly His Ser Leu
                210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
                260                 265                 270

Gln Thr Pro Lys Ala Cys Asp Ser Lys Leu Thr Phe Asp Ala Ile Thr
                275                 280                 285

Thr Ile Arg Gly Glu Val Met Phe Phe Lys Asp Arg Phe Tyr Met Arg
                290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
```

```
                    340             345             350
Gly Gln Asn Val Leu His Gly Tyr Pro Lys Asp Ile Tyr Ser Ser Phe
            355             360             365

Gly Phe Pro Arg Thr Val Lys His Ile Asp Ala Ala Leu Ser Glu Glu
        370             375             380

Asn Thr Gly Lys Thr Tyr Phe Phe Val Ala Asn Lys Tyr Trp Arg Tyr
385             390             395             400

Asp Glu Tyr Lys Arg Ser Met Asp Pro Gly Tyr Pro Lys Met Ile Ala
            405             410             415

His Asp Phe Pro Gly Ile Gly His Lys Val Asp Ala Val Phe Met Lys
            420             425             430

Asp Gly Phe Phe Tyr Phe Phe His Gly Thr Arg Gln Tyr Lys Phe Asp
            435             440             445

Pro Lys Thr Lys Arg Ile Leu Thr Leu Gln Lys Ala Asn Ser Trp Phe
            450             455             460

Asn Cys Arg Lys Asn
465

<210> SEQ ID NO 24
<211> LENGTH: 467
<212> TYPE: PRT
<213> ORGANISM: Homo sapiens

<400> SEQUENCE: 24

Met Phe Ser Leu Lys Thr Leu Pro Phe Leu Leu Leu His Val Gln
1               5               10              15

Ile Ser Lys Ala Phe Pro Val Ser Ser Lys Glu Lys Asn Thr Lys Thr
            20              25              30

Val Gln Asp Tyr Leu Glu Lys Phe Tyr Gln Leu Pro Ser Asn Gln Tyr
            35              40              45

Gln Ser Thr Arg Lys Asn Gly Thr Asn Val Ile Val Glu Lys Leu Lys
        50              55              60

Glu Met Gln Arg Phe Phe Gly Leu Asn Val Thr Gly Lys Pro Asn Glu
65              70              75              80

Glu Thr Leu Asp Met Met Lys Lys Pro Arg Cys Gly Val Pro Asp Ser
                85              90              95

Gly Gly Phe Met Leu Thr Pro Gly Asn Pro Lys Trp Glu Arg Thr Asn
            100             105             110

Leu Thr Tyr Arg Ile Arg Asn Tyr Thr Pro Gln Leu Ser Glu Ala Glu
        115             120             125

Val Glu Arg Ala Ile Lys Asp Ala Phe Glu Leu Trp Ser Val Ala Ser
130             135             140

Pro Leu Ile Phe Thr Arg Ile Ser Gln Gly Glu Ala Asp Ile Asn Ile
145             150             155             160

Ala Phe Tyr Gln Arg Asp His Gly Asp Asn Ser Pro Phe Asp Gly Pro
            165             170             175

Asn Gly Ile Leu Ala His Ala Phe Gln Pro Gly Gln Gly Ile Gly Gly
            180             185             190

Asp Ala His Phe Asp Ala Glu Glu Thr Trp Thr Asn Thr Ser Ala Asn
        195             200             205

Tyr Asn Leu Phe Leu Val Ala Ala His Glu Phe Gly His Ser Leu Gly
        210             215             220

Leu Ala His Ser Ser Asp Pro Gly Ala Leu Met Tyr Pro Asn Tyr Ala
225             230             235             240
```

```
Phe Arg Glu Thr Ser Asn Tyr Ser Leu Pro Gln Asp Asp Ile Asp Gly
                245                 250                 255

Ile Gln Ala Ile Tyr Gly Leu Ser Ser Asn Pro Ile Gln Pro Thr Gly
            260                 265                 270

Pro Ser Thr Pro Lys Pro Cys Asp Pro Ser Leu Thr Phe Asp Ala Ile
        275                 280                 285

Thr Thr Leu Arg Gly Glu Ile Leu Phe Lys Asp Arg Tyr Phe Trp
290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
                340                 345                 350

Ser Gly Tyr Asp Ile Leu Gln Gly Tyr Pro Lys Asp Ile Ser Asn Tyr
                355                 360                 365

Gly Phe Pro Ser Ser Val Gln Ala Ile Asp Ala Ala Val Phe Tyr Arg
370                 375                 380

Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415

Phe Pro Gly Ile Glu Ser Lys Val Asp Ala Val Phe Gln Gln Glu His
                420                 425                 430

Phe Phe His Val Phe Ser Gly Pro Arg Tyr Tyr Ala Phe Asp Leu Ile
            435                 440                 445

Ala Gln Arg Val Thr Arg Val Ala Arg Gly Asn Lys Trp Leu Asn Cys
        450                 455                 460

Arg Tyr Gly
465
```

<210> SEQ ID NO 25
<211> LENGTH: 471
<212> TYPE: PRT
<213> ORGANISM: Homo sapiens

<400> SEQUENCE: 25

```
Met His Pro Gly Val Leu Ala Ala Phe Leu Phe Leu Ser Trp Thr His
  1               5                  10                  15

Cys Arg Ala Leu Pro Leu Pro Ser Gly Gly Asp Glu Asp Asp Leu Ser
                20                  25                  30

Glu Glu Asp Leu Gln Phe Ala Glu Arg Tyr Leu Arg Ser Tyr Tyr His
            35                  40                  45

Pro Thr Asn Leu Ala Gly Ile Leu Lys Glu Asn Ala Ala Ser Ser Met
        50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
                100                 105                 110

Trp Ser Lys Met Asn Leu Thr Tyr Arg Ile Val Asn Tyr Thr Pro Asp
            115                 120                 125

Met Thr His Ser Glu Val Glu Lys Ala Phe Lys Lys Ala Phe Lys Val
        130                 135                 140
```

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
            165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
            195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
            245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
            275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
            325                 330                 335

Ala Tyr Glu His Pro Ser His Asp Leu Ile Phe Ile Phe Arg Gly Arg
            340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
            370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
            405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470

<210> SEQ ID NO 26
<211> LENGTH: 470
<212> TYPE: PRT
<213> ORGANISM: Homo sapiens

<400> SEQUENCE: 26

Met Lys Phe Leu Leu Ile Leu Leu Leu Gln Ala Thr Ala Ser Gly Ala
 1               5                   10                  15

Leu Pro Leu Asn Ser Ser Thr Ser Leu Glu Lys Asn Asn Val Leu Phe
            20                  25                  30

Gly Glu Arg Tyr Leu Glu Lys Phe Tyr Gly Leu Glu Ile Asn Lys Leu

-continued

```
                35                    40                      45
    Pro Val Thr Lys Met Lys Tyr Ser Gly Asn L eu Met Lys Glu Lys Ile
    50                      55                  60
Gln Glu Met Gln His Phe Leu Gly Leu Lys V al Thr Gly Gln Leu Asp
65                  70                  75                      80
Thr Ser Thr Leu Glu Met Met His Ala Pro A rg Cys Gly Val Pro Asp
                85                  90                  95
Val His His Phe Arg Glu Met Pro Gly Gly P ro Val Trp Arg Lys His
            100                 105                 110
Tyr Ile Thr Tyr Arg Ile Asn Asn Tyr Thr P ro Asp Met Asn Arg Glu
        115                 120                 125
Asp Val Asp Tyr Ala Ile Arg Lys Ala Phe G ln Val Trp Ser Asn Val
130                 135                 140
Thr Pro Leu Lys Phe Ser Lys Ile Asn Thr G ly Met Ala Asp Ile Leu
145                 150                 155                 160
Val Val Phe Ala Arg Gly Ala His Gly Asp P he His Ala Phe Asp Gly
                165                 170                 175
Lys Gly Gly Ile Leu Ala His Ala Phe Gly P ro Gly Ser Gly Ile Gly
            180                 185                 190
Gly Asp Ala His Phe Asp Glu Asp Glu Phe T rp Thr Thr His Ser Gly
        195                 200                 205
Gly Thr Asn Leu Phe Leu Thr Ala Val His G lu Ile Gly His Ser Leu
210                 215                 220
Gly Leu Gly His Ser Ser Asp Pro Lys Ala V al Met Phe Pro Thr Tyr
225                 230                 235                 240
Lys Tyr Val Asp Ile Asn Thr Phe Arg Leu S er Ala Asp Asp Ile Arg
                245                 250                 255
Gly Ile Gln Ser Leu Tyr Gly Asp Pro Lys G lu Asn Gln Arg Leu Pro
            260                 265                 270
Asn Pro Asp Asn Ser Glu Pro Ala Leu Cys A sp Pro Asn Leu Ser Phe
        275                 280                 285
Asp Ala Val Thr Thr Val Gly Asn Lys Ile P he Phe Lys Asp Arg
290                 295                 300
Phe Phe Trp Leu Lys Val Ser Glu Arg Pro L ys Thr Ser Val Asn Leu
305                 310                 315                 320
Ile Ser Ser Leu Trp Pro Thr Leu Pro Ser G ly Ile Glu Ala Ala Tyr
                325                 330                 335
Glu Ile Glu Ala Arg Asn Gln Val Phe Leu P he Lys Asp Asp Lys Tyr
            340                 345                 350
Trp Leu Ile Ser Asn Leu Arg Pro Glu Pro A sn Tyr Pro Lys Ser Ile
        355                 360                 365
His Ser Phe Gly Phe Pro Asn Phe Val Lys L ys Ile Asp Ala Ala Val
370                 375                 380
Phe Asn Pro Arg Phe Tyr Arg Thr Tyr Phe P he Val Asp Asn Gln Tyr
385                 390                 395                 400
Trp Arg Tyr Asp Glu Arg Arg Gln Met Met A sp Pro Gly Tyr Pro Lys
                405                 410                 415
Leu Ile Thr Lys Asn Phe Gln Gly Ile Gly P ro Lys Ile Asp Ala Val
            420                 425                 430
Phe Tyr Ser Lys Asn Lys Tyr Tyr Phe P he Gln Gly Ser Asn Gln
        435                 440                 445
Phe Glu Tyr Asp Phe Leu Leu Gln Arg Ile T hr Lys Thr Leu Lys Ser
450                 455                 460
```

Asn Ser Trp Phe Gly Cys
465                 470

<210> SEQ ID NO 27
<211> LENGTH: 267
<212> TYPE: PRT
<213> ORGANISM: Homo sapiens

<400> SEQUENCE: 27

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe Tyr Leu Tyr Asp Ser Glu
        35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205

Leu Tyr Ala Ala Thr His Glu Leu Gly His Ser Leu Gly Met Gly His
    210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
            260                 265

<210> SEQ ID NO 28
<211> LENGTH: 582
<212> TYPE: PRT
<213> ORGANISM: Homo sapiens

<400> SEQUENCE: 28

Met Ser Pro Ala Pro Arg Pro Ser Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

```
Asp Leu Arg Thr His Thr Gln Arg Ser Pro G ln Ser Leu Ser Ala Ala
    50                  55                  60
Ile Ala Ala Met Gln Lys Phe Tyr Gly Leu G ln Val Thr Gly Lys Ala
65                  70                  75                  80
Asp Ala Asp Thr Met Lys Ala Met Arg Arg P ro Arg Cys Gly Val Pro
                85                  90                  95
Asp Lys Phe Gly Ala Glu Ile Lys Ala Asn V al Arg Arg Lys Arg Tyr
            100                 105                 110
Ala Ile Gln Gly Leu Lys Trp Gln His Asn G lu Ile Thr Phe Cys Ile
        115                 120                 125
Gln Asn Tyr Thr Pro Lys Val Gly Tyr A la Thr Tyr Glu Ala Ile
    130                 135                 140
Arg Lys Ala Phe Arg Val Trp Glu Ser Ala T hr Pro Leu Arg Phe Arg
145                 150                 155                 160
Glu Val Pro Tyr Ala Tyr Ile Arg Glu Gly H is Glu Lys Gln Ala Asp
                165                 170                 175
Ile Met Ile Phe Phe Ala Glu Gly Phe His G ly Asp Ser Thr Pro Phe
            180                 185                 190
Asp Gly Glu Gly Gly Phe Leu Ala His Ala T yr Phe Pro Gly Pro Asn
        195                 200                 205
Ile Gly Gly Asp Thr His Phe Asp Ser Ala G lu Pro Trp Thr Val Arg
    210                 215                 220
Asn Glu Asp Leu Asn Gly Asn Asp Ile Phe L eu Val Ala Val His Glu
225                 230                 235                 240
Leu Gly His Ala Leu Gly Leu Glu His Ser S er Asp Pro Ser Ala Ile
                245                 250                 255
Met Ala Pro Phe Tyr Gln Trp Met Asp Thr G lu Asn Phe Val Leu Pro
            260                 265                 270
Asp Asp Asp Arg Arg Gly Ile Gln Gln Leu T yr Gly Gly Glu Ser Gly
        275                 280                 285
Phe Pro Thr Lys Met Pro Pro Gln Pro Arg T hr Thr Ser Arg Pro Ser
    290                 295                 300
Val Pro Asp Lys Pro Lys Asn Pro Thr Tyr G ly Pro Asn Ile Cys Asp
305                 310                 315                 320
Gly Asn Phe Asp Thr Val Ala Met Leu Arg G ly Glu Met Phe Val Phe
                325                 330                 335
Lys Lys Arg Trp Phe Trp Arg Val Arg Asn A sn Gln Val Met Asp Gly
            340                 345                 350
Tyr Pro Met Pro Ile Gly Gln Phe Trp Arg G ly Leu Pro Ala Ser Ile
        355                 360                 365
Asn Thr Ala Tyr Glu Arg Lys Asp Gly Lys P he Val Phe Lys Gly
    370                 375                 380
Asp Lys His Trp Val Phe Asp Glu Ala Ser L eu Glu Pro Gly Tyr Pro
385                 390                 395                 400
Lys His Ile Lys Glu Leu Gly Arg Gly Leu P ro Thr Asp Lys Ile Asp
                405                 410                 415
Ala Ala Leu Phe Trp Met Pro Asn Gly Lys T hr Tyr Phe Phe Arg Gly
            420                 425                 430
Asn Lys Tyr Tyr Arg Phe Asn Glu Glu Leu A rg Ala Val Asp Ser Glu
        435                 440                 445
Tyr Pro Lys Asn Ile Lys Val Trp Glu Gly I le Pro Glu Ser Pro Arg
    450                 455                 460
```

```
Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
            485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
        515                 520                 525

Val Asp Glu Glu Gly Gly Ala Val Ser Ala Ala Ala Val Val Leu
    530                 535                 540

Pro Val Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580
```

<210> SEQ ID NO 29
<211> LENGTH: 669
<212> TYPE: PRT
<213> ORGANISM: Homo sapiens

<400> SEQUENCE: 29

```
Met Gly Ser Asp Pro Ser Ala Pro Gly Arg Pro Gly Trp Thr Gly Ser
1               5                   10                  15

Leu Leu Gly Asp Arg Glu Ala Ala Arg Pro Arg Leu Leu Pro Leu
            20                  25                  30

Leu Leu Val Leu Leu Gly Cys Leu Gly Leu Gly Val Ala Ala Glu Asp
            35                  40                  45

Ala Glu Val His Ala Glu Asn Trp Leu Arg Leu Tyr Gly Tyr Leu Pro
    50                  55                  60

Gln Pro Ser Arg His Met Ser Thr Met Arg Ser Ala Gln Ile Leu Ala
65                  70                  75                  80

Ser Ala Leu Ala Glu Met Gln Arg Phe Tyr Gly Ile Pro Val Thr Gly
                85                  90                  95

Val Leu Asp Glu Glu Thr Lys Glu Trp Met Lys Arg Pro Arg Cys Gly
                100                 105                 110

Val Pro Asp Gln Phe Gly Val Arg Val Lys Ala Asn Leu Arg Arg Arg
            115                 120                 125

Arg Lys Arg Tyr Ala Leu Thr Gly Arg Lys Trp Asn His His Leu
        130                 135                 140

Thr Phe Ser Ile Gln Asn Tyr Thr Glu Lys Leu Gly Trp Tyr His Ser
145                 150                 155                 160

Met Glu Ala Val Arg Arg Ala Phe Arg Val Trp Glu Gln Ala Thr Pro
                165                 170                 175

Leu Val Phe Gln Glu Val Pro Tyr Glu Asp Ile Arg Leu Arg Arg Gln
            180                 185                 190

Lys Glu Ala Asp Ile Met Val Leu Phe Ala Ser Gly Phe His Gly Asp
        195                 200                 205

Ser Ser Pro Phe Asp Gly Thr Gly Gly Phe Leu Ala His Ala Tyr Phe
    210                 215                 220

Pro Gly Pro Gly Leu Gly Gly Asp Thr His Phe Asp Ala Asp Glu Pro
225                 230                 235                 240

Trp Thr Phe Ser Ser Thr Asp Leu His Gly Asn Asn Leu Phe Leu Val
                245                 250                 255
```

-continued

```
Ala Val His Glu Leu Gly His Ala Leu Gly Leu Glu His Ser Ser Asn
            260                 265                 270
Pro Asn Ala Ile Met Ala Pro Phe Tyr Gln Trp Lys Asp Val Asp Asn
            275                 280                 285
Phe Lys Leu Pro Glu Asp Leu Arg Gly Ile Gln Gln Leu Tyr Gly
            290                 295                 300
Thr Pro Asp Gly Gln Pro Gln Pro Thr Gln Pro Leu Pro Thr Val Thr
305                 310                 315                 320
Pro Arg Arg Pro Gly Arg Pro Asp His Arg Pro Arg Pro Pro Gln
            325                 330                 335
Pro Pro Pro Pro Gly Gly Lys Pro Glu Arg Pro Pro Lys Pro Gly Pro
            340                 345                 350
Pro Val Gln Pro Arg Ala Thr Glu Arg Pro Asp Gln Tyr Gly Pro Asn
            355                 360                 365
Ile Cys Asp Gly Asp Phe Asp Thr Val Ala Met Leu Arg Gly Glu Met
            370                 375                 380
Phe Val Phe Lys Gly Arg Trp Phe Trp Arg Val Arg His Asn Arg Val
385                 390                 395                 400
Leu Asp Asn Tyr Pro Met Pro Ile Gly His Phe Trp Arg Gly Leu Pro
            405                 410                 415
Gly Asp Ile Ser Ala Ala Tyr Glu Arg Gln Asp Gly Arg Phe Val Phe
            420                 425                 430
Phe Lys Gly Asp Arg Tyr Trp Leu Phe Arg Glu Ala Asn Leu Glu Pro
            435                 440                 445
Gly Tyr Pro Gln Pro Leu Thr Ser Tyr Gly Leu Gly Ile Pro Tyr Asp
            450                 455                 460
Arg Ile Asp Thr Ala Ile Trp Trp Glu Pro Thr Gly His Thr Phe Phe
465                 470                 475                 480
Phe Gln Glu Asp Arg Tyr Trp Arg Phe Asn Glu Glu Thr Gln Arg Gly
            485                 490                 495
Asp Pro Gly Tyr Pro Lys Pro Ile Ser Val Trp Gln Gly Ile Pro Ala
            500                 505                 510
Ser Pro Lys Gly Ala Phe Leu Ser Asn Asp Ala Ala Tyr Thr Tyr Phe
            515                 520                 525
Tyr Lys Gly Thr Lys Tyr Trp Lys Phe Asp Asn Glu Arg Leu Arg Met
            530                 535                 540
Glu Pro Gly Tyr Pro Lys Ser Ile Leu Arg Asp Phe Met Gly Cys Gln
545                 550                 555                 560
Glu His Val Glu Pro Gly Pro Arg Trp Pro Asp Val Ala Arg Pro Pro
            565                 570                 575
Phe Asn Pro His Gly Gly Ala Glu Pro Gly Ala Asp Ser Ala Glu Gly
            580                 585                 590
Asp Val Gly Asp Gly Asp Gly Asp Phe Gly Ala Gly Val Asn Lys Asp
            595                 600                 605
Gly Gly Ser Arg Val Val Gln Met Glu Glu Val Ala Arg Thr Val
            610                 615                 620
Asn Val Val Met Val Leu Val Pro Leu Leu Leu Leu Leu Cys Val Leu
625                 630                 635                 640
Gly Leu Thr Tyr Ala Leu Val Gln Met Gln Arg Lys Gly Ala Pro Arg
            645                 650                 655
Val Leu Leu Tyr Cys Lys Arg Ser Leu Gln Glu Trp Val
            660                 665
```

-continued

```
<210> SEQ ID NO 30
<211> LENGTH: 604
<212> TYPE: PRT
<213> ORGANISM: Homo sapiens

<400> SEQUENCE: 30
```

| | | | | | | | | | | | | | | |
|---|---|---|---|---|---|---|---|---|---|---|---|---|---|---|
| Met | Ile | Leu | Leu | Thr | Phe | Ser | Thr | Gly | Arg | Arg | Leu | Asp | Phe | Val | His |
| 1 | | | | 5 | | | | | 10 | | | | | 15 | |
| His | Ser | Gly | Val | Phe | Phe | Leu | Gln | Thr | Leu | Leu | Trp | Ile | Leu | Cys | Ala |
| | | | 20 | | | | | 25 | | | | | 30 | | |
| Thr | Val | Cys | Gly | Thr | Glu | Gln | Tyr | Phe | Asn | Val | Glu | Val | Trp | Leu | Gln |
| | | 35 | | | | | 40 | | | | | 45 | | | |
| Lys | Tyr | Gly | Tyr | Leu | Pro | Pro | Thr | Ser | Pro | Arg | Met | Ser | Val | Val | Arg |
| 50 | | | | | 55 | | | | | 60 | | | | | |
| Ser | Ala | Glu | Thr | Met | Gln | Ser | Ala | Leu | Ala | Ala | Met | Gln | Gln | Phe | Tyr |
| 65 | | | | | 70 | | | | 75 | | | | | 80 | |
| Gly | Ile | Asn | Met | Thr | Gly | Lys | Val | Asp | Arg | Asn | Thr | Ile | Asp | Trp | Met |
| | | | | 85 | | | | | 90 | | | | | 95 | |
| Lys | Lys | Pro | Arg | Cys | Gly | Val | Pro | Asp | Gln | Thr | Arg | Gly | Ser | Ser | Lys |
| | | | | 100 | | | | | 105 | | | | | 110 | |
| Phe | His | Ile | Arg | Arg | Lys | Arg | Tyr | Ala | Leu | Thr | Gly | Gln | Lys | Trp | Gln |
| | | | 115 | | | | | 120 | | | | | 125 | | |
| His | Lys | His | Ile | Thr | Tyr | Ser | Ile | Lys | Asn | Val | Thr | Pro | Lys | Val | Gly |
| | 130 | | | | | 135 | | | | | 140 | | | | |
| Asp | Pro | Glu | Thr | Arg | Lys | Ala | Ile | Arg | Arg | Ala | Phe | Asp | Val | Trp | Gln |
| 145 | | | | | 150 | | | | | 155 | | | | | 160 |
| Asn | Val | Thr | Pro | Leu | Thr | Phe | Glu | Glu | Val | Pro | Tyr | Ser | Glu | Leu | Glu |
| | | | | 165 | | | | | 170 | | | | | 175 | |
| Asn | Gly | Lys | Arg | Asp | Val | Asp | Ile | Pro | Ile | Ile | Phe | Ala | Ser | Gly | Phe |
| | | | 180 | | | | | 185 | | | | | 190 | | |
| His | Gly | Asp | Ser | Ser | Pro | Phe | Asp | Gly | Glu | Gly | Gly | Phe | Leu | Ala | His |
| | | 195 | | | | | 200 | | | | | 205 | | | |
| Ala | Tyr | Phe | Pro | Gly | Pro | Gly | Ile | Gly | Gly | Asp | Thr | His | Phe | Asp | Ser |
| | 210 | | | | | 215 | | | | | 220 | | | | |
| Asp | Glu | Pro | Trp | Thr | Leu | Gly | Asn | Pro | Asn | His | Asp | Gly | Asn | Asp | Leu |
| 225 | | | | | 230 | | | | | 235 | | | | | 240 |
| Phe | Leu | Val | Ala | Val | His | Glu | Leu | Gly | His | Ala | Leu | Gly | Leu | Glu | His |
| | | | | 245 | | | | | 250 | | | | | 255 | |
| Ser | Asn | Asp | Pro | Thr | Ala | Ile | Met | Ala | Pro | Phe | Tyr | Gln | Tyr | Met | Glu |
| | | | 260 | | | | | 265 | | | | | 270 | | |
| Gln | Thr | Leu | Gln | Leu | Pro | Asn | Asp | Asp | Tyr | Arg | His | Gln | Arg | Tyr | Met |
| | | 275 | | | | | 280 | | | | | 285 | | | |
| Ser | Pro | Asp | Lys | Ile | Pro | Pro | Pro | Thr | Arg | Pro | Leu | Pro | Thr | Val | Pro |
| | 290 | | | | | 295 | | | | | 300 | | | | |
| Pro | His | Arg | Ser | Ile | Pro | Pro | Ala | Asp | Pro | Arg | Lys | Asn | Asp | Arg | Pro |
| 305 | | | | | 310 | | | | | 315 | | | | | 320 |
| Lys | Pro | Pro | Arg | Pro | Pro | Thr | Gly | Arg | Pro | Ser | Tyr | Pro | Gly | Ala | Lys |
| | | | | 325 | | | | | 330 | | | | | 335 | |
| Pro | Asn | Ile | Cys | Asp | Gly | Asn | Phe | Asn | Thr | Leu | Ala | Ile | Leu | Arg | Arg |
| | | | 340 | | | | | 345 | | | | | 350 | | |
| Glu | Met | Phe | Val | Phe | Lys | Asp | Gln | Trp | Phe | Trp | Arg | Val | Arg | Asn | Asn |
| | | 355 | | | | | 360 | | | | | 365 | | | |
| Arg | Val | Met | Asp | Gly | Tyr | Pro | Met | Gln | Ile | Thr | Tyr | Phe | Trp | Arg | Gly |
| | 370 | | | | | 375 | | | | | 380 | | | | |

-continued

```
Leu Pro Pro Ser Ile Asp Ala Val Tyr Glu Asn Ser Asp Gly Asn Phe
385                 390                 395                 400

Val Phe Phe Lys Gly Asn Lys Tyr Trp Val Phe Lys Asp Thr Thr Leu
                405                 410                 415

Gln Pro Gly Tyr Pro His Asp Leu Ile Thr Leu Gly Ser Gly Ile Pro
            420                 425                 430

Pro His Gly Ile Asp Ser Ala Ile Trp Trp Glu Asp Val Gly Lys Thr
        435                 440                 445

Tyr Phe Phe Lys Gly Asp Arg Tyr Trp Arg Tyr Ser Glu Glu Met Lys
    450                 455                 460

Thr Met Asp Pro Gly Tyr Pro Lys Pro Ile Thr Val Trp Lys Gly Ile
465                 470                 475                 480

Pro Glu Ser Pro Gln Gly Ala Phe Val His Lys Glu Asn Gly Phe Thr
                485                 490                 495

Tyr Phe Tyr Lys Glu Gly Val Leu Glu Ile Gln Thr Thr Arg Tyr Ser
            500                 505                 510

Arg Leu Glu Pro Gly His Pro Arg Ser Ile Leu Lys Asp Leu Ser Gly
        515                 520                 525

Cys Asp Gly Pro Thr Asp Arg Val Lys Glu Gly His Ser Pro Pro Asp
    530                 535                 540

Asp Val Asp Ile Val Ile Lys Leu Asp Asn Thr Ala Ser Thr Val Lys
545                 550                 555                 560

Ala Ile Ala Ile Val Ile Pro Cys Ile Leu Ala Leu Cys Leu Leu Val
                565                 570                 575

Leu Val Tyr Thr Val Phe Gln Phe Lys Arg Lys Gly Thr Pro Arg His
            580                 585                 590

Ile Leu Tyr Cys Lys Arg Ser Met Gln Glu Trp Val
        595                 600

<210> SEQ ID NO 31
<211> LENGTH: 488
<212> TYPE: PRT
<213> ORGANISM: Homo sapiens

<400> SEQUENCE: 31

Met Ala Pro Ala Ala Trp Leu Arg Ser Ala Ala Ala Arg Ala Leu Leu
1               5                   10                  15

Pro Pro Met Leu Leu Leu Leu Gln Pro Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
            100                 105                 110

Arg Ile Leu Arg Phe Pro Trp Gln Leu Val Gln Glu Gln Val Arg Gln
        115                 120                 125

Thr Met Ala Glu Ala Leu Lys Val Trp Ser Asp Val Thr Pro Leu Thr
    130                 135                 140

Phe Thr Glu Val His Glu Gly Arg Ala Asp Ile Met Ile Asp Phe Ala
```

```
                145                 150                 155                 160
Arg Tyr Trp Asp Gly Asp Asp Leu Pro Phe Asp Gly Pro Gly Gly Ile
                    165                 170                 175

Leu Ala His Ala Phe Phe Pro Lys Thr His Arg Glu Gly Asp Val His
                180                 185                 190

Phe Asp Tyr Asp Glu Thr Trp Thr Ile Gly Asp Asp Gln Gly Thr Asp
                195                 200                 205

Leu Leu Gln Val Ala Ala His Glu Phe Gly His Val Leu Gly Leu Gln
            210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                    245                 250                 255

Tyr Gly Gln Pro Trp Pro Thr Val Thr Ser Arg Thr Pro Ala Leu Gly
                260                 265                 270

Pro Gln Ala Gly Ile Asp Thr Asn Glu Ile Ala Pro Leu Glu Pro Asp
            275                 280                 285

Ala Pro Pro Asp Ala Cys Glu Ala Ser Phe Asp Ala Val Ser Thr Ile
        290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                    325                 330                 335

Gln Gly Leu Pro Ser Pro Val Asp Ala Ala Phe Glu Asp Ala Gln Gly
                340                 345                 350

His Ile Trp Phe Phe Gln Gly Ala Gln Tyr Trp Val Tyr Asp Gly Glu
            355                 360                 365

Lys Pro Val Leu Gly Pro Ala Pro Leu Thr Glu Leu Gly Leu Val Arg
        370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                    405                 410                 415

Arg Val Asp Ser Pro Val Pro Arg Arg Ala Thr Asp Trp Arg Gly Val
                420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
        450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                    485

<210> SEQ ID NO 32
<211> LENGTH: 517
<212> TYPE: PRT
<213> ORGANISM: Homo sapiens

<400> SEQUENCE: 32

Met Gln Gln Phe Gly Gly Leu Glu Ala Thr Gly Ile Asp Glu Ala Thr
1               5                   10                  15

Leu Ala Leu Met Lys Thr Pro Arg Cys Ser Leu Pro Asp Leu Pro Val
                20                  25                  30
```

-continued

```
Leu Thr Gln Ala Arg Arg Arg Gln Ala Pro Ala Pro Thr Lys Trp
         35                  40                  45

Asn Lys Arg Asn Leu Ser Trp Arg Val Arg Thr Phe Pro Arg Asp Ser
 50                  55                  60

Pro Leu Gly His Asp Thr Val Arg Ala Leu Met Tyr Tyr Ala Leu Lys
 65                  70                  75                  80

Val Trp Ser Asp Ile Ala Pro Leu Asn Phe His Glu Val Ala Gly Ser
                 85                  90                  95

Thr Ala Asp Ile Gln Ile Asp Phe Ser Lys Ala Asp His Asn Asp Gly
             100                 105                 110

Tyr Pro Phe Asp Ala Arg Arg His Arg Ala His Ala Phe Phe Pro Gly
         115                 120                 125

His His His Thr Ala Gly Tyr Thr His Phe Asn Asp Glu Ala Trp
 130                 135                 140

Thr Phe Arg Ser Ser Asp Ala His Gly Met Asp Leu Phe Ala Val Ala
145                 150                 155                 160

Val His Glu Phe Gly His Ala Ile Gly Leu Ser His Val Ala Ala Ala
                 165                 170                 175

His Ser Ile Met Arg Pro Tyr Tyr Gln Gly Pro Val Gly Asp Pro Leu
             180                 185                 190

Arg Tyr Gly Leu Pro Tyr Glu Asp Lys Val Arg Val Trp Gln Leu Tyr
         195                 200                 205

Gly Val Arg Glu Ser Val Ser Pro Thr Ala Gln Pro Glu Pro Pro
 210                 215                 220

Leu Leu Pro Glu Pro Pro Asp Asn Arg Ser Ser Ala Pro Pro Arg Lys
225                 230                 235                 240

Asp Val Pro His Arg Cys Ser Thr His Phe Asp Ala Val Ala Gln Ile
                 245                 250                 255

Arg Gly Glu Ala Phe Phe Phe Lys Gly Lys Tyr Phe Trp Arg Leu Thr
             260                 265                 270

Arg Asp Arg His Leu Val Ser Leu Gln Pro Ala Gln Met His Arg Phe
         275                 280                 285

Trp Arg Gly Leu Pro Leu His Leu Asp Ser Val Asp Ala Val Tyr Glu
 290                 295                 300

Arg Thr Ser Asp His Lys Ile Val Phe Phe Lys Gly Asp Arg Tyr Trp
305                 310                 315                 320

Val Phe Lys Asp Asn Asn Val Glu Glu Gly Tyr Pro Arg Pro Val Ser
                 325                 330                 335

Asp Phe Ser Leu Pro Pro Gly Gly Ile Asp Ala Ala Phe Ser Trp Ala
             340                 345                 350

His Asn Asp Arg Thr Tyr Phe Phe Lys Asp Gln Leu Tyr Trp Arg Tyr
         355                 360                 365

Asp Asp His Thr Arg His Met Asp Pro Gly Tyr Pro Ala Gln Ser Pro
 370                 375                 380

Leu Trp Arg Gly Val Pro Ser Thr Leu Asp Ala Met Arg Trp Ser
385                 390                 395                 400

Asp Gly Ala Ser Tyr Phe Phe Arg Gly Gln Glu Tyr Trp Lys Val Leu
                 405                 410                 415

Asp Gly Glu Leu Glu Val Ala Pro Gly Tyr Pro Gln Ser Thr Ala Arg
             420                 425                 430

Asp Trp Leu Val Cys Gly Asp Ser Gln Ala Asp Gly Ser Val Ala Ala
         435                 440                 445

Gly Val Asp Ala Ala Glu Gly Pro Arg Ala Pro Pro Gly Gln His Asp
```

```
                     450                 455                 460
Gln Ser Arg Ser Glu Asp Gly Tyr Glu Val Cys Ser Cys Thr Ser Gly
465                 470                 475                 480

Ala Ser Ser Pro Pro Gly Ala Pro Gly Pro Leu Val Ala Ala Thr Met
                485                 490                 495

Leu Leu Leu Leu Pro Pro Leu Ser Pro Gly Ala Leu Trp Thr Ala Ala
                500                 505                 510

Gln Ala Leu Thr Leu
        515

<210> SEQ ID NO 33
<211> LENGTH: 4
<212> TYPE: PRT
<213> ORGANISM: Unknown
<220> FEATURE:
<223> OTHER INFORMATION: Potential recognition and  cleavage site for
      Kex2-like proteases
<223> OTHER INFORMATION: Xaa = Unknown or Other at position 2

<400> SEQUENCE: 33

Arg Xaa Lys Arg
 1

<210> SEQ ID NO 34
<211> LENGTH: 13
<212> TYPE: DNA
<213> ORGANISM: Homo sapiens
<220> FEATURE:
<223> OTHER INFORMATION: r = g or a at  position 7

<400> SEQUENCE: 34
ggcggcraga tgg                                                                13

<210> SEQ ID NO 35
<211> LENGTH: 13
<212> TYPE: DNA
<213> ORGANISM: Homo sapiens
<220> FEATURE:
<223> OTHER INFORMATION: r = g or a at  position 7

<400> SEQUENCE: 35
gccgccrcca tgg                                                                13
```